(12) United States Patent
Kamon et al.

(10) Patent No.: US 7,339,014 B2
(45) Date of Patent: Mar. 4, 2008

(54) (METH)ACRYLATE, RAW MATERIAL ALCOHOL FOR THE (METH)ACRYLATE, METHOD OF PRODUCING THE (METH)ACRYLATE AND THE ALCOHOL, POLYMER PRODUCED BY POLYMERIZING THE (METH)ACRYLATE, CHEMICALLY AMPLIFIED RESIST COMPOSITION, AND METHOD OF THE FORMATION OF A PATTERN

(75) Inventors: Yoshihiro Kamon, Hiroshima (JP); Tadayuki Fujiwara, Kanagawa (JP); Hideaki Kuwano, Kanagawa (JP); Hikaru Momose, Kanagawa (JP); Atsushi Koizumi, Hiroshima (JP)

(73) Assignee: Mitsubishi Rayon Co., Ltd., Tokyo (JP)

( * ) Notice: Subject to any disclaimer, the term of this patent is extended or adjusted under 35 U.S.C. 154(b) by 361 days.

(21) Appl. No.: 10/974,876

(22) Filed: Oct. 28, 2004

(65) Prior Publication Data

US 2005/0113538 A1    May 26, 2005

Related U.S. Application Data

(62) Division of application No. 10/433,570, filed as application No. PCT/JP01/10628 on Dec. 5, 2001, now Pat. No. 7,041,838.

(30) Foreign Application Priority Data

| Dec. 6, 2000 | (JP) | ............................. 2000-371712 |
| Jan. 9, 2001 | (JP) | ............................. 2001-001728 |
| Nov. 30, 2001 | (JP) | ............................. 2001-366958 |
| Dec. 3, 2001 | (JP) | ............................. 2001-368904 |

(51) Int. Cl.
*C08F 24/00* (2006.01)
*C08F 34/02* (2006.01)

(52) U.S. Cl. ...................... 526/268; 526/271; 526/281; 526/282; 526/283; 526/284; 526/320

(58) Field of Classification Search ................ 526/268, 526/271, 281, 282, 283, 284, 320
See application file for complete search history.

(56) References Cited

U.S. PATENT DOCUMENTS

| 4,143,054 A | 3/1979 | Sprague |
| 4,187,236 A | 2/1980 | Sprague |
| 4,370,387 A | 1/1983 | Ueno et al. |
| 6,280,898 B1 * | 8/2001 | Hasegawa et al. ........ 430/270.1 |
| 6,461,788 B1 * | 10/2002 | Miwa et al. ............. 430/270.1 |
| 7,186,495 B2 * | 3/2007 | Maeda et al. ............. 430/270.1 |
| 2002/0102492 A1 | 8/2002 | Iwai et al. |

FOREIGN PATENT DOCUMENTS

| JP | 2001-242627 | 9/2001 |
| JP | 2002-6502 | 1/2002 |
| JP | 2002006502 | 1/2002 |
| JP | 2002-162745 | 6/2002 |
| WO | WO 00/01684 | 1/2000 |

OTHER PUBLICATIONS

Kenji Mori et al.: "Synthetic microbial chemistry. XXV. Synthesis of the enantiomers of differolide [4-(2',5'-dihydro-2'-oxo-3'furanyl)-3a,4,5,6-tetrahydro-1(3H)-isobenzofuranone], a microbial bioregulator for the formation of aerial mycelium and spores of streptomyces glaucescens" Liebigs Ann. Chem., vol. 6, pp. 671-681, compound 6, 1993.

Atsushi Numata et al.: "Synthesis of pyrolysis products of bisdehydrodihydroenmein. I. Synthesis of 6-hydroxy-7-methylphthalide and 2-(hydroxymethyl)-6,6-dimethyl-5-oxo-1-cyclohexenecarboxylic acid lactone" Yakugaku Zasshi, vol. 88, No. 9, pp. 1151-1162, 1968.

* cited by examiner

*Primary Examiner*—Helen L. Pezzuto
(74) *Attorney, Agent, or Firm*—Oblon, Spivak, McClelland, Maier & Neustadt, P.C.

(57) ABSTRACT

A (meth)acrylate represented by the following formula (1):

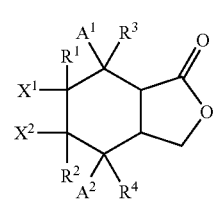

wherein each of $R^1$, $R^2$, $R^3$ and $R^4$ represents a hydrogen atom, a methyl group or an ethyl group; either one of $X^1$ or $X^2$ represents a (meth)acryloyloxy group and the other represents a hydrogen atom; both $A^1$ and $A^2$ represent hydrogen atoms, or $A^1$ and $A^2$ form —O—, —CH$_2$— or —CH$_2$CH$_2$—, which can be produced by first producing a lactone by reducing an addition product obtained by the Diels-Alder reaction between 1,3-diene and maleic anhydride, and then hydrating the lactone to produce an alcohol followed by (meth) acrylation of the alcohol; a polymer produced by (co) polymerizing a monomer composition comprising the (meth)acrylate of the present invention is excellent in transparency, dry etching resistance, and solubility in organic solvents, and so it is preferably used as a resin for a chemically amplified resist composition.

13 Claims, 15 Drawing Sheets

Fig. 1 $^1$H-NMR spectrum of the compound represented by the formula (7)

$^{13}$C-NMR spectrum of the compound represented by the formula (7)

$^{13}$C-NMR spectrum of the compound represented by the formula (9)

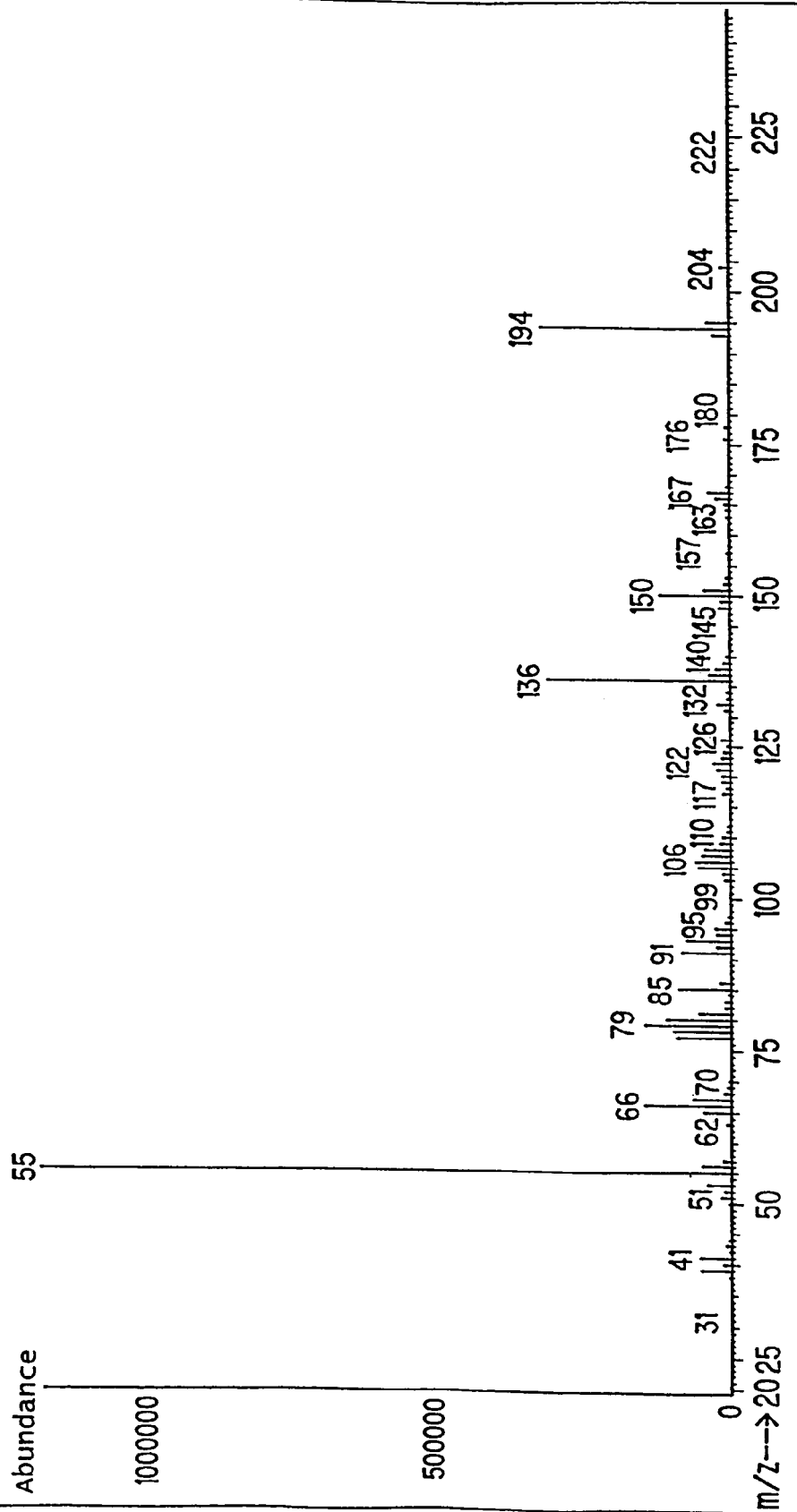

# (METH)ACRYLATE, RAW MATERIAL ALCOHOL FOR THE (METH)ACRYLATE, METHOD OF PRODUCING THE (METH)ACRYLATE AND THE ALCOHOL, POLYMER PRODUCED BY POLYMERIZING THE (METH)ACRYLATE, CHEMICALLY AMPLIFIED RESIST COMPOSITION, AND METHOD OF THE FORMATION OF A PATTERN

REFERENCE TO PRIOR APPLICATIONS

The present Application is a divisional of application Ser. No. 10/433,570, filed on Jun. 5, 2003, and now U.S. Pat. No. 7,041,838, and in which the entire contents are incorporated herein by reference. Application Ser. No. 10/433,570 is a 35 U.S.C. § 371 of International Application No. PCT/JP01/10628, filed on Dec. 5, 2001.

TECHNICAL FIELD

The present invention relates to (meth)acrylate, which is useful as a raw material monomer for component resins of a coating material, adhesive, agglutinant, resin for ink, resist or the like; a raw material alcohol for the (meth)acrylate; and a method of producing the (meth)acrylate and the alcohol. Moreover, the present invention relates to a polymer produced by polymerizing the (meth)acrylate, which is useful for resist or the like. In particular, it relates to a polymer for resist, which is preferably used in microfabrication using an excimer laser or electron beam. Further, the present invention relates to a chemically amplified resist composition comprising the polymer, and a method of the formation of a pattern.

BACKGROUND ART

A condensed cycloaliphatic compound, decahydronaphthalene, and cross-linking cycloaliphatic compounds, norbornane, tricyclodecane, tetracyclododecane, bicyclo[2.2.2]octane and adamantane, are excellent in low specific gravity, hydrophobicity, transparency, heat resistance, and environmental stability. Moreover, it is known that (meth)acrylate, which has the above condensed cycloaliphatic compound or cross-linking cycloaliphatic compound in its intramolecular structure, also has the aforementioned excellent properties. A method of synthesizing such (meth)acrylate is described, for example, in Japanese Patent Publication No. 5-27643, Japanese Patent Publication No. 7-13038, Japanese Patent Laid-Open No. 63-8355, and Jpn. J. Appl. Phys., 35, 528 (1996).

A cyclic ester, γ-butyrolactone, is transparent, highly polar and soluble in water, as well as being a good solvent for various types of organic low molecular weight compounds and polymers. Additionally, as opposed to β-propione ring, δ-valerolactone ring and ε-caprolactone ring, γ-butyrolactone ring itself has almost no polymerizing ability, and therefore it is extremely chemically stable and is also excellent in heat stability. For these reasons, it is expected that (meth)acrylate having a γ-butyrolactone ring in its molecule is also excellent in transparency, high polarity, solubility and stability. A method of synthesizing such (meth)acrylate is described, for example, in Japanese Patent Laid-Open No. 10-212283 and Japanese Patent Laid-Open No. 11-269160.

In recent years, in some cases, a (meth)acrylate polymer used for component resins of a coating material, adhesive, agglutinant, resin for ink, resist or the like, is required to have hydrophobicity, heat resistance, moderate polarity, and solubility in various organic solvents, as well as transparency and stability.

To realize these properties, there has been proposed a method of copolymerizing (meth)acrylate comprising a condensed ring structure or a cross-linking ring structure in its molecule with (meth)acrylic acid (or (meth)acrylate) having a hydrophilic functional group. For example, J. Photopolymer Science and Technology, 7 [1], 31 (1994) describes a method of copolymerizing 1-adamantyl methacrylate, t-butyl methacrylate and methacrylic acid. Proc. of SPIE, 2438, 433 (1995) describes a method of copolymerizing tricyclodecanyl acrylate, tetrahydropyranyl methacrylate and methacrylic acid. J. of Photopolymer science and Technology, 8 [4], 623 (1995) describes a method of copolymerizing isobornyl methacrylate, methyl methacrylate, t-butyl methacrylate and methacrylic acid. However, in some cases, polymers obtained by these methods have too strong hydrophobicity, or they are inferior in stability.

It can be expected that (meth)acrylate which has both a condensed ring structure or a cross-linking ring structure such as decahydronaphthalene, norbornane, tricyclodecane, tetracyclododecane, bicyclo[2.2.2]octane and adamantane, and a γ-butyrolactone structure in a molecule, has high polarity and solubility in various solvents deriving from the γ-butyrolactone structure, as well as hydrophobicity and heat resistance deriving from the condensed ring structure or the cross-linking ring structure. And the above effects can be expected even from a condensed ring structure or a cross-linking ring structure combining a simple cycloaliphatic structure such as cyclopentane and cyclohexane with the γ-butyrolactone structure.

Accordingly, Japanese Patent Laid-Open No. 2000-26446 proposes a copolymer obtained by copolymerizing 5-(meth)acryloyloxy-6-hydroxybicyclo[2.2.1]heptane-2-carboxylic-6-lactone. However, 5-(meth)acryloyloxy-6-hydroxybicyclo[2.2.1]heptane-2-carboxylic-6-lactone is a solid at an ordinary temperature and it is not always sufficiently soluble in organic solvents, so that it is not easy to produce the (co)polymer by solution polymerization.

By the way, in recent years, a microfabrication technique has quickly progressed against the backdrop of the development of a lithography technique so as to realize high-density and high-integrated devices, in the field of microfabrication technology for production of semiconductor devices or liquid crystal devices. As such a microfabrication technique, an exposure radiation source having a shorter wavelength has generally been used. Specifically, the exposure radiation source has been changed from the conventional ultraviolet ray, such as a g-line (wavelength: 438 nm) and i-line (wavelength: 365 nm), to far ultraviolet ray.

Presently, a KrF excimer laser (wavelength: 248 nm) lithography technology has been introduced in the market, and an ArF excimer laser (wavelength: 193 nm) lithography technology, which is directed towards the conversion of an exposure radiation source into the source with a further shorter wavelength, is being introduced. Moreover, an $F_2$ excimer laser (wavelength: 157 nm) lithography technology is studied as the next generation technology. Furthermore, an electron beam lithography technology, which somewhat differs from the above technologies, is also intensively studied.

As a resist with high sensitivity to such a light source with a short wavelength or electron beam, a "chemically amplified resist" has been proposed by International Business Machine (IBM) corporation, and at present, the improvement and development of this chemically amplified resist have vigorously been progressing.

By the way, a resin used for the resist is also forced to change its structure in the conversion of the light source into the one with a shorter wavelength. For example, in the KrF excimer laser lithography, polyhydroxystyrene having high transparency to the light with a wavelength of 248 nm, a hydroxy group thereof protected with an acid-dissociating solubility-inhibiting group or the like is used. However, in the ArF excimer laser lithography, the above resin cannot always be used because its transparency is insufficient to the light with a wavelength of 193 nm.

Accordingly, as a resist resin used in the ArF excimer laser lithography, an acryl resin or cycloolefin resin that is transparent to a light with a wavelength of 193 nm becomes the focus of attention. Such an acryl resin is disclosed in publications such as Japanese Patent Laid-Open No. 4-39665, Japanese Patent Laid-Open No. 10-207069 and Japanese Patent Laid-Open No. 9-090637, and such a cycloolefin resin is disclosed in publications such as Japanese Patent Laid-Open No. 10-153864 and Japanese Patent Laid-Open No. 10-207070. However, these resins are still insufficient in their performance, and further higher dry etching resistance is required.

As means providing both transparency to the light with a wavelength of 193 nm and high dry etching resistance, Japanese Patent Laid-Open No. 2000-26446 discloses a method of copolymerizing 5-(meth)acryloyloxy-6-hydroxybicyclo[2.2.1]heptane-2-carboxylic-6-lactone or the like as a monomer unit.

The thus obtained copolymer offers excellent performance as a resist resin. However, 5-(meth)acryloyloxy-6-hydroxybicyclo[2.2.1]heptane-2-carboxylic-6-lactone is a solid at an ordinary temperature and is inferior in solubility in organic solvents. Accordingly, it is extremely difficult to eliminate unreacted monomers remaining in a polymerization solution in the process of reprecipitating a resist resin synthesized by solution polymerization, and sometimes it may affect resist some kinds of performance such as transmittance. Moreover, in general, a resist resin obtained by copolymerizing 5-(meth)acryloyloxy-6-hydroxybicyclo[2.2.1]heptane-2-carboxylic-6-lactone is also inferior in solubility in organic solvents, and therefore conditions for obtaining a resist resin by solution polymerization are strictly limited.

DISCLOSURE OF THE INVENTION

It is an object of the present invention to provide a (meth)acrylate having a condensed ring structure or a cross-linking ring structure comprising a γ-butyrolactone structure in its molecule, which is excellent in heat resistance, moderate polarity, and solubility in organic solvents; a raw material alcohol for the (meth)acrylate; and a method of producing these materials which is easy to perform, has high yield, and is excellent in productivity. Moreover, it is another object of the present invention to provide a polymer having excellent transparency, high dry etching resistance, and excellent solubility in organic solvents; a chemically amplified resist composition preferably used in far ultraviolet excimer laser lithography, electron beam lithography and other lithographies; and a method of forming a pattern using the chemically amplified resist composition.

The present invention relates to a (meth)acrylate represented by the following formula (1):

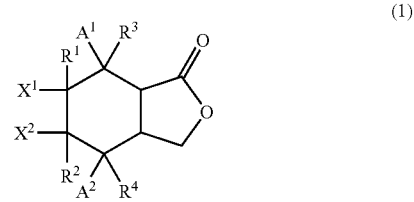

wherein each of $R^1$, $R^2$, $R^3$ and $R^4$ represents a hydrogen atom, a methyl group or an ethyl group; either one of $X^1$ or $X^2$ represents a (meth)acryloyloxy group and the other represents a hydrogen atom; both $A^1$ and $A^2$ represent hydrogen atoms, or $A^1$ and $A^2$ form —O—, —CH$_2$— or —CH$_2$CH$_2$—.

In addition, the present invention relates to an alcohol represented by the following formula (2):

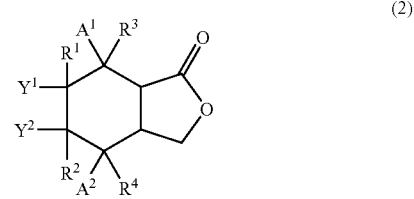

wherein each of $R^1$, $R^2$, $R^3$ and $R^4$ represents a hydrogen atom, a methyl group or an ethyl group; either one of $Y^1$ or $Y^2$ represents a hydroxy group and the other represents a hydrogen atom; both $A^1$ and $A^2$ represent hydrogen atoms, or $A^1$ and $A^2$ form —O—, —CH$_2$— or —CH$_2$CH$_2$—.

Moreover, the present invention relates to a method of producing the alcohol represented by the above formula (2), comprising the steps of:

producing a lactone represented by the following formula (4):

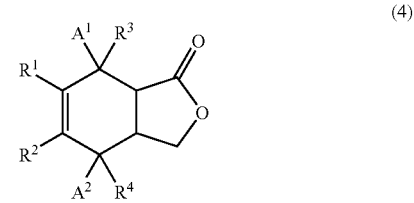

wherein each of $R^1$, $R^2$, $R^3$ and $R^4$ represents a hydrogen atom, a methyl group or an ethyl group; both $A^1$ and $A^2$ represent hydrogen atoms, or $A^1$ and $A^2$ form —O—, —CH$_2$— or —CH$_2$CH$_2$—;

by reducing an addition product represented by the following formula (3):

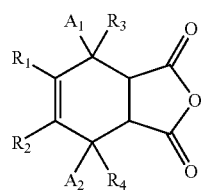

(3)

wherein each of $R^1$, $R^2$, $R^3$ and $R^4$ represents a hydrogen atom, a methyl group or an ethyl group; both $A^1$ and $A^2$ represent hydrogen atoms, or $A^1$ and $A^2$ form —O—, —$CH_2$— or —$CH_2CH_2$—;
  obtained by the Diels-Alder reaction between 1,3-diene and maleic anhydride; and
  hydrating the lactone represented by the formula (4).

Furthermore, the present invention relates to a method of producing a (meth)acrylate represented by the above formula (1) by (meth)acrylation of the alcohol represented by the above formula (2).

Still further, the present invention relates to a method of producing the (meth)acrylate represented by the above formula (1), comprising the steps of:
  producing the alcohol represented by the above formula (2) by the above-described methods; and
  (meth)acrylating the produced alcohol.

Still further, the present invention relates to a polymer produced by (co)polymerizing a monomer composition comprising the monomer represented by the above formula (1).

Still further, the present invention relates to the above-described polymer represented by the following formula (5-1):

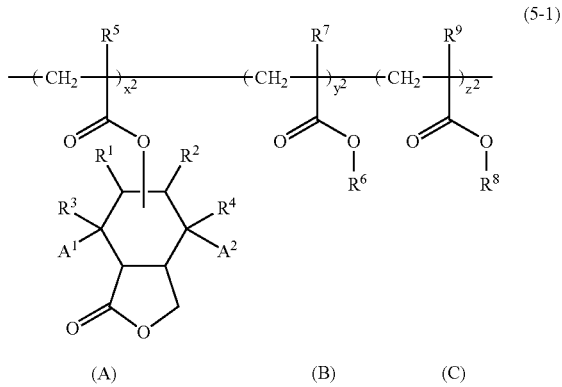

(5-1)

wherein each of $R^1$, $R^2$, $R^3$ and $R^4$ represents a hydrogen atom, a methyl group or an ethyl group; each of $R^5$, $R^7$ and $R^9$ represents a hydrogen atom or a methyl group; $R^6$ represents a cyclic hydrocarbon group having a group that is eliminated by acid; $R^8$ represents a group having a hydrophilic functional group or a hydrogen atom; both $A^1$ and $A^2$ represent hydrogen atoms, or $A^1$ and $A^2$ form —O—, —$CH_2$— or —$CH_2CH_2$—; and $x^2$, $y^2$ and $z^2$ represent the ratios of a unit (A), a unit (B) and a unit (C), respectively, wherein when $x^2+y^2+z^2=1$, $x^2$, $y^2$ and $z^2$ are any given numbers satisfying $0<x^2\leq1$, $0\leq y^2<1$, and $0\leq z^2<1$.

It should be noted that, in the polymer represented by the above formula (5-1), the units (A), (B) or (C) is not necessarily of the same type, but they may be of two or more types as long as they can be represented by the above general formula. Moreover, in the above formula (5-1), each unit can be in any sequence. Accordingly, the polymer represented by the above formula (5-1) may be either a random copolymer or a block copolymer.

Still further, the present invention relates to the above-described polymer represented by the following formula (5-2):

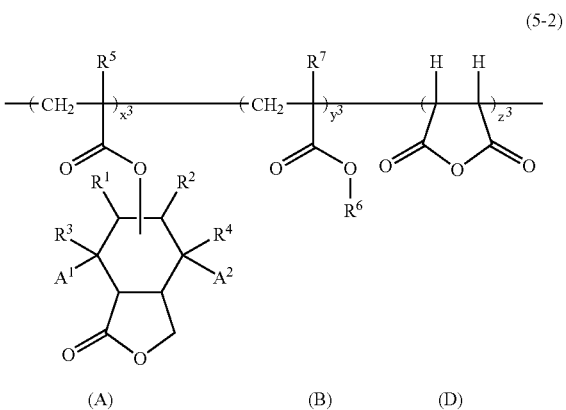

(5-2)

wherein each of $R^1$, $R^2$, $R^3$ and $R^4$ represents a hydrogen atom, a methyl group or an ethyl group; each of $R^5$ and $R^7$ represents a hydrogen atom or a methyl group; $R^6$ represents a cyclic hydrocarbon group having a group that is eliminated by acid; both $A^1$ and $A^2$ represent hydrogen atoms, or $A^1$ and $A^2$ form —O—, —$CH_2$— or —$CH_2CH_2$—; and $x^3$, $y^3$ and $z^3$ represent the ratios of a unit (A), a unit (B) and a unit (D), respectively, wherein when $x^3+y^3+z^3=1$, $x^3$, $y^3$ and $z^3$ are any given numbers satisfying $0<x^3\leq1$, $0\leq y^3<1$, and $0\leq z^3<1$.

It should be noted that, in the polymer represented by the above formula (5-2), the units (A) or (B) is not necessarily of the same type, but they may be of two or more types as long as they can be represented by the above general formula. Moreover, in the above formula (5-2), each unit can be in any sequence. Accordingly, the polymer represented by the above formula (5-2) may be either a random copolymer or a block copolymer.

Still further, the present invention relates to the above-described polymer represented by the following formula (5-3):

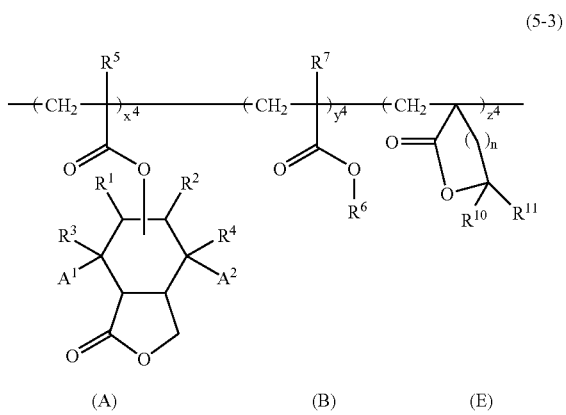

(5-3)

wherein each of $R^1$, $R^2$, $R^3$, $R^4$, $R^{10}$ and $R^{11}$ represents a hydrogen atom, a methyl group or an ethyl group; each of $R^5$ and $R^7$ represents a hydrogen atom or a methyl group; $R^6$ represents a cyclic hydrocarbon group having a group that is eliminated by acid; both $A^1$ and $A^2$ represent hydrogen atoms, or $A^1$ and $A^2$ form —O—, —CH$_2$— or —CH$_2$CH$_2$—; n represents an integer of 0 to 4; and $x^4$, $y^4$ and $z^4$ represent the ratios of a unit (A), a unit (B) and a unit (E), respectively, wherein when $x^4+y^4+z^4=1$, $x^4$, $y^4$ and $z^4$ are any given numbers satisfying $0<x^4\leq 1$, $0\leq y^4<1$, and $0\leq z^4<1$.

It should be noted that, in the polymer represented by the above formula (5-3), the units (A), (B) or (E) is not necessarily of the same type, but they may be of two or more types as long as they can be represented by the above general formula. Moreover, in the above formula (5-3), each unit can be in any sequence. Accordingly, the polymer represented by the above formula (5-3) may be either a random copolymer or a block copolymer.

Still further, the present invention relates to a chemically amplified resist composition comprising the above-described polymer and a photoacid generator.

Still further, the present invention relates to a method of forming a pattern, comprising the steps of:

coating the above-described chemically amplified resist composition onto a substrate to be processed;

exposing the substrate to a light with a wavelength of 250 nm or shorter; and developing.

The term "(meth)acrylate" is used herein to mean both "acrylate" and "methacrylate". Moreover, the term "(co) polymerization" is used herein to mean either homopolymerization or copolymerization, as it is commonly used. The term "(meth)acryloyl" is used herein to mean both "acryloyl" and "methacryloyl".

Moreover, in the units (A) of the polymers represented by the above formulas (5-1), (5-2) and (5-3), a group binding to the main chain which is a (meth)acryloyloxy group with open-chained unsaturated bonds binds to a carbon to which $R^1$ or $R^2$ binds.

BRIEF DESCRIPTION OF THE DRAWINGS

FIG. 15 is an MS -spectrum (4) of each ingredient of the compound represented by the formula (9), which was obtained in Example A3.

BEST MODE FOR CARRYING OUT THE INVENTION

Figure 1:
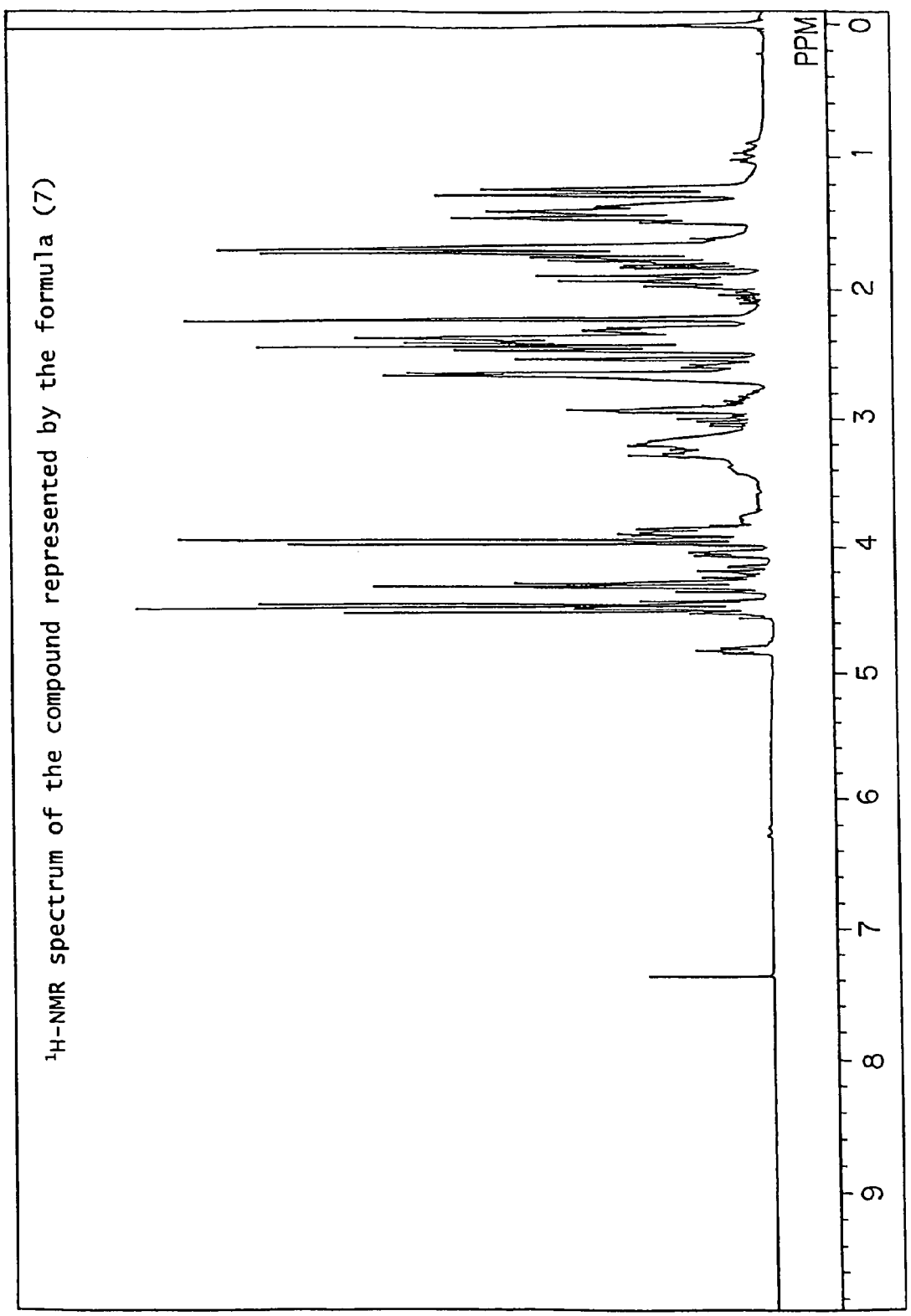
FIG. 1 is a $^1$H-NMR spectrum of the compound represented by a formula (7), which was obtained in Example A1.

The (meth)acrylate of the present invention is a (meth) acrylate represented by the following formula (1) (hereinafter referred to also as an ester of formula (1)). The (meth)acrylate of the present invention may be a mixture of two or more types of (meth)acrylates represented by the following formula (1):

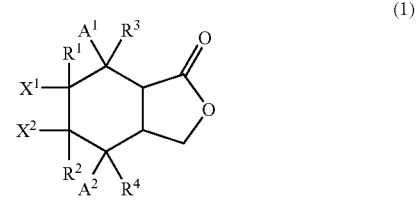

wherein each of $R^1$, $R^2$, $R^3$ and $R^4$ represents a hydrogen atom or a methyl group; either one of $X^1$ or $X^2$ represents a (meth)acryloyloxy group and the other represents a hydrogen atom; both $A^1$ and $A^2$ represent hydrogen atoms, or $A^1$ and $A^2$ form —O—, —CH$_2$— or —CH$_2$CH$_2$—.

The (meth)acrylate of the present invention is a novel compound, which has a condensed ring structure or a cross-linking ring structure, and a γ-butyrolactone structure in a single molecule, and it has heat resistance, moderate polarity, and excellent solubility in organic solvents. Accordingly, the (meth)acrylate of the present invention is extremely useful as a raw material monomer for a (meth) acrylate polymer used for component resins of a coating material, adhesive, agglutinant, resin for ink, resist, or the like.

The (meth)acrylate of the present invention is obtained by (meth)acrylation of an alcohol of the present invention represented by the following formula (2) (hereinafter referred to also as an alcohol of formula (2)):

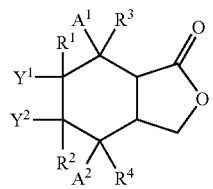

(2)

wherein each of $R^1$, $R^2$, $R^3$ and $R^4$ represents a hydrogen atom, a methyl group or an ethyl group; either one of $Y^1$ or $Y^2$ represents a hydroxy group and the other represents a hydrogen atom; both $A^1$ and $A^2$ represent hydrogen atoms, or $A^1$ and $A^2$ form —O—, —CH$_2$— or —CH$_2$CH$_2$—.

Each of $R^1$, $R^2$, $R^3$, $R^4$, $A^1$, $A^2$, and $Y^1$ or $Y^2$ that is a hydrogen atom in the formula (2) corresponds to each of $R^1$, $R^2$, $R^3$, $R^4$, $A^1$, $A^2$, and $X^1$ or $X^2$ that is a hydrogen atom in the formula (1). A (meth)acryloyloxy group is obtained by (meth)acrylation of a hydroxy group of $Y^1$ or $Y^2$ in the formula (2), so as to obtain the (meth)acrylate represented by the above formula (1).

The alcohol of the present invention represented by the above formula (2) is obtained by producing a lactone represented by the above formula (4) by reducing an addition product represented by the above formula (3) obtained by the Diels-Alder reaction between 1,3-diene and maleic anhydride, and then hydrating the obtained lactone.

According to the present invention, the alcohol represented by the above formula (2) can be produced in an extremely short process from an addition product obtained by the Diels-Alder reaction between 1,3-diene and maleic anhydride that are easily obtained. Moreover, the (meth) acrylate represented by the above formula (1) can easily be produced from the thus obtained alcohol represented by the above formula (2).

In general, as a method for obtaining a lactone from an acid anhydride, a method of reducing the acid anhydride using hydride reducing agents is widely known. For example, J. Org. Chem., 35, 3574 (1970) describes a method of synthesizing a lactone compound by applying sodium boron hydride as a reducing agent to various types of cyclic acid anhydride in a THF or DMF solvent. Synthesis, 42 (1974) describes a method of synthesizing γ-crotonolactone, which comprises reducing a cyclic acid anhydride obtained by the Diels-Alder reaction between furan and maleic anhydride with sodium boron hydride in an ethanol solvent, so as to obtain the corresponding lactone. As a method of isolating lactone, the above-described document, J. Org. Chem., 35, 3574 (1970) describes a method which comprises neutralizing the reaction solution obtained by reduction with a hydrochloric acid solution, and then extracting with ether followed by condensation.

However, where an addition product from the Diels-Alder reaction between 1,3-diene and maleic anhydride is reduced using a hydride reducing agent, if it is carried out in a tetrahydrofuran solvent, the addition product has low solubility in the solvent and the reaction is carried out in a suspension state, and so a long time may be required to complete the reaction. In order to accelerate the reaction, a large amount of expensive reducing agents should be used, and it is not economically preferable. Moreover, since common reducing agents such as sodium boron hydride have low solubility in tetrahydrofuran, a long time may be required to complete the reaction. On the other hand, where aprotic polar solvents such as DMF are used, an addition product from the Diels-Alder reaction between 1,3-diene and maleic anhydride, and common reducing agents such as sodium boron hydride are highly soluble therein, and the reaction quickly progresses even using a small amount of reducing agents. However, a lactone obtained by the reduction is highly soluble in aprotic polar solvents. Therefore, if the lactone is isolated by a method of neutralizing the reaction solution, extracting with ether and condensing it, aprotic polar solvents are very likely to coexist until the end, and the lactone can hardly be isolated in some cases. To eliminate aprotic solvents, in some cases, much time and efforts are required to wash them with a large amount of solvents and water many times, and further, isolation yield significantly decreases.

In the present invention, an aprotic polar solvent is used when an addition product from the Diels-Alder reaction is reduced, and the obtained lactone is extracted with an extraction solvent, preferably a ketone solvent, and then the extract is directly used in the following reaction without isolation of the lactone. Thus, the present invention solves the above problems, and it provides a highly productive method of producing the (meth)acrylate of the present invention, and a raw material alcohol for the (meth)acrylate.

The polymer of the present invention is obtained by (co)polymerizing a monomer composition comprising the monomer represented by the above formula (1). It comprises a monomeric unit wherein unsaturated bond of the monomer represented by the above formula (1) is open-chained (transfer of electrons). The monomer represented by the above formula (1) may be a single type or a mixture of two or more types.

The monomer represented by the above formula (1) has a condensed ring structure or a cross-linking ring structure and a γ-butyrolactone structure in a single molecule. Accordingly, the polymer of the present. Invention has excellent transparency to far ultraviolet light, high dry etching resistance deriving from the condensed ring structure or the cross-linking ring structure, and excellent solubility in organic solvents deriving from an exposed γ-butyrolactone structure. The polymer of the present invention is particularly preferable as a resist resin used in far ultraviolet excimer laser lithography, electron beam lithography, and other lithographies.

The present invention will be described in detail below.

1. (Meth)acrylate of the Present Invention

First, the (meth)acrylate of the present invention represented by the above formula (1) will be explained.

In the formula (1), each of $R^1$, $R^2$, $R^3$ and $R^4$ independently represents a hydrogen atom, a methyl group or an ethyl group, and it is preferably a hydrogen atom or a methyl group. The number of methyl and ethyl groups may be any of 0 to 4, and it is preferably 0 to 2. when it is used as a raw material monomer for a chemically amplified resist composition, the number of methyl and ethyl groups is particularly preferably 0 or 1.

Either one of $X^1$ or $X^2$ represents a (meth)acryloyloxy group, and the other represents a hydrogen atom. In the (meth)acrylate of the present invention, any of $X^1$ or $X^2$ may represent a (meth)acryloyloxy group.

Both $A^1$ and $A^2$ represent hydrogen atoms, or $A^1$ and $A^2$ form —O—, —CH$_2$— or —CH$_2$CH$_2$—. Among them, so as to obtain excellent heat resistance, it is preferable that $A^1$ and $A^2$ form —O—, —CH$_2$— or —CH$_2$CH$_2$—, and it is particularly preferable that $A^1$ and $A^2$ form —CH$_2$—.

Specific examples of the ester of the formula (1) are as follows:

7-Acryloyloxy-3-oxabicyclo[4.3.0]nonane-2-one and 8-acryloyloxy-3-oxabicyclo[4.3.0]nonane-2-one, and their mixture, 7-acryloyloxy-7-methyl-3-oxabicyclo[4.3.0]nonane-2-one, 7-acryloyloxy-8-methyl-3-oxabicyclo[4.3.0]nonane-2-one, 8-acryloyloxy-7-methyl-3-oxabicyclo[4.3.0]nonane-2-one and 8-acryloyloxy-8-methyl-3-oxabicyclo[4.3.0]nonane-2-one, and their mixture, 7-acryloyloxy-6-methyl-3-oxabicyclo[4.3.0]nonane-2-one, 7-acryloyloxy-9-methyl-3-oxabicyclo[4.3.0]nonane-2-one, 8-acryloyloxy-6-methyl-3-oxabicyclo[4.3.0]nonane-2-one and 8-acryloyloxy-9-methyl-3-oxabicyclo[4.3.0]nonane-2-one, and their mixture, 7,8-dimethyl-7-acryloyloxy-3-oxabicyclo[4.3.0]nonane-2-one and 7,8-dimethyl-8-acryloyloxy-3-oxabicyclo[4.3.0]nonane-2-one, and their mixture, 8-acryloyloxy-4-oxatricyclo[$5.2.1.0^{2,6}$]decane-3-one and 9-acryloyloxy-4-oxatricyclo[$5.2.1.0^{2,6}$]decane-3-one, and their mixture, 8-acryloyloxy-7-methyl-4-oxatricyclo[$5.2.1.0^{2,6}$]decane-3-one, 8-acryloyloxy-8-methyl-4-oxatricyclo[$5.2.1.0^{2,6}$]decane-3-one, 8-acryloyloxy-9-methyl-4-oxatricyclo[$5.2.1.0^{2,6}$]decane-3-one, 8-acryloyloxy-1-methyl-4-oxatricyclo[$5.2.1.0^{2,6}$]decane-3-one, 8-acryloyloxy-10-methyl-4-oxatricyclo[$5.2.1.0^{2,6}$]decane-3-one, 9-acryloyloxy-7-methyl-4-oxatricyclo[$5.2.1.0^{2,6}$]decane-3-one, 9-acryloyloxy-8-methyl-4-oxatricyclo[$5.2.1.0^{2,6}$]decane-3-one, 9-acryloyloxy-9-methyl-4-oxatricyclo[$5.2.1.0^{2,6}$]decane-3-one, 9-acryloyloxy-1-methyl-4-oxatricyclo[$5.2.1.0^{2,6}$]decane-3-one and 9-acryloyloxy-10-methyl-4-oxatricyclo[$5.2.1.0^{2,6}$]decane-3-one, and their mixture, 8-acryloyloxy-4-oxatricyclo[$5.2.2.0^{2,6}$]undecane-3-one and 9-acryloyloxy-4-oxatricyclo[$5.2.2.0^{2,6}$]undecane-3-one, and their mixture, 8-acryloyloxy-7-ethyl-4-oxatricyclo[$5.2.1.0^{2,6}$]decane-3-one, 8-acryloyloxy-8-ethyl-4-oxatricyclo[$5.2.1.0^{2,6}$]decane-3-one, 8-acryloyloxy-9-ethyl-4-oxatricyclo[$5.2.1.0^{2,6}$]decane-3-one, 8-acryloyloxy-1-ethyl-4-oxatricyclo[$5.2.1.0^{2,6}$]decane-3-one, 8-acryloyloxy-10-ethyl-4-oxatricyclo[$5.2.1.0^{2,6}$]decane-3-one, 9-acryloyloxy-7-ethyl-4-oxatricyclo[$5.2.1.0^{2,6}$]decane-3-one, 9-acryloyloxy-8-ethyl-4-oxatricyclo[$5.2.1.0^{2,6}$]decane-3-one, 9-acryloyloxy-9-ethyl-4-oxatricyclo[$5.2.1.0^{2,6}$]decane-3-one, 9-acryloyloxy-1-ethyl-4-oxatricyclo[$5.2.1.0^{2,6}$]decane-3-one and 9-acryloyloxy-10-ethyl-4-oxatricyclo[$5.2.1.0^{2,6}$]decane-3-one, and their mixture, 8-acryloyloxy-4,10-dioxatricyclo[$5.2.1.0^{2,6}$]decane-3-one and 9-acryloyloxy-4,10-dioxatricyclo[$5.2.1.0^{2,6}$]decane-3-one, and their mixture, 8-acryloyloxy-1-methyl-4,10-dioxatricyclo[$5.2.1.0^{2,6}$]decane-3-one, 8-acryloyloxy-7-methyl-4,10-dioxatricyclo[$5.2.1.0^{2,6}$]decane-3-one, 9-acryloyloxy-1-methyl-4,10-dioxatricyclo[$5.2.1.0^{2,6}$]decane-3-one and 9-acryloyloxy-7-methyl-4,10-dioxatricyclo[$5.2.1.0^{2,6}$]decane-3-one, and their mixture, 7-methacryloyloxy-3-oxabicyclo[4.3.0]nonane-2-one and 8-methacryloyloxy-3-oxabicyclo[4.3.0]nonane-2-one, and their mixture, 7-methacryloyloxy-7-methyl-3-oxabicyclo[4.3.0]nonane-2-one, 7-methacryloyloxy-8-methyl-3-oxabicyclo[4.3.0]nonane-2-one, 8-methacryloyloxy-7-methyl-3-oxabicyclo[4.3.0]nonane-2-one and 8-methacryloyloxy-8-methyl-3-oxabicyclo[4.3.0]nonane-2-one, and their mixture, 7-methacryloyloxy-6-methyl-3-oxabicyclo[4.3.0]nonane-2-one, 7-methacryloyloxy-9-methyl-3-oxabicyclo[4.3.0]nonane-2-one, 8-methacryloyloxy-6-methyl-3-oxabicyclo[4.3.0]nonane-2-one and 8-methacryloyloxy-9-methyl-3-oxabicyclo[4.3.0]nonane-2-one, and their mixture, 7,8-dimethyl-7-methacryloyloxy-3-oxabicyclo[4.3.0]nonane-2-one and 7,8-dimethyl-8-methacryloyloxy-3-oxabicyclo[4.3.0]nonane-2-one, and their mixture, 8-methacryloyloxy-4-oxatricyclo[$5.2.1.0^{2,6}$]decane-3-one and 9-methacryloyloxy-4-oxatricyclo[$5.2.1.0^{2,6}$]decane-3-one, and their mixture, 8-methacryloyloxy-7-methyl-4-oxatricyclo[$5.2.1.0^{2,6}$]decane-3-one, 8-methacryloyloxy-8-methyl-4-oxatricyclo[$5.2.1.0^{2,6}$]decane-3-one, 8-methacryloyloxy-9-methyl-4-oxatricyclo[$5.2.1.0^{2,6}$]decane-3-one, 8-methacryloyloxy-1-methyl-4-oxatricyclo[$5.2.1.0^{2,6}$]decane-3-one, 8-methacryloyloxy-10-methyl-4-oxatricyclo[$5.2.1.0^{2,6}$]decane-3-one, 9-methacryloyloxy-7-methyl-4-oxatricyclo[$5.2.1.0^{2,6}$]decane-3-one, 9-methacryloyloxy-8-methyl-4-oxatricyclo[$5.2.1.0^{2,6}$]decane-3-one, 9-methacryloyloxy-9-methyl-4-oxatricyclo[$5.2.1.0^{2,6}$]decane-3-one, 9-methacryloyloxy-1-methyl-4-oxatricyclo[$5.2.1.0^{2,6}$]decane-3-one and 9-methacryloyloxy-10-methyl-4-oxatricyclo[$5.2.1.0^{2,6}$]decane-3-one, and their mixture, 8-methacryloyloxy-7-ethyl-4-oxatricyclo[$5.2.1.0^{2,6}$]decane-3-one, 8-methacryloyloxy-8-ethyl-4-oxatricyclo[$5.2.1.0^{2,6}$]decane-3-one, 8-methacryloyloxy-9-ethyl-4-oxatricyclo[$5.2.1.0^{2,6}$]decane-3-one, 8-methacryloyloxy-1-ethyl-4-oxatricyclo[$5.2.1.0^{2,6}$]decane-3-one, 8-methacryloyloxy-10-ethyl-4-oxatricyclo[$5.2.1.0^{2,6}$]decane-3-one, 9-methacryloyloxy-7-ethyl-4-oxatricyclo[$5.2.1.0^{2,6}$]decane-3-one, 9-methacryloyloxy-8-ethyl-4-oxatricyclo[$5.2.1.0^{2,6}$]decane-3-one, 9-methacryloyloxy-9-ethyl-4-oxatricyclo[$5.2.1.0^{2,6}$]decane-3-one, 9-methacryloyloxy-1-ethyl-4-oxatricyclo[$5.2.1.0^{2,6}$]decane-3-one and 9-methacryloyloxy-10-ethyl-4-oxatricyclo[$5.2.1.0^{2,6}$]decane-3-one, and their mixture, 8-methacryloyloxy-4-oxatricyclo[$5.2.2.0^{2,6}$]undecane-3-one and 9-methacryloyloxy-4-oxatricyclo[$5.2.2.0^{2,6}$]undecane-3-one, and their mixture, 8-methacryloyloxy-4,10-dioxatricyclo[$5.2.1.0^{2,6}$]decane-3-one and 9-methacryloyloxy-4,10-dioxatricyclo[$5.2.1.0^{2,6}$]decane-3-one, and their mixture, 8-methacryloyloxy-1-methyl-4,10-dioxatricyclo[$5.2.1.0^{2,6}$]decane-3-one, 8-methacryloyloxy-7-methyl-4,10-dioxatricyclo[$5.2.1.0^{2,6}$]decane-3-one, 9-methacryloyloxy-1-methyl-4,10-dioxatricyclo[$5.2.1.0^{2,6}$]decane-3-one and 9-methacryloyloxy-7-methyl-4,10-dioxatricyclo[$5.2.1.0^{2,6}$]decane-3-one, and their mixture, or the like.

Note that 7-acryloyloxy-7-methyl-3-oxabicyclo[4.3.0]nonane-2-one, 8-acryloyloxy-8-methyl-3-oxabicyclo[4.3.0]nonane-2-one, 7,8-dimethyl-7-acryloyloxy-3-oxabicyclo[4.3.0]nonane-2-one, 7,8-dimethyl-8-acryloyloxy-3-oxabicyclo[4.3.0]nonane-2-one, 8-acryloyloxy-8-methyl-4-oxatricyclo[$5.2.1.0^{2,6}$]decane-3-one, 9-acryloyloxy-9-methyl-4-oxatricyclo[$5.2.1.0^{2,6}$]decane-3-one, 8-acryloyloxy-8-ethyl-4-oxatricyclo[$5.2.1.0^{2,6}$]decane-3-one, 9-acryloyloxy-9-ethyl-4-oxatricyclo[$5.2.1.0^{2,6}$]decane-3-one, 7-methacryloyloxy-7-methyl-3-oxabicyclo[4.3.0]nonane-2-one, 8-methacryloyloxy-8-methyl-3-oxabicyclo[4.3.0]nonane-2-one, 7,8-dimethyl-7-methacryloyloxy-3-oxabicyclo[4.3.0]nonane-2-one, 7,8-dimethyl-8-methacryloyloxy-3-oxabicyclo[4.3.0]nonane-2-one, 8-methacryloyloxy-8-methyl-4-oxatricyclo[$5.2.1.0^{2,6}$]decane-3-one, 9-methacryloyloxy-9-methyl-4-oxatricyclo[$5.2.1.0^{2,6}$]decane-3-one, 8-methacryloyloxy-8-ethyl-4-oxatricyclo[$5.2.1.0^{2,6}$]decane-3-one, 9-methacryloyloxy-9-ethyl-4-oxatricyclo[$5.2.1.0^{2,6}$]decane-3-one are stable under neutral conditions. However, these compounds are the (meth)acrylates of tertiary alcohol, and so they are so-called potential carboxy monomers in which alcohol residues are easily eliminated by the action of acid so as to generate carboxy groups. Accordingly, these are expected as raw material monomers for a chemically amplified resist resin.

2. Alcohol of the Present Invention

Now, an alcohol of the present invention represented by the above formula (2), which is a raw material for the (meth)acrylate of the present invention represented by the above formula (1), will be explained.

In the formula (2), each of $R^1$, $R^2$, $R^3$ and $R^4$ represents a hydrogen atom, a methyl group or an ethyl group, and either one of $Y^1$ or $Y^2$ represents a hydroxy group and the other represents a hydrogen atom. Both $A^1$ and $A^2$ represent hydrogen atoms, or $A^1$ and $A^2$ form —O—, —$CH_2$— or —$CH_2CH_2$—.

As stated above, each of $R^1$, $R^2$, $R^3$, $R^4$, $A^1$, $A^2$, and $Y^1$ or $Y^2$ that is a hydrogen atom in the formula (2) corresponds to each of $R^1$, $R^2$, $R^3$, $R^4$, $A^1$, $A^2$, and $X^1$ or $X^2$ that is a hydrogen atom in the formula (1). A (meth)acryloyloxy group of $X^1$ or $X^2$ in the formula (1) is obtained by (meth)acrylation of a hydroxy group of $Y^1$ or $Y^2$ in the formula (2). Consequently, $R^1$, $R^2$, $R^3$, $R^4$, $A^1$ and $A^2$ in the formula (2) are the same as $R^1$, $R^2$, $R^3$, $R^4$, $A^1$ and $A^2$ in the formula (1), and their preferred examples are also the same.

Specific examples of the alcohol of the formula (2) are as follows:

7-hydroxy-3-oxabicyclo[4.3.0]nonane-2-one and 8-hydroxy-3-oxabicyclo[4.3.0]nonane-2-one, and their mixture, 7-hydroxy-7-methyl-3-oxabicyclo[4.3.0]nonane-2-one, 7-hydroxy-8-methyl-3-oxabicyclo[4.3.0]nonane-2-one, 8-hydroxy-7-methyl-3-oxabicyclo[4.3.0]nonane-2-one and 8-hydroxy-8-methyl-3-oxabicyclo[4.3.0]nonane-2-one, and their mixture, 7-hydroxy-6-methyl-3-oxabicyclo[4.3.0]nonane-2-one, 7-hydroxy-9-methyl-3-oxabicyclo[4.3.0]nonane-2-one, 8-hydroxy-6-methyl-3-oxabicyclo[4.3.0]nonane-2-one and 8-hydroxy-9-methyl-3-oxabicyclo[4.3.0]nonane-2-one, and their mixture, 7,8-dimethyl-7-hydroxy-3-oxabicyclo[4.3.0]nonane-2-one and 7,8-dimethyl-8-hydroxy-3-oxabicyclo[4.3.0]nonane-2-one, and their mixture, 8-hydroxy-4-oxatricyclo[5.2.1.0$^{2,6}$]decane-3-one and 9-hydroxy-4-oxatricyclo[5.2.1.0$^{2,6}$]decane-3-one, and their mixture, 8-hydroxy-7-methyl-4-oxatricyclo[5.2.1.0$^{2,6}$]decane-3-one, 8-hydroxy-8-methyl-4-oxatricyclo[5.2.1.0$^{2,6}$]decane-3-one, 8-hydroxy-9-methyl-4-oxatricyclo[5.2.1.0$^{2,6}$]decane-3-one, 8-hydroxy-1-methyl-4-oxatricyclo[5.2.1.0$^{2,6}$]decane-3-one, 8-hydroxy-10-methyl-4-oxatricyclo[5.2.1.0$^{2,6}$]decane-3-one, 9-hydroxy-7-methyl-4-oxatricyclo[5.2.1.0$^{2,6}$]decane-3-one, 9-hydroxy-8-methyl-4-oxatricyclo[5.2.1.0$^{2,6}$]decane-3-one, 9-hydroxy-9-methyl-4-oxatricyclo[5.2.1.0$^{2,6}$]decane-3-one, 9-hydroxy-1-methyl-4-oxatricyclo[5.2.1.0$^{2,6}$]decane-3-one and 9-hydroxy-10-methyl-4-oxatricyclo[5.2.1.0$^{2,6}$]decane-3-one, and their mixture, 8-hydroxy-7-ethyl-4-oxatricyclo[5.2.1.0$^{2,6}$]decane-3-one, 8-hydroxy-8-ethyl-4-oxatricyclo[5.2.1.0$^{2,6}$]decane-3-one, 8-hydroxy-9-ethyl-4-oxatricyclo[5.2.1.0$^{2,6}$]decane-3-one, 8-hydroxy-1-ethyl-4-oxatricyclo[5.2.1.0$^{2,6}$]decane-3-one, 8-hydroxy-10-ethyl-4-oxatricyclo[5.2.1.0$^{2,6}$]decane-3-one, 9-hydroxy-7-ethyl-4-oxatricyclo[5.2.1.0$^{2,6}$]decane-3-one, 9-hydroxy-8-ethyl-4-oxatricyclo[5.2.1.0$^{2,6}$]decane-3-one, 9-hydroxy-9-ethyl-4-oxatricyclo[5.2.1.0$^{2,6}$]decane-3-one, 9-hydroxy-1-ethyl-4-oxatricyclo[5.2.1.0$^{2,6}$]decane-3-one and 9-hydroxy-10-ethyl-4-oxatricyclo[5.2.1.0$^{2,6}$]decane-3-one, and their mixture, 8-hydroxy-4-oxatricyclo[5.2.2.0$^{2,6}$]undecane-3-one and 9-hydroxy-4-oxatricyclo[5.2.2.0$^{2,6}$]undecane-3-one, and their mixture, 8-hydroxy-4,10-dioxatricyclo[5.2.1.0$^{2,6}$]decane-3-one and 9-hydroxy-4,10-dioxatricyclo[5.2.1.0$^{2,6}$]decane-3-one, and their mixture, 8-hydroxy-1-methyl-4,10-dioxatricyclo[5.2.1.0$^{2,6}$]decane-3-one, 8-hydroxy-7-methyl-4,10-dioxatricyclo[5.2.1.0$^{2,6}$]decane-3-one, 9-hydroxy-1-methyl-4,10-dioxatricyclo[5.2.1.0$^{2,6}$]decane-3-one and 9-hydroxy-7-methyl-4,10-dioxatricyclo[5.2.1.0$^{2,6}$]decane-3-one, and their mixture, or the like.

3. Methods of Producing the Alcohol of the Present Invention and the (Meth)acrylate of the Present Invention Now, methods of producing the alcohol of the present invention represented by the above formula (2) and the (meth)acrylate of the present invention represented by the above formula (1) will be explained.

The alcohol of the formula (2) can be produced by reducing an addition product from the Diels-Alder reaction between 1,3-diene such as (methyl-)5-norbornene-2,3-dicarboxylic anhydride and maleic anhydride, and then hydrating the obtained product.

More specifically, an addition product represented by the following formula (3) (hereinafter referred to as the compound of formula (3)) obtained by the Diels-Alder reaction between 1,3-diene and maleic anhydride is selectively reduced to obtain an olefin lactone represented by the following formula (4) (hereinafter referred to as the compound of formula (4)).

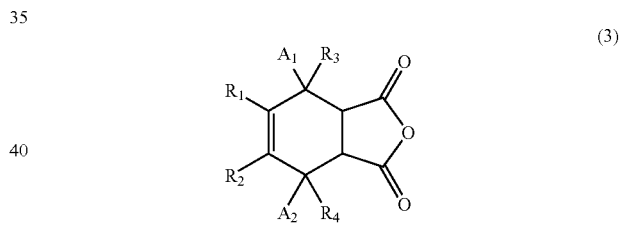

(3)

wherein each of $R^1$, $R^2$, $R^3$ and $R^4$ represents a hydrogen atom, a methyl group or an ethyl group; and both $A^1$ and $A^2$ represent hydrogen atoms, or $A^1$ and $A^2$ form —O—, —$CH_2$— or —$CH_2CH_2$—.

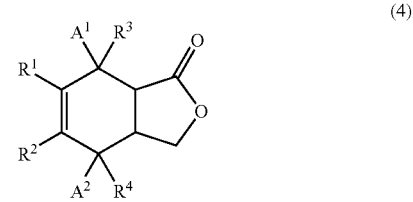

(4)

wherein each of $R^1$, $R^2$, $R^3$ and $R^4$ represents a hydrogen atom, a methyl group or an ethyl group; and both $A^1$ and $A^2$ represent hydrogen atoms, or $A^1$ and $A^2$ form —O—, —$CH_2$— or —$CH_2CH_2$—.

$R^1$, $R^2$, $R^3$, $R^4$, $A^1$ and $A^2$ in formulas (3) and (4) correspond to $R^1$, $R^2$, $R^3$, $R^4$, $A^1$ and $A^2$ in formulas (1) and (2), respectively.

The compound of formula (3) can be synthesized by the Diels-Alder reaction between 1,3-diene and maleic anhydride. Examples of 1,3-diene include 1,3-butadiene, isoprene, piperylene, 2,3-dimethyl-1,3-butadiene, cyclopentadiene, methylcyclopentadiene, ethylcyclopentadiene, 1,3-cyclohexadiene, furan and 2-methylfuran. 1,3-Diene used herein may be determined, as appropriate, depending on a product of interest.

The Diels-Alder reaction between 1,3-diene and maleic anhydride is generally carried out in a pressure-resistant hermetically sealed container such as an autoclave, using an aromatic hydrocarbon solvent such as benzene, toluene and xylene, while raising temperature. Since maleic anhydride has an extremely high activity as dienophile, as described in J. Org. Chem., 84, 297 (1962), J. Am. Chem. Soc., 102, 7816 (1980), and J. Am. Chem. Soc., 110, 5613 (1988), if a polar solvent such as water, methanol, dimethoxyethane, ethyl acetate, acetonitrile, formamide and N,N-dimethylformamide is used, the reaction can also be carried out in an open system at 0° C. to room temperature.

Moreover, a commercially available product may be used as an addition product from the Diels-Alder reaction between 1,3-diene and maleic anhydride.

A method of selectively reducing the compound of formula (3) (acid anhydride) that is an addition product from the Diels-Alder reaction between 1,3-diene and maleic anhydride to the compound of formula (4) in the presence of a carbon-carbon double bond is not particularly limited. In general, the reaction may be carried out using a metallic hydride or a metal-hydrogen complex compound as a reducing agent.

Examples of such a metallic hydride or a metal-hydrogen complex compound include borane dimethyl sulfide, diisobutyl aluminum hydride, sodium boron hydride, lithium boron hydride, potassium boron hydride, zinc boron hydride, tri-s-butyl lithium boron hydride, tri-s-butyl potassium boron hydride, triethyl lithium boron hydride, lithium aluminum hydride, tri-t-butoxy lithium aluminum hydride, and bis(methoxyethoxy)sodium aluminum hydride. The metallic hydride or the metal-hydrogen complex compound as a reducing agent may be used singly or in combination of two or more types. Among them, the use of sodium boron hydride is particularly preferable because it can easily be obtained and handled, and the reaction conditions are moderate.

The amount of the metallic hydride or the metal-hydrogen complex compound as a reducing agent should be controlled, so as to prevent the situation in which the reaction excessively progresses and even diol is reduced. In the case of sodium boron hydride, the amount used is preferably 0.5 mol or more based on 1 mol of the compound of formula (3), and it is preferably 1.5 mol or less based on 1 mol of the compound (3).

The reaction temperature of reduction with sodium boron hydride is preferably −20° C. or higher, particularly preferably 0° C. or higher to obtain a sufficient reaction rate, and it is also preferably 60° C. or lower, particularly preferably 40° C. or lower to sufficiently control the heat generated as a result of the reaction. In the case of using other reducing agents, in general, the reaction temperature is also preferably within the above range.

Examples of a solvent for a reduction reaction using a metallic hydride and/or a metal-hydrogen complex compound include alcohol solvents such as methanol and ethanol, ether solvents such as diethyl ether, tetrahydrofuran, dimethoxyethane, diglime and triglime, ester solvents such as ethyl acetate and γ-butyrolactone, nitrile solvents such as acetonitrile, amide solvents such as N,N-dimethylformamide (DMF), N,N-dimethylacetamide and N-methylpyrrolidone, hydrocarbon solvents such as toluene and hexane, and dimethyl sulfoxide. These solvents may be used singly or as a mixture of two or more types. Of these, diglime, N,N-dimethylformamide (DMF), N,N-dimethylacetamide and N-methylpyrrolidone are preferable, because these have a high reaction rate, and reducing agents such as sodium boron hydride and the compound of formula (3) are highly soluble therein. Further, diglime, N,N-dimethylacetamide and N-methylpyrrolidone are particularly preferable because these are excellent also in safety.

When sodium boron hydride is allowed to act on the compound of formula (3), the acid anhydride structure is converted into the boron complex of hydroxycarboxylic acid. Water is added to the reaction solution, if necessary, and then acid is added thereto for neutralization, and preferably, acid is further added thereto for acidification and lactonization to obtain the compound of formula (4). Herein, it is generally preferable to set the pH of the solution at about 2 to 7.

Examples of acid used to neutralize and then acidify the reaction solution include common mineral acids such as hydrochloric acid, sulfuric acid, nitric acid and phosphoric acid, and acidic ion exchange resins. These acids may be used singly or in combination of two or more types. If taking into consideration the following process of eliminating acid, of these, hydrochloric acid or acidic ion exchange resins are preferably used, and if taking into consideration handling in mass synthesis, sulfuric acid is preferably used.

As stated above, if a polar solvent is used, the Diels-Alder reaction using maleic anhydride as dienophile can be carried out in an open system at 0° C. to room temperature. Accordingly, a suitable polar solvent is selected, the Diels-Alder reaction is carried out using the solvent, and the reaction solution is reduced by adding a reducing agent such as sodium boron hydride followed by lactonization under neutral or acidic conditions, so that the compound of formula (4) can be obtained. In this case, it is not necessary to isolate and purify the obtained compound of formula (3), and therefore the operations of the Diels-Alder reaction and the reduction reaction can extremely simply be carried out successively.

The thus obtained compound of formula (4) can directly be used in the following reaction without subjecting to purification. However, purification may be carried out using silica gel column chromatography or precision distillation.

When lower carboxylic acid is added to the compound of formula (4) followed by hydrolysis to produce an alcohol, it is preferable in terms of productivity that the compound of formula (4) is extracted with an extraction solvent and that the obtained extract is then directly subjected to the following reaction to add lower carboxylic acid, without isolating the compound of formula (4) from the extract.

Examples of an extraction solvent used in extraction of the compound of formula (4) include ethers such as dimethyl ether, methyl-tert-butyl ether and diisopropyl ether, ketones such as methyl-n-propyl ketone, methyl-n-butyl ketone and methyl-isobutyl ketone (hereinafter referred to as MIBK), aromatic hydrocarbons such as toluene and xylene, esters such as ethyl acetate. These solvents may be used singly or as a mixture of two or more types. When emphasis is placed on recovery rate and separativity of two liquid phases, ketones, in particular, MIBK is preferably used.

The amount of an extraction solvent used is not particularly limited. It is preferably 0.05 or more times to the amount of an extraction feed by weight, and it is also preferably 20 or less times to the amount of an extraction feed by weight.

Extraction may be carried out only once, or it may also be carried out twice or more. The extracted layer may be washed with water.

In the present invention, the extract can directly be subjected to the following lower carboxylic acid addition reaction without isolating the compound of formula (4) therefrom, but it may also be possible to eliminate solvents by distillation so as to concentrate the extract.

In terms of tank efficiency, the concentration of the compound of formula (4) in the extract that is concentrated if necessary and subjected to the lower carboxylic acid addition reaction is preferably 1% or more by weight, and particularly preferably 25% or more by weight to the total mass. Moreover, in terms of prevention of the excessive reaction, the concentration of the compound of formula (4) in the extract is preferably 95% or less by weight, and particularly preferably 70% or less by weight to the total mass.

Needless to say, it may also be possible to isolate the compound of formula (4) from the extract for use.

Subsequently, the compound of formula (4) is hydrated to obtain the alcohol of formula (2). In the present invention, as stated above, the extract of the compound of formula (4) as produced above can directly be used.

A method of hydrating the carbon-carbon double bond of the compound of formula (4) in the presence of a lactone is not particularly limited. Examples of such a method include (i) a method of carrying out oxidative hydrolysis after hydroboration, (ii) a method of hydrolyzing an ester which is obtained by adding lower carboxylic acid to the compound of formula (4) in the presence of an acid catalyst, and (iii) a method of carrying out alkaline hydrolysis on a lactone, converting the obtained product into an iodolactone, and eliminating iodine by reduction for relactonization, as described in Tetrahedron, 47, 5513 (1991), and Liebigs Ann. Chem., 691 (1993). Of these, from the viewpoint of yield, economical efficiency and mass productivity, (ii) the method of using lower carboxylic acid is preferable.

Now, (ii) a method of producing the alcohol of formula (2) by adding lower carboxylic acid to the compound of formula (4) to generate lower carboxylate and then hydrolyzing lower carboxylate for hydration will be explained.

Lower carboxylic acid added to the carbon-carbon double bond of the compound of formula (4) is not particularly limited, and examples of such lower carboxylic acid include formic acid, acetic acid, and trifluoroacetic acid. Of these, in terms of availability, yield and economical efficiency, formic acid is preferably used. In general, the amount of lower carboxylic acid used is preferably 2 or more times to the compound of formula (4).

Examples of an acid catalyst used in the lower carboxylic acid addition reaction include perchloric acid, p-toluenesulfonic acid, trifluromethanesulfonic acid, acidic ion exchange resin, and heteropoly acid. These acid catalysts may be used singly or in combination of two or more types. In terms of yield and economical efficiency, of these, trifluoromethanesulfonic acid is preferably used. In general, the amount of an acid catalyst used is preferably 0.1 or more times to the compound of formula (4).

In general, the reaction temperature of the lower carboxylic acid addition reaction is preferably 80° C. or higher.

When the addition reaction is carried out, the compound of formula (4), lower carboxylic acid and an acid catalyst may be reacted all together. However, if emphasis is placed on reaction yield, it is preferable to mix lower carboxylic acid and an acid catalyst in advance, and then drop the compound of formula (4) thereto.

It may also be possible to distill off solvents from the obtained lower carboxylate and to purify the lower carboxylate by silica gel column chromatography or precision distillation.

Subsequently, water is added to the obtained lower carboxylate for hydrolysis (alkaline hydrolysis) and hydration, so as to obtain the alcohol of formula (2).

In hydrolysis, the amount of water added is not particularly limited, but it is preferably 0.5 or more times to the mass of the reaction solution by weight, and it is also preferably 5 or less times thereto by weight.

To enhance extraction efficiency, a sodium chloride solution or the like may also be used.

Moreover, in the present invention, alkaline hydrolysis is also preferable. Examples of a base used in alkaline hydrolysis of lower carboxylate include sodium hydroxide, potassium hydroxide, sodium carbonate, potassium carbonate, sodium hydrogen carbonate, potassium bicarbonate, sodium cyanide, potassium cyanide, hydrazine, and guanidine. These bases may be used singly or in combination of two or more types. In this alkaline hydrolysis, in order not to hydrolyze the γ-butyrolactone structure, the base is added to the substrate in a controlled amount within a range from 1 to 1.2 equivalent weight.

Examples of a solvent used in alkaline hydrolysis include water, and a mixture of water with alcohols such as methanol and ethanol, or with ethers such as tetrahydrofuran.

The reaction temperature of hydrolysis may be selected, as appropriate, depending on compounds.

The thus obtained alcohol of formula (2) can be used in the following reaction without subjecting to purification, but it may also be purified by silica gel column chromatography or precision distillation. Moreover, it may also be possible that the alcohol of formula (2) is extracted with an extraction solvent, and after distilling the solvent off, silica gel column chromatography or vacuum distillation is carried out thereon, if necessary.

Examples of an extraction solvent used in extraction of the alcohol of formula (2) include aromatic hydrocarbons such as toluene and xylene, ethers such as dimethyl ether, methyl tert-butyl ether and diisopropyl ether, ketones such as methyl n-propyl ketone, methyl n-butyl ketone and MIBK, and esters such as ethyl acetate. These solvents may be used singly or as a mixture of two or more types. Of these, ketones, particularly MIBK is preferably used, since it has high recovery rate and good separativity of two liquid phases.

The amount of an extraction solvent used is not particularly limited. It is preferably 0.05 or more times to the amount of extraction feed by weight, and it is also preferably 20 or less times to the amount of extraction feed by weight.

Extraction may be carried out only once, or it may also be carried out twice or more. The extracted layer may be washed with water, or alkalescent aqueous solutions such as a sodium hydrogen carbonate solution and sodium carbonate solution in water.

Possible vacuum distillation methods may include either a common simple distillation, or a distillation using a forced agitation or centrifugal thin film evaporator. To prevent degradation by thermal history, a thin film evaporator is preferably used.

Next, a method of producing the ester of formula (1) will be explained.

The ester of formula (1) can be obtained by (meth) acrylation of the alcohol of formula (2). An example of a method of (meth)acrylation includes a method of reacting (meth)acrylic halide, (meth)acrylic anhydride, (meth)acrylic acid or (meth)acrylate with the alcohol of formula (2) for esterification.

When (meth)acrylation is carried out using (meth)acrylic halide or (meth)acrylic anhydride, generally a base is used. A base used herein is not particularly limited as long as it neutralizes acid generated. Examples of such a base include triethylamine, pyridine, 2-methylpyridine, 2-methyl-5-ethylpyridine, 2,6-dimethylpyridine, triethylenetetramine, triethanolamine, piperazine and sodium hydrogen carbonate. These bases may be used singly or in combination of two or more types.

In the case of (meth)acrylic halide, the molar ratio of (meth)acrylic halide is preferably 1.2 mol or more based on 1 mol alcohol and is preferably 2 mol or less based on 1 mol alcohol, and the molar ratio of base is preferably 1.3 mol or more based on 1 mol alcohol and is preferably 2.4 mol or less based on 1 mol alcohol. In the case of (meth)acrylic anhydride, the molar ratio of (meth)acrylic anhydride is preferably 0.9 mol or more based on 1 mol alcohol and is preferably 1.5 mol or less based on 1 mol alcohol, and the molar ratio of base is preferably 0.5 mol or more based on 1 mol alcohol and is preferably 1.6 mol or less based on 1 mol alcohol.

Moreover, 4-dimethylaminopyridine or the like may be added to the reaction system because it can complete the reaction in a shorter reaction time.

The reaction temperature is preferably −80° C. or higher, particularly preferably −20° C. or higher to sufficiently increase a reaction rate, and it is also preferably 100° C. or lower, particularly preferably 80° C. or lower to sufficiently inhibit side reaction. Furthermore, when (meth)acrylation is carried out using (meth)acrylic halide, since it has high reaction activity, it is preferable to carry out the reaction at 20° C. or lower, and particularly preferably at −20° C. to 20° C. Still further, when (meth)acrylation is carried out using (meth)acrylic anhydride, since it has low reaction activity, it is preferable to carry out the reaction at 40° C. or higher, and particularly preferably at 40° C. to 80° C.

In the reaction, a solvent is not essential, but it is preferable to use ketone solvents such as 2-butanone and 4-methyl-2-pentanone, or halogenated hydrocarbon solvents such as methylene chloride and chloroform to control temperature.

When (meth)acrylation is carried out with (meth)acrylic anhydride., so as to prevent polymerization due to high temperature, it is preferable to use a polymerization inhibitor and it is preferable to carry out air bubbling.

Examples of a polymerization inhibitor used herein include phenol compounds such as hydroquinone and p-methoxyphenol, amine compounds such as N,N'-diisopropyl-p-phenylenediamine, N,N'-di-2-naphthyl-p-phenylenediamine and N-phenyl-N'-(1,3-dimethylbutyl)-p-phenylenediamine, and N-oxyl compounds such as 4-hydroxy-2,2,6, 6-tetramethylpiperidine-N-oxyl and 4-[H-(OCH$_2$CH$_2$)$_n$— O]-2,2,6,6-tetramethylpiperidine-N-oxyl(n=1 to 18). These polymerization inhibitors may be used singly or in combination of two or more types. The used amount is not particularly limited, and it is determined as appropriate.

When (meth)acrylation is carried out with (meth)acrylic acid, an acid catalyst is generally used. Examples of an acid catalyst used herein include sulfuric acid, p-toluenesulfonic acid monohydrate, and acidic ion exchange resin. These acid catalysts may be used singly or in combination of two or more types.

The molar ratio of (meth)acrylic acid is preferably 1.02 mol or more, particularly preferably 1.05 mol or more based on 1 mol alcohol, and is preferably 2.5 mol or less, particularly preferably 2 mol or less based on 1 mol alcohol. The molar ratio of acid catalyst is preferably 0.001 mol or more, particularly preferably 0.01 mol or more based on 1 mol alcohol, and is preferably 0.2 mol or less, particularly preferably 0.1 mol or less based on 1 mol alcohol.

In general, the reaction is carried out while eliminating water using an apparatus such as a decanter, and tetrahydrofuran, hexane, toluene or the like is used as an azeotropic solvent.

In terms of reaction rate, the reaction temperature is generally 0° C. or higher, preferably 40° C. or higher, and more preferably 60° C. or higher, and further, generally 170° C. or lower, preferably 150° C. or lower, and more preferably 130° C. or lower.

Moreover, so as to prevent polymerization due to high temperature, it is preferable to use a polymerization inhibitor and it is preferable to carry out air bubbling. Examples of a polymerization inhibitor used herein are the same as in the case of (meth)acrylation with (meth)acrylic anhydride.

Furthermore, when (meth)acrylation is carried out by transesterification with (meth)acrylate, preferably with methyl(meth)acrylate, a catalyst for transesterification is used. Any common catalyst used for transesterification may be used herein. Examples of such a catalyst include titanium catalysts such as tetramethoxytitanium, tetra-n-butoxytitanium and tetraisopropoxytitanium, and tin catalysts such as dibutyl tin oxide and dioctyl tin oxide. These catalysts may be used singly or in combination of two or more types.

In the case of a titanium catalyst, the molar ratio of (meth)acrylate is preferably 1.5 mol or more based on 1 mol alcohol and is preferably 20 mol or less based on 1 mol alcohol, and the molar ratio of the catalyst is preferably 0.0001 mol or more based on 1 mol alcohol and is preferably 0.05 mol or less based on 1 mol alcohol. In the case of a tin catalyst, the molar ratio of (meth)acrylate is preferably 1.5 mol or more based on 1 mol alcohol and is preferably 20 mol or less based on 1 mol alcohol, and the molar ratio of the catalyst is preferably 0.0005 mol or more based on 1 mol alcohol and is preferably 0.1 mol or less based on 1 mol alcohol.

In general, the reaction temperature is preferably −30° C. or higher and preferably 150° C. or lower. It is particularly preferably between 60° C. and 150° C., since alcohol generated as a by-product is eliminated, and also a sufficient reaction rate is obtained at a temperature within the above range.

Moreover, so as to prevent polymerization due to high temperature, it is preferable to use a polymerization inhibitor and it is preferable to carry out air bubbling. Examples of a polymerization inhibitor used herein are the same as in the case of (meth)acrylation with (meth)acrylic anhydride.

For (meth)acrylation of the alcohol of formula (2), if taking into consideration reactivity and yield, a method of using (meth)acrylic halide or (meth)acrylic anhydride is preferable. If taking into consideration simplicity of apparatuses and pretreatment, a method of using (meth)acrylic acid is preferable. If taking into consideration recovery performance and waste treatment, a method of transesterifying with (meth)acrylate is preferable.

The (meth)acrylate of the present invention is obtained by adding, if necessary, methanol or the like after (meth) acrylation, washing with water or the like, and distilling off solvents followed by purification by silica gel column chromatography or precision distillation.

4. Polymer of the Present Invention

The polymer of the present invention is obtained by (co)polymerizing a monomer composition comprising the monomer represented by the above formula (1). It is preferably used for a resist composition, and in particular, for a chemically amplified resist composition. A case where the polymer of the present invention is a resin for a chemically amplified resist composition will be explained below.

The resin for chemically amplified resist composition is required to have a property to become soluble in an alkaline solution by acid and to have dry etching resistance. The homopolymer of the monomer represented by the above formula (1), or the copolymer of two or more types of the monomer represented by the above formula (1) has a property to become soluble in an alkaline solution by acid, high dry etching resistance, and further, excellent solubility in organic solvents. Moreover, a structure having a functional group that is easily eliminated by the action of acid, or a structure having high dry etching resistance such as a cyclic hydrocarbon group may also be introduced into such a polymer.

A structure in which a hydroxy or carboxy group is protected by an acetyl, t-butyl, tetrahydropyranyl, methyladamantyl, ethyladamantyl or other groups is an example of the structure having a functional group that is easily eliminated by the action of acid.

In order to introduce the structure having a functional group that is easily eliminated by the action of acid or the structure having high dry etching resistance, the monomer represented by the above formula (1) may be copolymerized with a monomer having such a structure.

As a monomer having such a structure, for example, the one that is known as a raw material monomer for the resin for chemically amplified resist composition is available. A raw material monomer used for the polymer of the present invention is appropriately selected depending on light source used in lithography.

For example, when a KrF excimer laser or electron beam is used as a light source, considering its high etching resistance, a polymer obtained by copolymerizing the monomer represented by the above formula (1) with p-hydroxystyrene or a derivative thereof is preferably used. In this case, the proportion of units derived from the monomer represented by the above formula (1) is preferably 1% or more in the polymer and is preferably 25% or less in the polymer.

When an ArF excimer laser is used as a light source, a polymer obtained by copolymerizing the monomer represented by the above formula (1) with a monomer having a cyclic hydrocarbon group is preferably used. copolymerization of a monomer having a cyclic hydrocarbon group realize high light transmittance and high etching resistance.

Among them, the following copolymers are particularly preferably used: an acrylic copolymer obtained by copolymerizing the monomer represented by the above formula (1), a monomer having a cyclic hydrocarbon group, and a monomer having a hydrophilic functional group; an acrylic copolymer obtained by copolymerizing the monomer represented by the above formula (1), a monomer having a cyclic hydrocarbon group, and maleic anhydride; and an acrylic copolymer obtained by copolymerizing the monomer represented by the above formula (1), a monomer having a cyclic hydrocarbon group, and a monomer having a lactone structure such as a γ-butyrolactone structure. It is known that an acrylic copolymer obtained by copolymerizing a monomer having a cyclic hydrocarbon group and a monomer having a hydrophilic functional group, an acrylic copolymer obtained by copolymerizing a monomer having a cyclic hydrocarbon group and maleic anhydride, and an acrylic copolymer obtained by copolymerizing a monomer having a cyclic hydrocarbon group and a monomer having a lactone structure are preferable as a resin for ArF excimer laser lithography. Introduction of the monomer unit represented by the above formula (1) into these polymers enables to improve dry etching resistance, thereby providing an excellent resist pattern with only a little roughness on a surface thereof after dry etching.

A monomer unit having a cyclic hydrocarbon group imparts high dry etching resistance to a polymer comprising the same. In particular, a monomer unit comprising a protecting group that is eliminated by acid (a cyclic hydrocarbon group may also be a protecting group by itself) also imparts high sensitivity in photolithography using an ArF excimer laser with a wavelength of 193 nm to the polymer comprising the same. The monomer unit having a cyclic hydrocarbon group may be of one type, or of two or more types, if necessary.

Preferred examples of a monomer unit having a cyclic hydrocarbon group include cyclohexyl(meth)acrylate, isobornyl(meth)acrylate, adamantyl(meth)acrylate, tricyclodecanyl(meth)acrylate, dicyclopentadienyl(meth)acrylate, and their derivatives having substituent(s) such as an alkyl group, hydroxy group and carboxy group on the cyclic hydrocarbon groups of these monomers.

Specific examples of such a monomer unit include 1-isobornyl(meth)acrylate, 2-(meth)acryloyloxy-2-methyladamantane, 2-(meth)acryloyloxy-2-ethyladamantane, 1-(1-(meth)acryloyloxy-1-methylethyl)adamantane, cyclohexyl(meth)acrylate, adamantyl(meth)acrylate, tricyclodecanyl(meth)acrylate, and dicyclopentadienyl(meth)acrylate.

A monomer unit having a hydrophilic functional group imparts adhesion to a substrate to a polymer comprising the unit. In particular, a monomer unit comprising a protecting group that is eliminated by acid also imparts high sensitivity in photolithography using an ArF excimer laser with a wavelength of 193 nm to the polymer comprising the unit. Examples of a hydrophilic functional group include a terminal carboxy group, a terminal hydroxy group, an alkyl-substituted ether group (preferably, an alkyl-substituted ether group wherein the alkyl has 4 carbon atoms or less), a δ-valerolactonyl group, and a γ-butyrolactonyl group. It should be noted that some of the above listed hydrophilic functional groups are generally included in hydrophobic groups. However, since even such type of hydrophilic functional groups has hydrophilia that is sufficient in the present invention, they are herein defined as hydrophilic functional groups. The monomer units having a hydrophilic functional group may be one type, or two or more types, if necessary.

Preferred examples of a monomer unit having a hydrophilic functional group include (meth)acrylic acid, (meth)acrylate having a terminal hydroxy group, (meth)acrylate having an alkyl-substituted ether group, (meth)acrylate having a δ-valerolactonyl group, (meth)acrylate having a γ-butyrolactonyl group, and their derivatives having substituent(s) such as an alkyl group, hydroxy group and carboxy group on the hydrophilic functional groups of these monomers other than (meth)acrylic acid.

Specific examples of such a monomer unit include (meth)acrylic acid, 2-hydroxyethyl(meth)acrylate, 2-hydroxypropyl(meth)acrylate, 4-hydroxybutyl(meth)acrylate, 1-(meth)acryloyloxy-3-hydroxyadamantane, 2-methoxyethyl(meth)acrylate, 2-ethoxyethyl(meth)acrylate, β-(meth)acryloyloxy-β-methyl-δ-valerolactone, β-(meth)acryloyloxy-γ-butyrolactone, β-(meth)acryloyloxy-β-methyl-γ-butyrolactone, α-(meth)acryloyloxy-γ-butyrolactone, 2-(1-(meth)acryloyloxy)ethyl-4-butanolide, and pantolactone(meth)acrylate.

A maleic anhydride monomer unit imparts high dry etching resistance and adhesion to a substrate to a polymer comprising the unit.

A monomer unit having a lactone structure imparts high dry etching resistance and adhesion to a substrate to a polymer comprising the unit. The monomer unit having a lactone structure may be of one type, or of two or more types, if necessary.

Preferred examples of a monomer unit having a lactone structure include α-methylenelactone having 4 to 8 ring forming members, and their derivatives having substituent(s) such as an alkyl group, hydroxy group, or carboxy group on carbons of the lactone ring.

Specific examples of such a monomer unit include 2-methylene-3-propanolide, 2-methylene-4-butanolide, 2-methylene-4-methyl-4-butanolide, 2-methylene-4-ethyl-4-butanolide, 2-methylene-4,4-dimethyl-4-butanolide, 2-methylene-5-pentanolide, 2-methylene-6-hexanolide, and 2-methylene-7-heptanolide.

As a resin for chemically amplified resist composition, specifically, a polymer represented by the following formula (5-1), (5-2) or (5-3) is preferable:

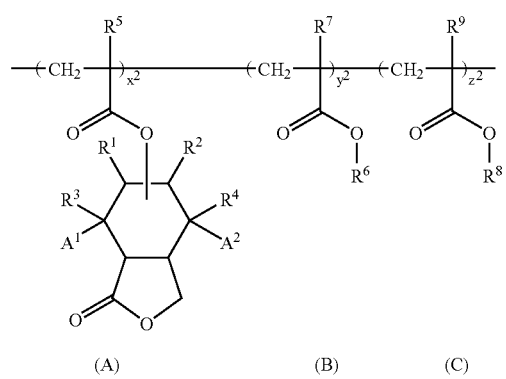

(5-1)

(A)　　　　(B)　　　　(C)

wherein each of $R^1$, $R^2$, $R^3$ and $R^4$ represents a hydrogen atom, a methyl group or an ethyl group; each of $R^5$, $R^7$ and $R^9$ represents a hydrogen atom or a methyl group; $R^6$ represents a cyclic hydrocarbon group having a group that is eliminated by acid; $R^8$ represents a group having a hydrophilic functional group or hydrogen atom; both $A^1$ and $A^2$ represent hydrogen atoms, or $A^1$ and $A^2$ form —O—, —CH$_2$— or —CH$_2$CH$_2$—; and $x^2$, $y^2$ and $z^2$ represent the ratios of a unit (A), a unit (B) and a unit (C), respectively, wherein when $x^2+y^2+z^2=1$, $x^2$, $y^2$ and $z^2$ are any given numbers satisfying $0<x^2\leq 1$, $0\leq y^2<1$, and $0\leq z^2<1$;

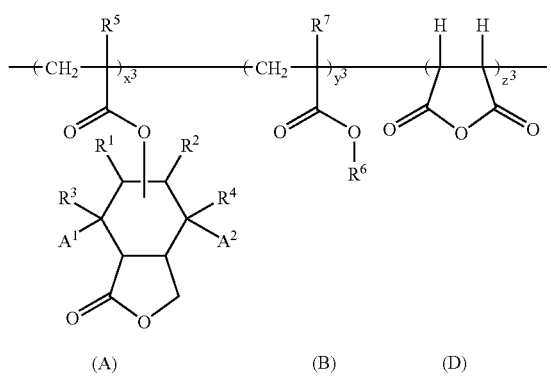

(5-2)

(A)　　　　(B)　　　　(D)

wherein each of $R^1$, $R^2$, $R^3$ and $R^4$ represents a hydrogen atom, a methyl group or an ethyl group; each of $R^5$ and $R^7$ represents a hydrogen atom or a methyl group; $R^6$ represents a cyclic hydrocarbon group having a group that is eliminated by acid; both $A^1$ and $A^2$ represent hydrogen atoms, or $A^1$ and $A^2$ form —O—, —CH$_2$— or —CH$_2$CH$_2$—; and $x^3$, $y^3$ and $z^3$ represent the ratios of a unit (A), a unit (B) and a unit (D), respectively, wherein when $x^3+y^3+z^3=1$, $x^3$, $y^3$ and $z^3$ are any given numbers satisfying $0<x^3\leq 1$, $0\leq y^3<1$, and $0\leq z^3<1$; or

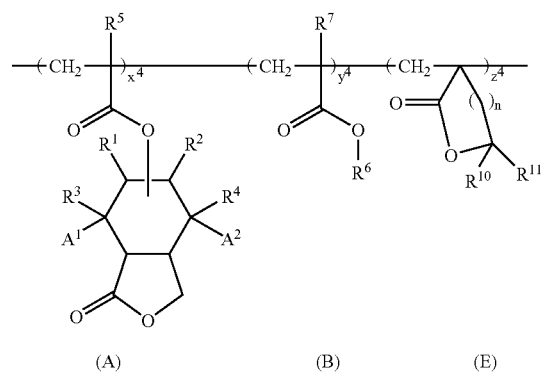

(5-3)

(A)　　　　(B)　　　　(E)

wherein each of $R^1$, $R^2$, $R^3$, $R^4$, $R^{10}$ and $R^{11}$ represents a hydrogen atom, a methyl group or an ethyl group; each of $R^5$ and $R^7$ represents a hydrogen atom or a methyl group; $R^6$ represents a cyclic hydrocarbon group having a group that is eliminated by acid; both $A^1$ and $A^2$ represent hydrogen atoms, or $A^1$ and $A^2$ form —O—, —CH$_2$— or —CH$_2$CH$_2$—; n represents an integer of 0 to 4; and $x^4$, $y^4$ and $z^4$ represent the ratios of a unit (A), a unit (B) and a unit (E), respectively, wherein when $x^4+y^4+z^4=1$, $x^4$, $y^4$ and $z^4$ are any given numbers satisfying $0<x^4\leq 1$, $0\leq y^4<1$, and $0\leq z^4<1$.

In the above formula (5-1), the unit (B) represents a monomer unit having a cyclic hydrocarbon group, and the unit (C) represents a monomer unit having a hydrophilic functional group. When $R^8$ in the unit (C) is a hydrogen atom, it has a carboxy group (—COOH), and so it has hydrophilia.

$R^6$ is preferably one or more types selected from a group consisting of a cyclohexyl group, an isobornyl group, an adamantyl group, a tricyclodecanyl group, a dicyclopentadienyl group, and these cyclic hydrocarbon groups having a substituent. It is particularly preferably 2-methyladamantyl group.

$R^8$ is preferably one or more types selected from a group consisting of a terminal hydroxy group, a group having an alkyl-substituted ether group, a δ-valerolactonyl group, a γ-butyrolactonyl group and a hydrogen atom. It is particularly preferably a γ-butyrolactonyl group.

$x^2$, $y^2$ and $z^2$ represent the ratios of the units (copolymer composition). When $x^2+y^2+z^2=1$, $x^2$, $y^2$ and $z^2$ are any given numbers satisfying $0<x^2 \leq 1$, $0 \leq y^2<1$, and $0 \leq z^2<1$. Preferably, $0.3 \leq x^2 \leq 0.6$, $0.3 \leq y^2 \leq 0.6$, and $0 \leq z^2 \leq 0.4$. This copolymer composition makes it possible to improve dry etching resistance and adhesion to a substrate, while maintaining sufficient solubility in organic solvents.

As stated above, the units (A), (B) or (C) is not necessarily of the same type, but they may be of two or more types as long as they can be represented by the above general formula. Moreover, in the above formula (5-1), each unit can be in any sequence. Accordingly, the polymer represented by the above formula (5-1) may be either a random copolymer or a block copolymer.

In the above formula (5-2), the unit (B) represents a monomer unit having a cyclic hydrocarbon group, and the unit (D) is a maleic anhydride monomer unit.

$R^6$ is preferably one or more types selected from a group consisting of a cyclohexyl group, an isobornyl group, an adamantyl group, a tricyclodecanyl group, a dicyclopentadienyl group, and these cyclic hydrocarbon groups having a substituent. It is particularly preferably 2-methyladamantyl group.

$x^3$, $y^3$ and $z^3$ represent the ratios of the units (copolymer composition). When $x^3+y^3+z^3=1$, $x^3$, $y^3$ and $z^3$ are any given numbers satisfying $0<x^3 \leq 1$, $0 \leq y^3<1$, and $0 \leq z^3<1$. Preferably, $0.3 \leq x^3 \leq 0.6$, $0.3 \leq y^3 \leq 0.6$, and $0 \leq z^3 \leq 0.4$. This copolymer composition makes it possible to improve dry etching resistance and adhesion to a substrate, while maintaining sufficient solubility in organic solvents.

As stated above, the units (A) or (B) is not necessarily of the same type, but they may be of two or more types as long as they can be represented by the above general formula. Moreover, in the above formula (5-2), each unit can be in any sequence. Accordingly, the polymer represented by the above formula (5-2) may be either a random copolymer or a block copolymer.

In the above formula (5-3), the unit (B) represents a monomer unit having a cyclic hydrocarbon group, and the unit (E) represents a monomer unit having a lactone structure.

$R^6$ is preferably one or more types selected from a group consisting of a cyclohexyl group, an isobornyl group, an adamantyl group, a tricyclodecanyl group, a dicyclopentadienyl group, and these cyclic hydrocarbon groups having a substituent. It is particularly preferably 2-methyladamantyl group.

Each of $R^{10}$ and $R^{11}$ is preferably a hydrogen atom or a methyl group, and particularly preferably a methyl group.

n is preferably 0, 1 or 2.

$x^4$, $y^4$ and $z^4$ represent the ratios of the units (copolymer composition). When $x^4+y^4+z^4=1$, $x^4$, $y^4$ and $z^4$ are any given numbers satisfying $0<x^4 \leq 1$, $0 \leq y^4<1$, and $0 \leq z^4<1$. Preferably, $0.3 \leq x^4 \leq 0.6$, $0.3 \leq y^4 \leq 0.6$, and $0 \leq z^4 \leq 0.4$. This copolymer composition makes it possible to improve dry etching resistance and adhesion to a substrate, while maintaining sufficient solubility in organic solvents.

As stated above, the units (A), (B) or (E) is not necessarily of the same type, but they may be of two or more types as long as they can be represented by the above general formula. Moreover, in the above formula (5-3), each unit can be in any sequence. Accordingly, the polymer represented by the above formula (5-3) may be either a random copolymer or a block copolymer.

In the case of using as a resin for chemically amplified resist composition, the weight-average molecular weight of the polymer of the present invention such as the polymer represented by the above formula (5-1), (5-2) or (5-3) is not particularly limited, but it is preferably 1,000 or greater and it is preferably 100,000 or smaller. The greater the weight-average molecular weight, the better the dry etching resistance that can be obtained, and the form of the resist thereby may become better. In contrast, the smaller the weight-average molecular weight, the better the solubility in the resist solution that can be obtained, and thereby resolution may be improved.

When the polymer of the present invention such as the polymer represented by the above formula (5-1), (5-2) or (5-3) is a copolymer, it may be a random copolymer, alternating copolymer, or block copolymer.

5. Method of Producing Polymer of the Present Invention

The polymer (resin for chemically amplified resist composition) of the present invention can be produced by known polymerization methods. In terms of simple production, the polymer is preferably produced by a method called drop polymerization, in which a monomer solution obtained by previously dissolving a monomer and a polymerization initiator in an organic solvent is dropped in an organic solvent that is maintained at a certain temperature.

An organic solvent used in the drop polymerization is not particularly limited. Solvents that can dissolve both a monomer and the obtained copolymer are preferable. Examples of such a solvent include 1,4-dioxane, isopropyl alcohol, acetone, tetrahydrofuran and ethyl lactate. The amount of an organic solvent used is not particularly limited, and it may be determined as appropriate.

A polymerization initiator used in the drop polymerization is not particularly limited. Examples of a polymerization initiator include azo compounds such as azobisisobutyronitrile and 2,2'-azobis(2,4-dimethylvaleronitrile), and organic peroxides such as benzoyl peroxide. Moreover, mercaptans such as n-butyl mercaptan and n-octyl mercaptan may be used as chain transfer agents. The amounts of the polymerization initiator and the chain transfer agent used are not particularly limited, and they may be determined as appropriate.

Polymerization temperature is not particularly limited in the drop polymerization method, but in general, it is preferably within a range of 50° C. to 150° C. Dropping time is not particularly limited, but in general, it is preferably 6 hours or longer. Moreover, it is preferable to maintain the temperature for 1 to 3 hours after termination of the dropping, so as to complete polymerization.

A polymer solution produced by the drop polymerization method is diluted with a good solvent such as tetrahydrofuran and 1,4-dioxane to a suitable solution viscosity, if necessary. Then, the polymer solution is dropped into a large amount of poor solvent such as heptane, methanol and water so as to deposit polymers. Thereafter, the obtained deposition is filtered and fully dried, so as to obtain the polymer of the present invention.

The step of depositing polymers by dropping a polymer solution into a large amount of poor solvent is called reprecipitation, and it is extremely effective to eliminate unreacted monomers, polymerization initiators and others that remain in the polymer solution. If these unreacted monomers and others. remain in the polymer solution, they are likely to affect resist performances. Accordingly, it is preferable to eliminate them, if possible. This reprecipitation process may be omitted in some cases.

6. Chemically Amplified Resist Composition of the Present Invention

The chemically amplified resist composition of the present invention is obtained by dissolving the above-described polymer of the present invention and a photoacid generator in a solvent. The polymer of the present invention may be used singly or in combination of two or more types.

In a chemically amplified resist composition (excluding a solvent), the content of the polymer of the present invention is preferably 70% or more by weight in total. Moreover, in a chemically amplified resist composition (excluding a solvent), the content of the polymer of the present invention is preferably 99.8% or less by weight in total.

A photoacid generator used for the chemically amplified resist composition of the present invention can appropriately be selected from among acid generators that can be used for a chemically amplified resist composition. The photoacid generator can be used singly or in combination of two or more types.

Examples of such a photoacid generator include an onium salt compound, a sulfone imide compound, a sulfone compound, a sulfonate compound, a quinone diazide compound, and a diazo methane compound. Of these, onium salt compounds such as a sulfonium salt, iodonium salt, phosphonium salt, diazonium salt and pyridinium salt are preferably used.

Specific examples of a photoacid generator include triphenylsulfonium triflate, triphenylsulfonium hexafluoro antimonate, triphenylsulfonium naphthalene sulfonate, (hydroxy phenyl) benzyl methyl sulfonium toluene sulfonate, diphenyl iodonium triflate, diphenyl iodonium pyrene sulfonate, diphenyl iodonium dodecyl benzene sulfonate, and diphenyl iodonium hexafluoro antimonate.

The amount of a photoacid generator used is appropriately determined depending on the type of a photoacid generator used or other conditions, but the amount is generally 0.1 part or more by weight, and preferably 0.5 parts or more by weight, based on 100 parts by weight of a polymer for resist (the polymer of the present invention). By setting the amount of a photoacid generator used within the above range, a chemical reaction due to the catalytic action of acid generated as a result of exposure can sufficiently take place. Moreover, the amount of a photoacid generator used is generally 20 parts or less by weight, and preferably 10 parts or less by weight, based on 100 parts by weight of a polymer for resist (the polymer of the present invention). By setting the amount of a photoacid generator used within the above range, the stability of a resist composition is improved, and unevenness generated when the composition is applied, or scum or the like generated in a developing process is sufficiently reduced.

A solvent used for the chemically amplified resist composition of the present invention is appropriately selected depending on purposes. However, the selection of the solvent may be subject to some constraints other than solubility of a resin, such as the ones regarding the homogeneity and appearance of a coating film, and safety.

Examples of solvents usually used in the present invention include linear ketones such as 2-pentanone and 2-hexanone; cyclic ketones such as cyclopentanone and cyclohexanone; propyleneglycol monoalkyl acetates such as propyleneglycol monomethylether acetate and propyleneglycol monoethylether acetate; ethyleneglycol monoalkylether acetates such as ethyleneglycol monomethylether acetate and ethyleneglycol monoethylether acetate; propyleneglycol monoalkylethers such as propyleneglycol monomethylether and propyleneglycol monoethylether; ethyleneglycol monoalkylethers such as ethyleneglycol monomethylether and ethyleneglycol monoethylether; diethyleneglycol alkylethers such as diethyleneglycol dimethylether and diethyleneglycol diethylether; esters such as ethyl acetate and ethyl lactate; alcohols such as cyclohexanol and 1-octanol; ethylene carbonate, γ-butyrolactone, or the like. These solvents may be used singly or in combination of two or more types.

The amount of a solvent used depends on the thickness of a resist film to be formed. In general, the amount is 100 parts or more by weight based on 100 parts by weight of a polymer for resist (the polymer of the present invention). Moreover, in general, the amount is 10000 parts or less by weight based on 100 parts by weight of a polymer for resist (the polymer of the present invention).

In addition, the chemically amplified resist composition of the present invention can further comprise various additives such as a surfactant, quencher, sensitizer, antihalation agent, stabilizer and antifoaming agent, if necessary. The amount of these additives is not particularly limited, but it may be determined as appropriate.

Examples of a surfactant include nonionic surfactants, such as polyoxylene lauryl ether and polyethyleneglycol dilaurate, as well as surfactants known as the following trade names, such as Polyflow No. 75 (produced by Kyoeisha Chemical Co., Ltd.), Megaflax F173 (produced by Dainippon Ink and Chemicals Incorporated), Surflon SC-105 produced by Asahi Glass Co. Ltd.), and L-7001 (produced by Shin-Etsu Chemical Co., Ltd.).

7. Pattern Formation Method of the Present Invention

Next, an example of the pattern formation method of the present invention will be explained.

First, the chemically amplified resist composition of the present invention is coated by spin-coating or the like on the surface of a substrate such as a silicon wafer, on which a pattern is to be formed. Then, the substrate, on which the chemically amplified resist composition is coated, is dried by baking treatment (pre-bake), so that a resist film is formed on the substrate.

Next, a light with a wavelength of 250 nm or shorter is applied to the thus obtained resist film using a photomask (exposure). The light used in the exposure preferably has a wavelength of 220 nm or shorter, and particularly preferably, it is an ArF excimer laser.

After the light irradiation (exposure), baking treatment (PEB) is carried out as appropriate, and thereafter, the substrate is immersed in an alkaline developing solution to eliminate the exposed portion by dissolving it therein (development). Any known alkaline developing solution can be used herein. After the development, the substrate is rinsed with pure water or the like, as appropriate. Thus, a resist pattern is formed on the substrate.

In general, a substrate on which a resist pattern is formed is appropriately subjected to baking treatment (post exposure bake) so that the resist is reinforced. Portions having no resists are selectively etched. After the etching, the resist is generally eliminated using a release agent.

EXAMPLES

The present invention will be explained in detail by the following examples. However, the examples are not intended to limit the scope of the invention. The term "%" is herein used to mean "% by weight", and the term "part" is herein used to mean "part by weight", unless otherwise specified.

The measurement of properties of the produced copolymer was carried out by the following methods.

<Weight-average Molecular Weight>

The weight-average molecular weight of the copolymer was determined by gel permeation chromatography (hereinafter referred to as GPC) relative to standard poly(methyl) methacrylate. Chloroform or tetrahydrofuran was used as a solvent.

<Average Copolymer Composition of Copolymers (mol %)>

The average copolymer composition of copolymers was determined by $^1$H-NMR measurement. Chloroform-d1 or acetone-d6 was used as a solvent.

Example A1

Production example of a mixture (hereinafter referred to as the compound of formula (7)) of 8-hydroxy-4-oxatricyclo[5.2.1.0$^{2,6}$]decane-3-one and 9-hydroxy-4-oxatricyclo[5.2.1.0$^{2,6}$]decane-3-one, which is represented by the following formula (7):

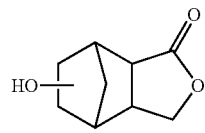

(7)

82.1 g (0.5 mol) of a white solid 5-norbornene-2,3-dicarboxylic anhydride (Wako Pure Chemical Industries, Ltd.) was dissolved in 600 ml of N,N-dimethylacetamide, the obtained solution was placed in a flask equipped with an agitator and a thermometer, and it was cooled to 0° C. to 10° C. in an ice water bath. While paying attention so that the temperature did not rise to 40° C. or higher, 21.0 g (0.5 mol) of sodium boron hydride was added thereto drop by drop followed by stirring for 12 hours. After completion of the stirring, while paying attention to the heat of neutralization and foaming, 6N hydrochloric acid was added thereto so that the solution became pH 2, and it was then left for 6 hours. Thereafter, the reaction solution was extracted with toluene, the combined organic extracts were washed with water followed by drying with sodium sulfate, and the solvent was distilled off, so as to obtain 57.3 g (0.38 mol, yield: 76%) of a white solid 4-oxatricyclo[5.2.1.0$^{2,6}$]-8-decen-3-one.

Subsequently, 71.7 g (1.56 mol) of formic acid and 52.6 g (0.35 mol) of 4-oxatricyclo[5.2.1.0$^{2,6}$]-8-decen-3-one were placed in a flask equipped with an agitator, a thermometer and a condenser, and while paying attention to heating, 5.3 g (0.035 mol) of trifluoromethanesulfonic acid was added thereto drop by drop. After reaction at 100° C. for 6 hours, excessive formic acid was removed from the reaction solution. Water was added to the remaining reaction solution followed by extraction with ethyl acetate. The combined organic extracts were washed with water and a saturated sodium hydrogen carbonate solution followed by drying with sodium sulfate, and the solvent was distilled off, so as to obtain a crude mixture of 8-formyloxy-4-oxatricyclo[5.2.1.0$^{2,6}$]decane-3-one and 9-formyloxy-4-oxatricyclo[5.2.1.0$^{2,6}$]decane-3-one. The mixture was purified by silica gel column chromatography to obtain 38.1 g (0.19 mol, yield: 55%) of a mixture of 8-formyloxy-4-oxatricyclo[5.2.1.0$^{2,6}$]decane-3-one and 9-formyloxy-4-oxatricyclo[5.2.1.0$^{2,6}$]decane-3-one that was a transparent liquid.

Subsequently, 35.3 g (0.18 mol) of the mixture of 8-formyloxy-4-oxatricyclo[5.2.1.0$^{2,6}$]decane-3-one and 9-formyloxy-4-oxatricyclo[5.2.1.0$^{2,6}$]decane-3-one and 100 ml of methanol were placed in a flask equipped with an agitator, a thermometer and a condenser. 100 g of a 10% potassium hydroxide solution was added thereto, the mixture was stirred at room temperature for 12 hours for alkaline hydrolysis, and methanol was then removed. The residue was extracted with ethyl acetate, the combined organic extracts were washed with water followed by drying with sodium sulfate, and the solvent was distilled off, so as to obtain a crude compound of formula (7). The compound was then purified by silica gel column chromatography so as to obtain 26.1 g (0.16 mol, yield: 86%) of the compound of formula (7) that was a transparent liquid.

Figure 2:
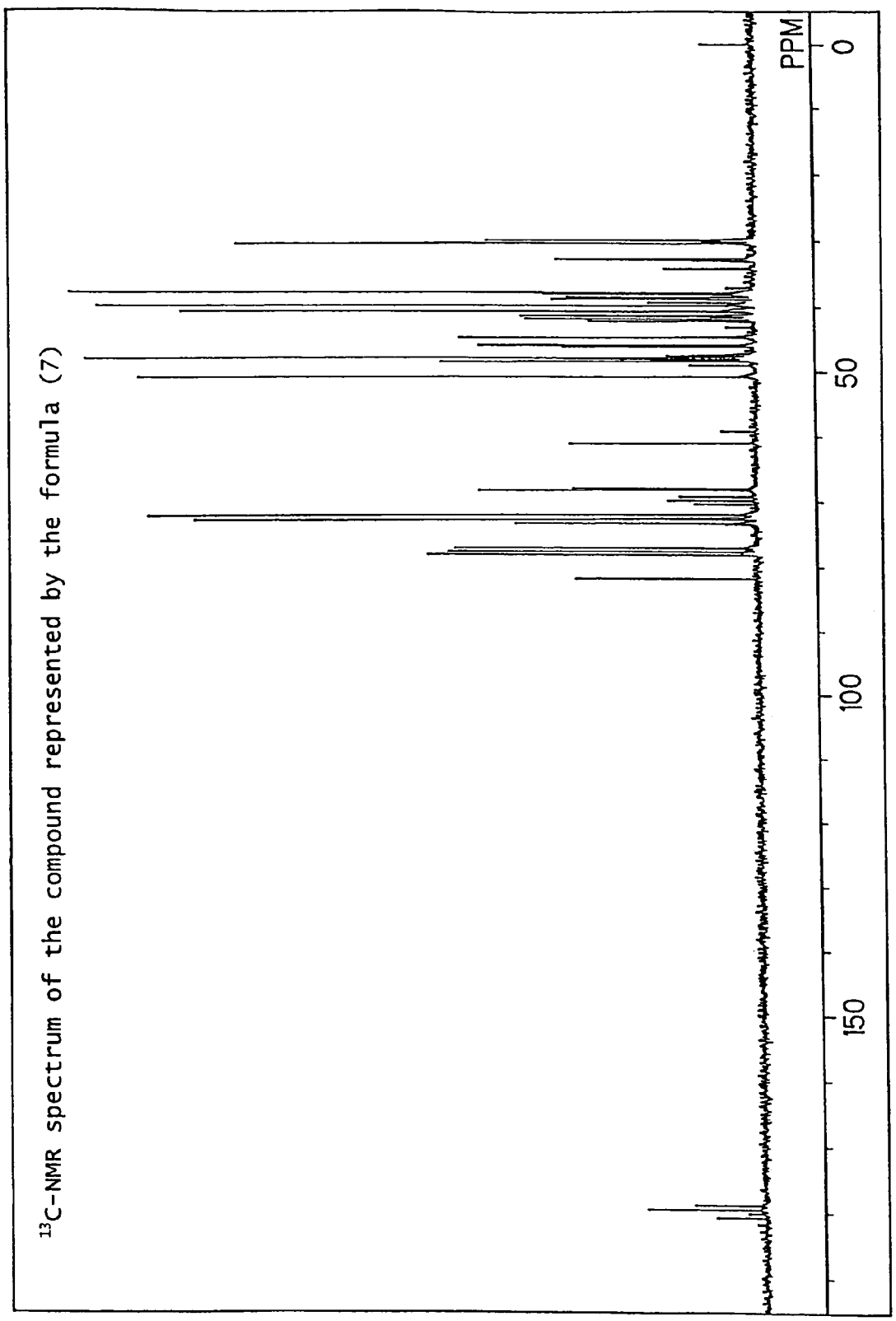
FIG. 2 is a $^{13}$C-NMR spectrum of the compound represented by the formula (7), which was obtained in Example A1.
Figure 3:
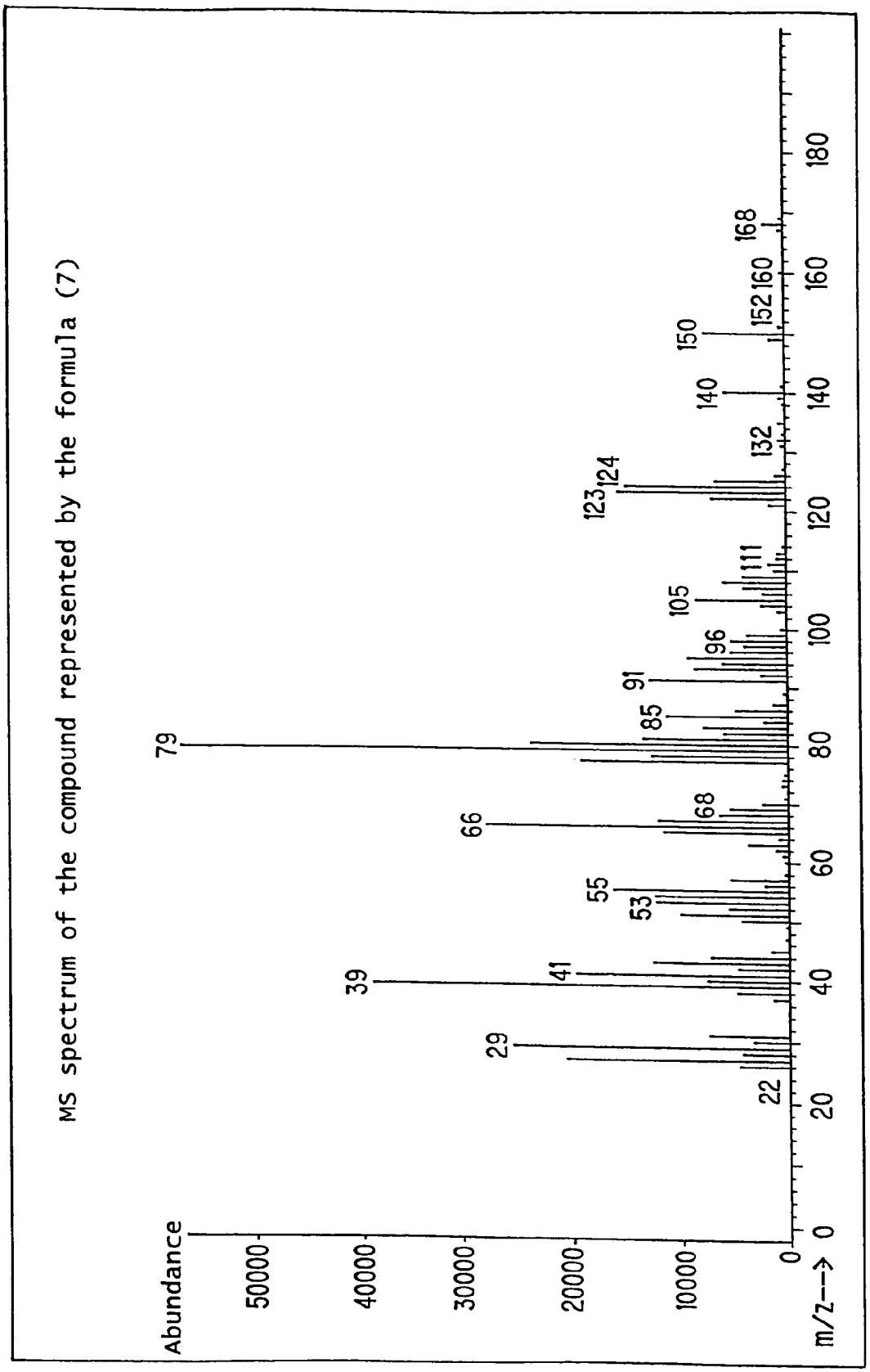
FIG. 3 is an MS spectrum of the compound represented by the formula (7), which was obtained in Example A1.

The $^1$H-NMR spectrum of the compound of formula (7) obtained in Example A1 is shown in FIG. 1, and the $^{13}$C-NMR spectrum of the same compound is shown in FIG. 2, and the MS spectrum of the same compound is shown in FIG. 3.

Example A2

Production example of a mixture (hereinafter referred to as the compound of formula (8) or OTDMA) of 8-methacryloyloxy-4-oxatricyclo[5.2.1.0$^{2,6}$]decane-3-one and 9-methacryloyloxy-4-oxatricyclo[5.2.1.0$^{2,6}$]decane-3-one, which is represented by the following formula (8):

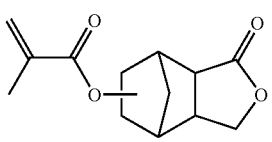

(8)

16.8 g (0.10 mol) of the compound of formula (7) produced in Example A1 and 80 ml of dry dichloromethane were placed in a flask equipped with an agitator, two dropping funnels, a thermometer and a condenser. 13.2 g (0.13 mol) of triethylamine was placed in one dropping funnel, and 12.5 g (0.12 mol) of methacryloyl chloride was placed in the other dropping funnel. The inside of the flask was substituted by nitrogen, and the system was set at about −5° C. While stirring the inside of the flask, triethylamine and methacryloyl chloride were dropped thereto over 1 hour, so that the amount of triethylamine was slightly excessive to that of methacryloyl chloride. This time, a little heat-generation was observed. After completion of the dropping, 0.3 g (0.002 mol) of dimethylaminopyridine was added thereto, and the mixture was stirred for 24 hours, while the inside of the system naturally returned to room temperature. Thereafter, 100 ml of methanol was carefully added to the reaction solution, and the mixture was washed with water and a saturated sodium hydrogen carbonate solution in succession. Thereafter, the mixture was dried with magnesium sulfate, and the solvent was distilled off, so as to obtain a crude compound of formula (8). The compound was then purified by silica gel column chromatography so as to obtain 18.4 g (0.078 mol, yield: 78%) of the compound of formula (8) that was a transparent liquid. It should be noted that the compound of formula (8) may become a mixture of isomers depending on whether the methacryloyloxy group is an endo-orientation or exo-orientation.

Figure 4:
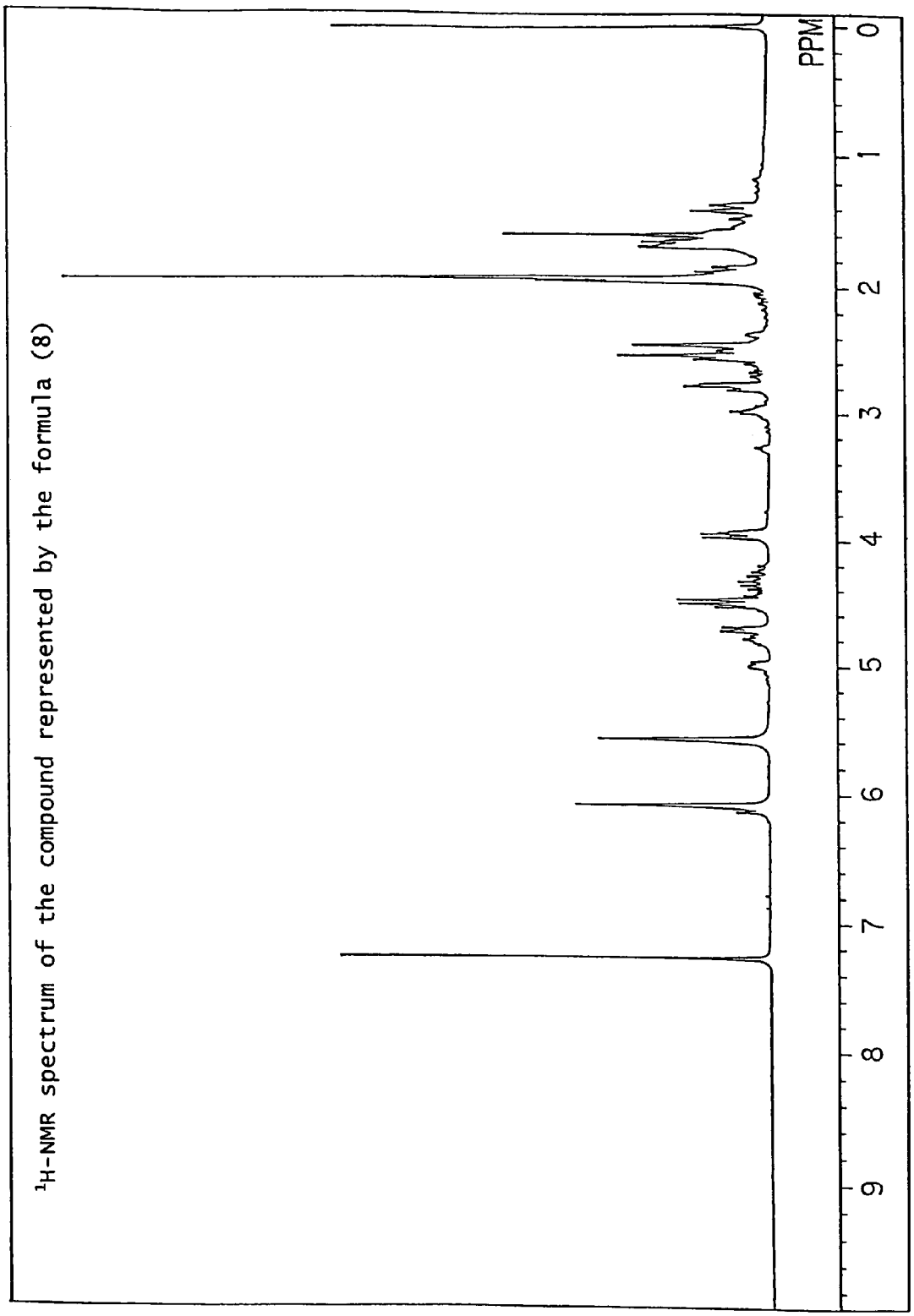
FIG. 4 is a $^1$H-NMR spectrum of the compound represented by a formula (8), which was obtained in Example A2.
Figure 5:
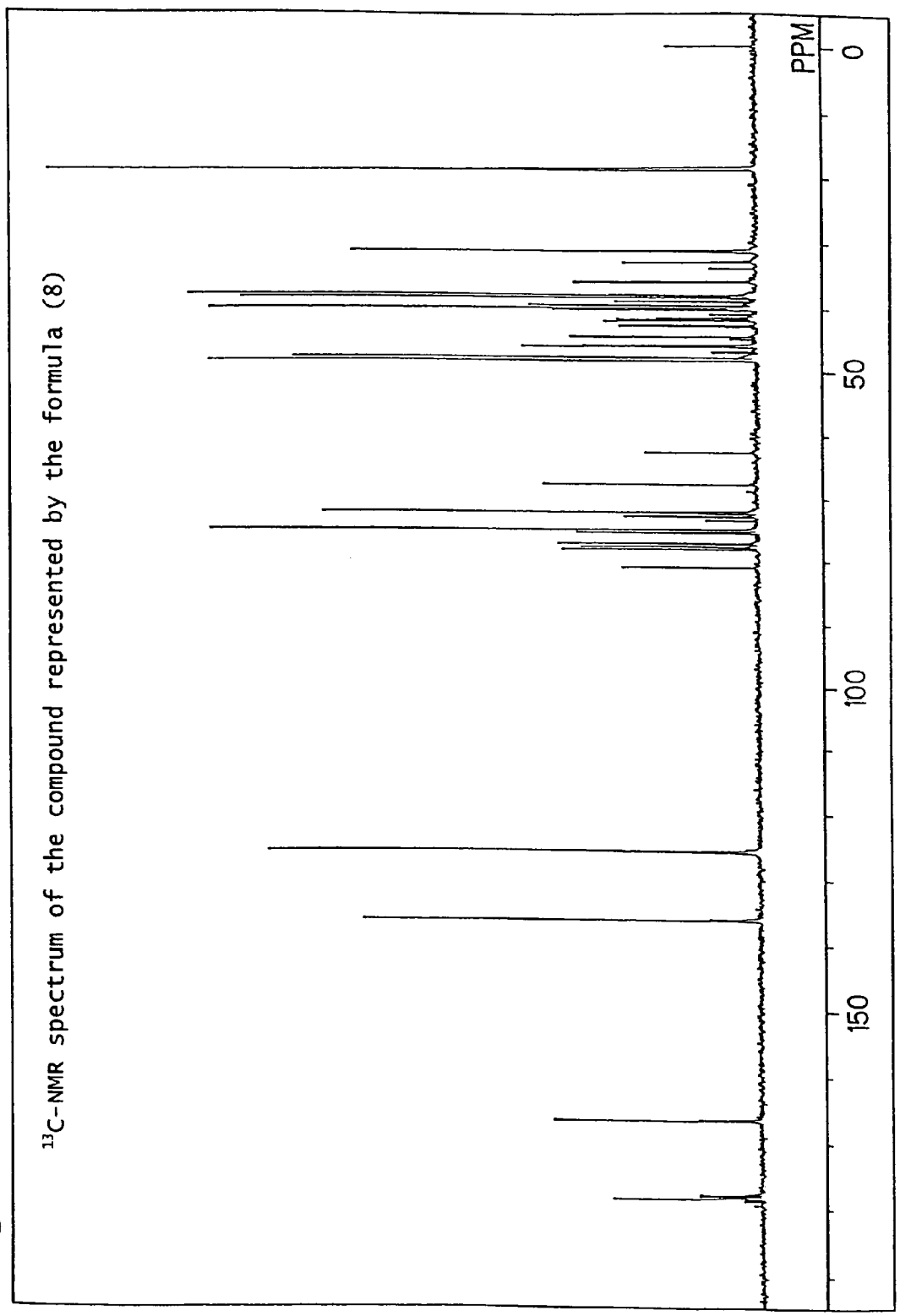
FIG. 5 is a $^{13}$C-NMR spectrum of the compound represented by the formula (8), which was obtained in Example A2.
Figure 6:
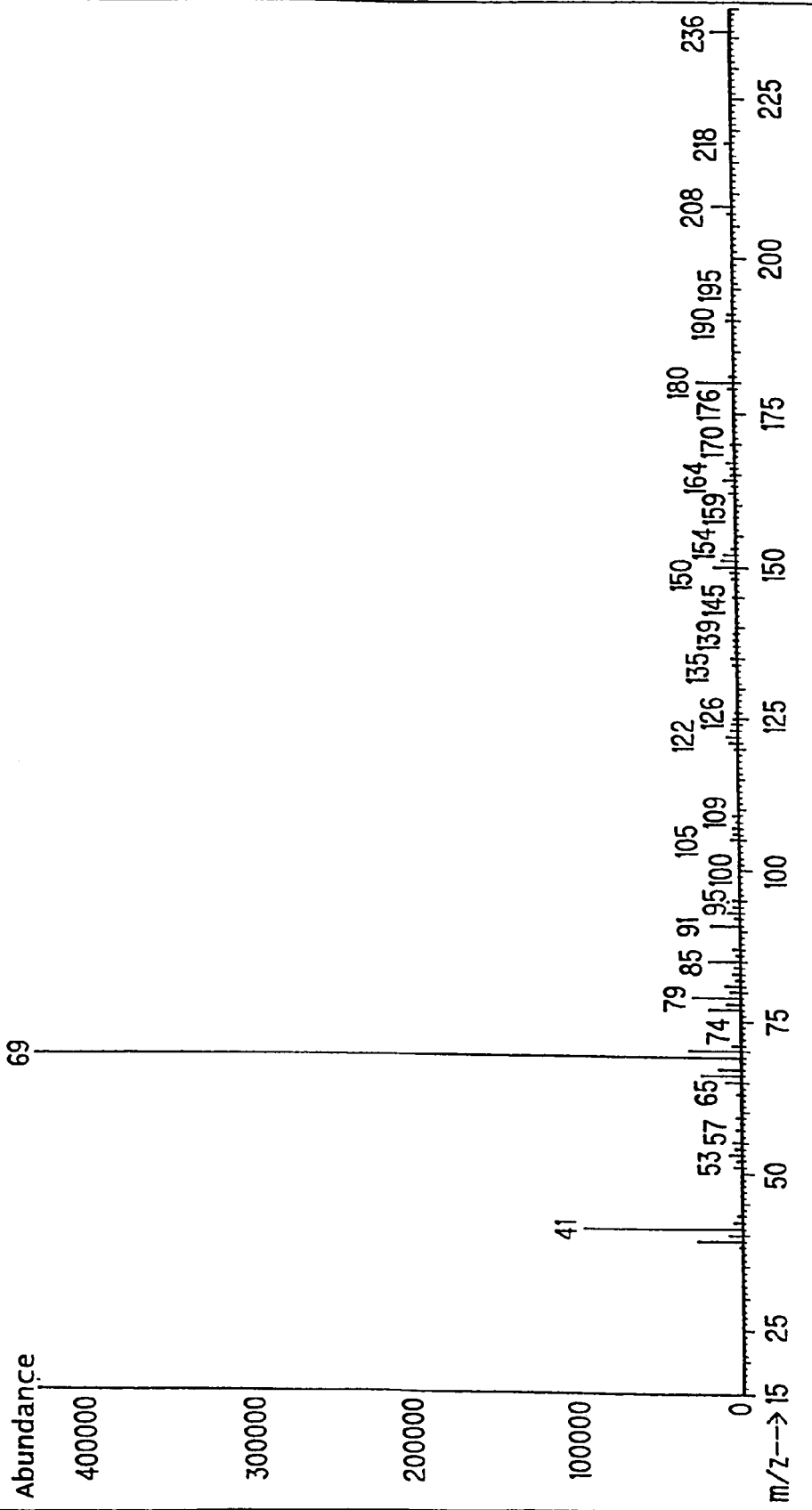
FIG. 6 is an MS spectrum (1) of each ingredient of the compound represented by the formula (8), which was obtained in Example A2.
Figure 7:
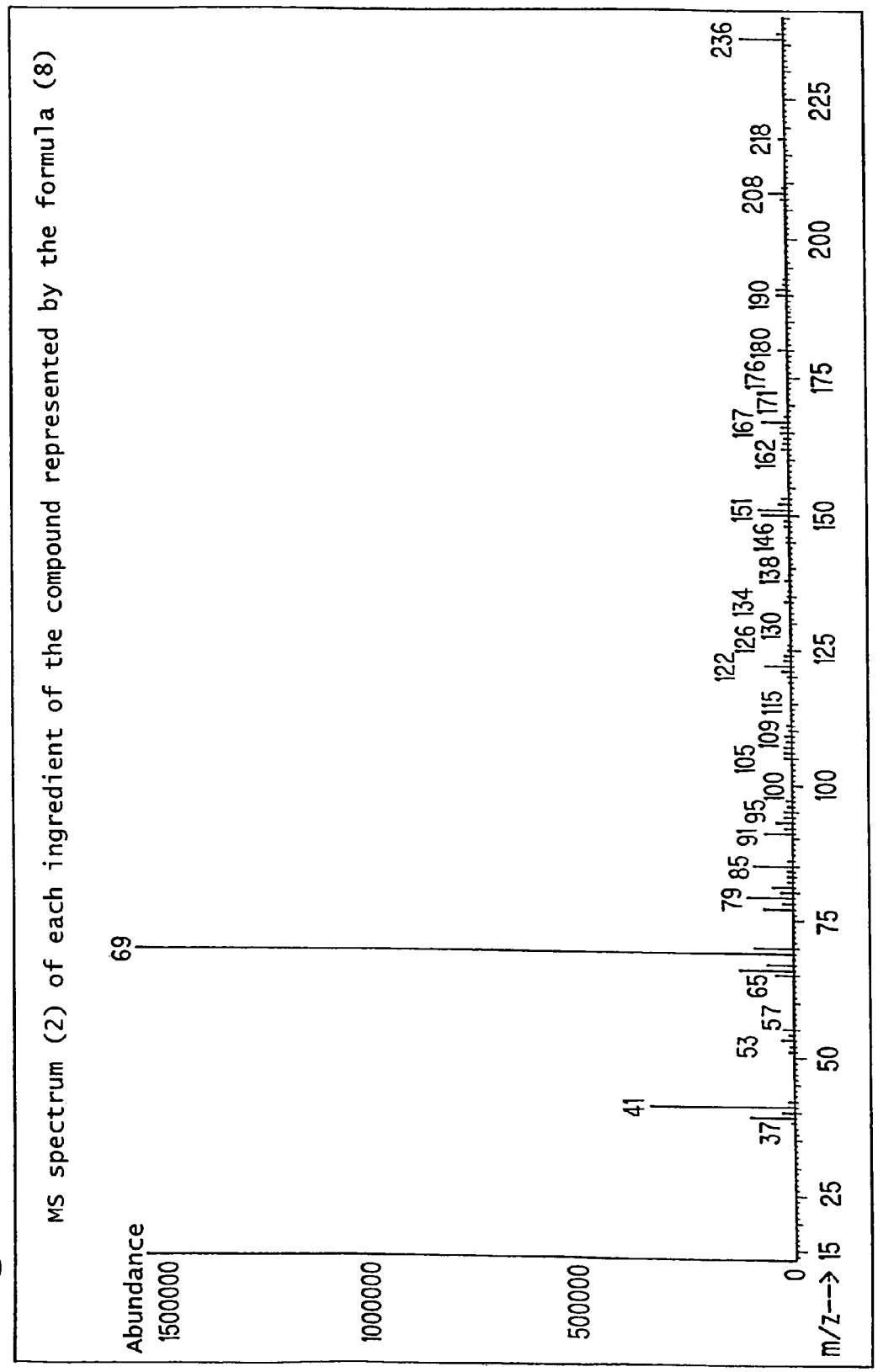
FIG. 7 is an MS spectrum (2) of each ingredient of the compound represented by the formula (8), which was obtained in Example. A2.
Figure 8:
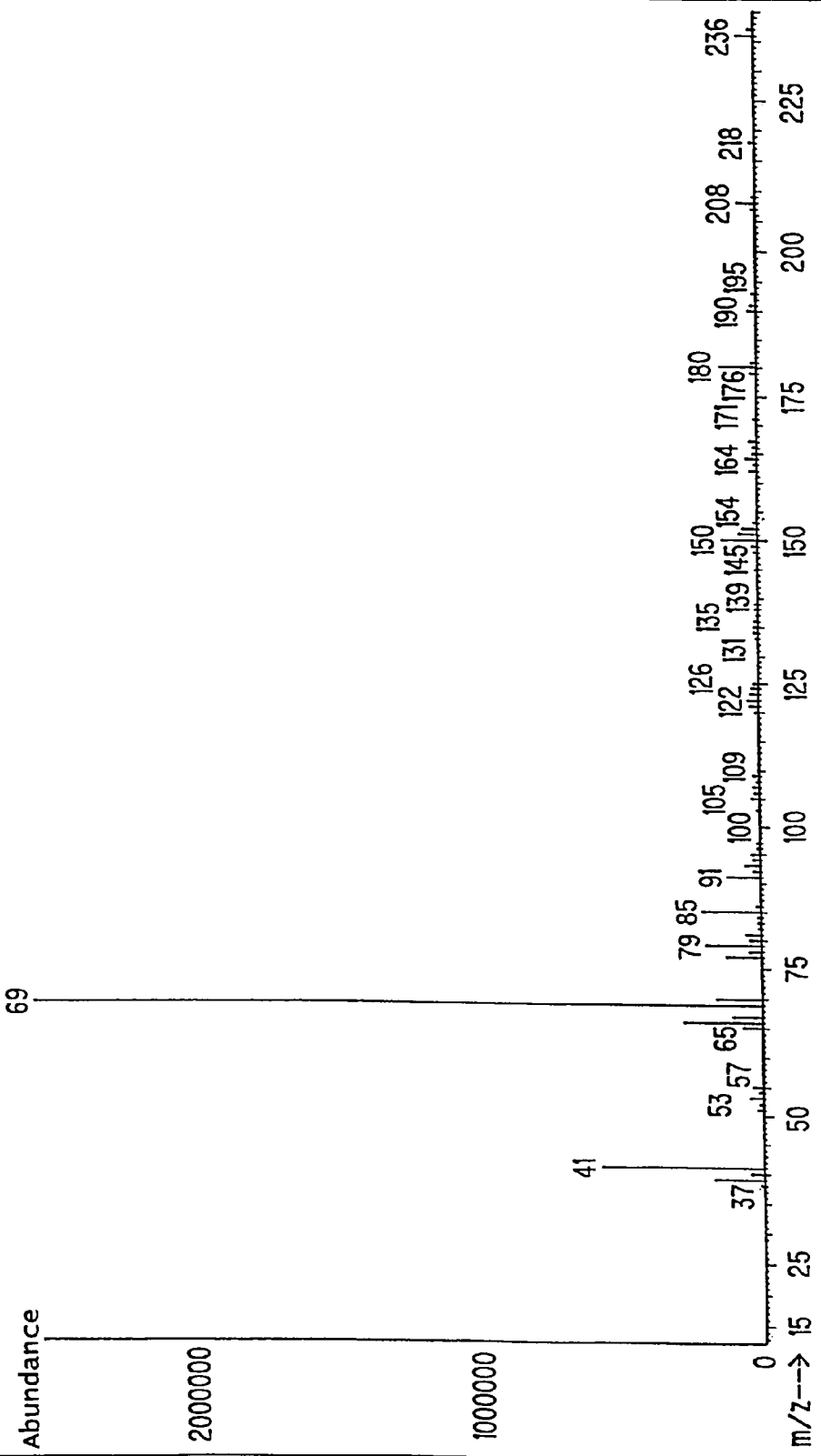
FIG. 8 is an MS spectrum (3) of each ingredient of the compound represented by the formula (8), which was obtained in Example A2.
Figure 9:
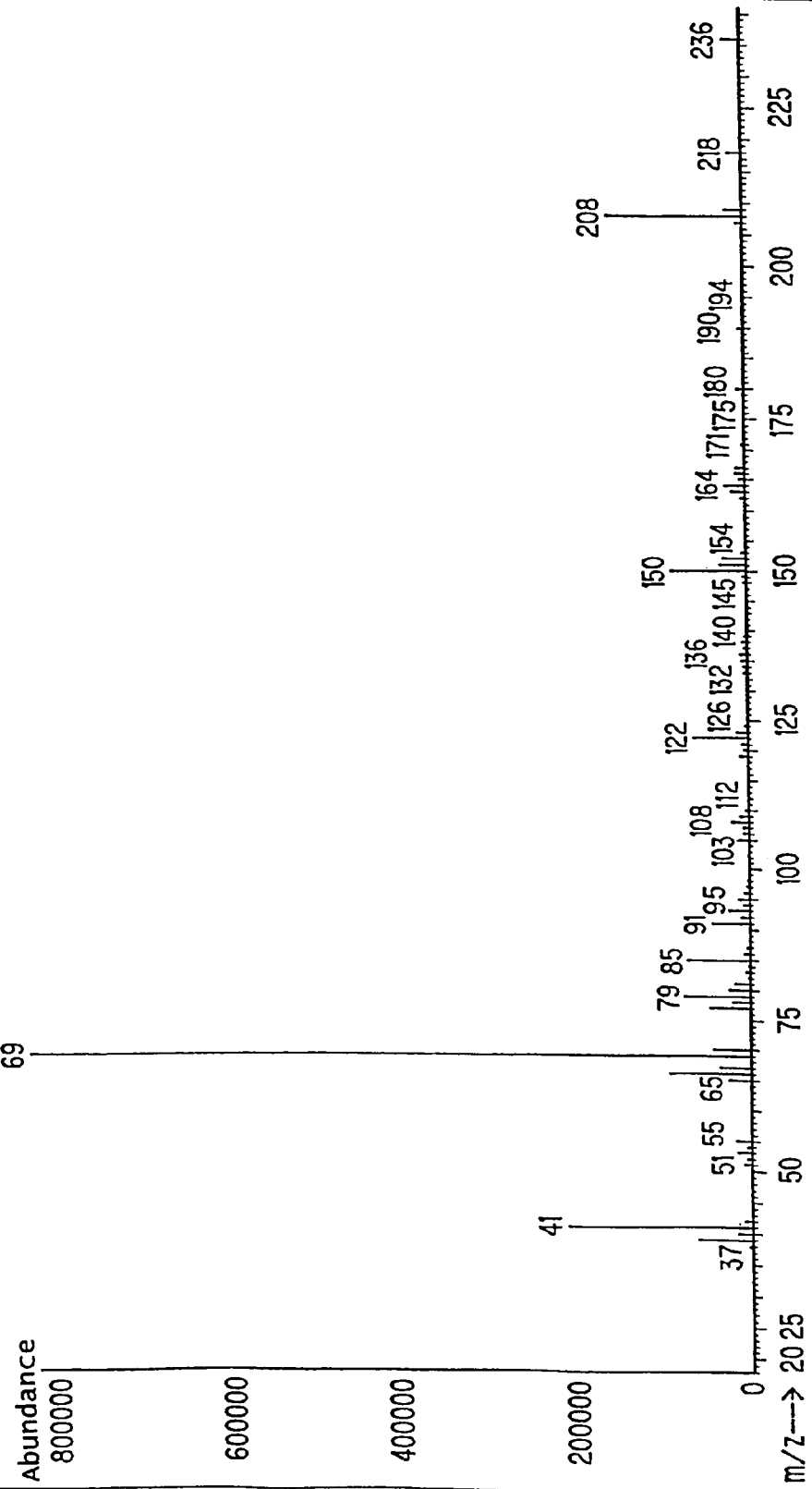
FIG. 9 is an MS spectrum (4) of each ingredient of the compound represented by the formula (8), which was obtained in Example A2.

The $^1$H-NMR spectrum of the compound of formula (8) obtained in Example A2 is shown in FIG. 4, and the $^{13}$C-NMR spectrum of the same compound is shown in FIG. 5. Each of FIGS. 6, 7, 8 and 9 shows the MS spectrum of each ingredient of the same compound.

The thus obtained (meth)acrylate of the present invention was evaluated in terms of solubility.

The obtained compound of formula (8) was dissolved in various solvents as shown in Table 1 at room temperature, and the preparation of a 25% by weight solution was attempted. All of the solvents used in the evaluation had been purified. Moreover, as Comparative Example A1, the solubility of 5-methacryloyloxy-6-hydroxybicyclo[2.2.1]heptane-2-carboxylic-6-lactone was also evaluated in the same manner. The results are shown in Table 1. The solubility was evaluated as follows:

◯: a homogenous transparent solution was obtained

Δ: an emulsion was generated, or a small amount of precipitate was deposited x: the compound was completely separated in two phases, or a large amount of precipitate was deposited

TABLE 1

| Solvent | Example A2 | Comparative Example A1 |
|---|---|---|
| tetrahydrofuran | ◯ | Δ |
| 2-acetoxy-1-methoxypropane | ◯ | x |
| 1,4-dioxane | ◯ | Δ |
| N,N-dimethylformamide | ◯ | ◯ |

It was found that the compound of formula (8) that is the (meth)acrylate of the present invention is more excellent than the compound of comparative Example A1 in solubility in organic solvents.

Example A3

Production example of a mixture (hereinafter referred to as the compound of formula (9) or OTDA) of 8-acryloyloxy-4-oxatricyclo[5.2.1.0$^{2,6}$]decane-3-one and 9-acryloyloxy-4-oxatricyclo[5.2.1.0$^{2,6}$]decane-3-one, which is represented by the following formula (9):

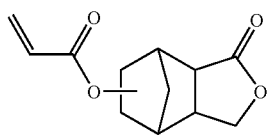

(9)

8.4 g (0.05 mol) of the compound of formula (7) produced in Example A1 and 40 ml of dry dichloromethane were placed in a glass flask equipped with an agitator, two dropping funnels, a thermometer and a Dimroth condenser. 6.6 g (0.065 mol) of triethylamine was placed in one dropping funnel, and 5.4 g (0.06 mol) of chloride acrylate was placed in the other dropping funnel. The inside of the flask was substituted by nitrogen, and the system was set at about −5° C. While stirring the inside of the flask, triethylamine and chloride acrylate were dropped thereto over 1 hour, so that the amount of triethylamine was slightly excessive to that of chloride acrylate. This time, a little heat-generation was observed. After completion of the dropping, 0.1 g (0.001 mol) of dimethylaminopyridine was added thereto, and the mixture was stirred for 24 hours, while the inside of the system naturally returned to room temperature. Thereafter, 35 ml of methanol was carefully added to the reaction solution, and the mixture was washed with water and a saturated sodium hydrogen carbonate solution in succession. Thereafter, the mixture was dried with magnesium sulfate, and the solvent was distilled off, so as to obtain a crude compound of formula (9). The compound was then purified by silica gel column chromatography so as to obtain 9.3 g (0.042 mol, yield: 84%) of the compound of formula (9). It should be noted that the compound of formula (9) may become a mixture of isomers depending on whether the acryloyloxy group is an endo-orientation or exo-orientation.

Figure 10:
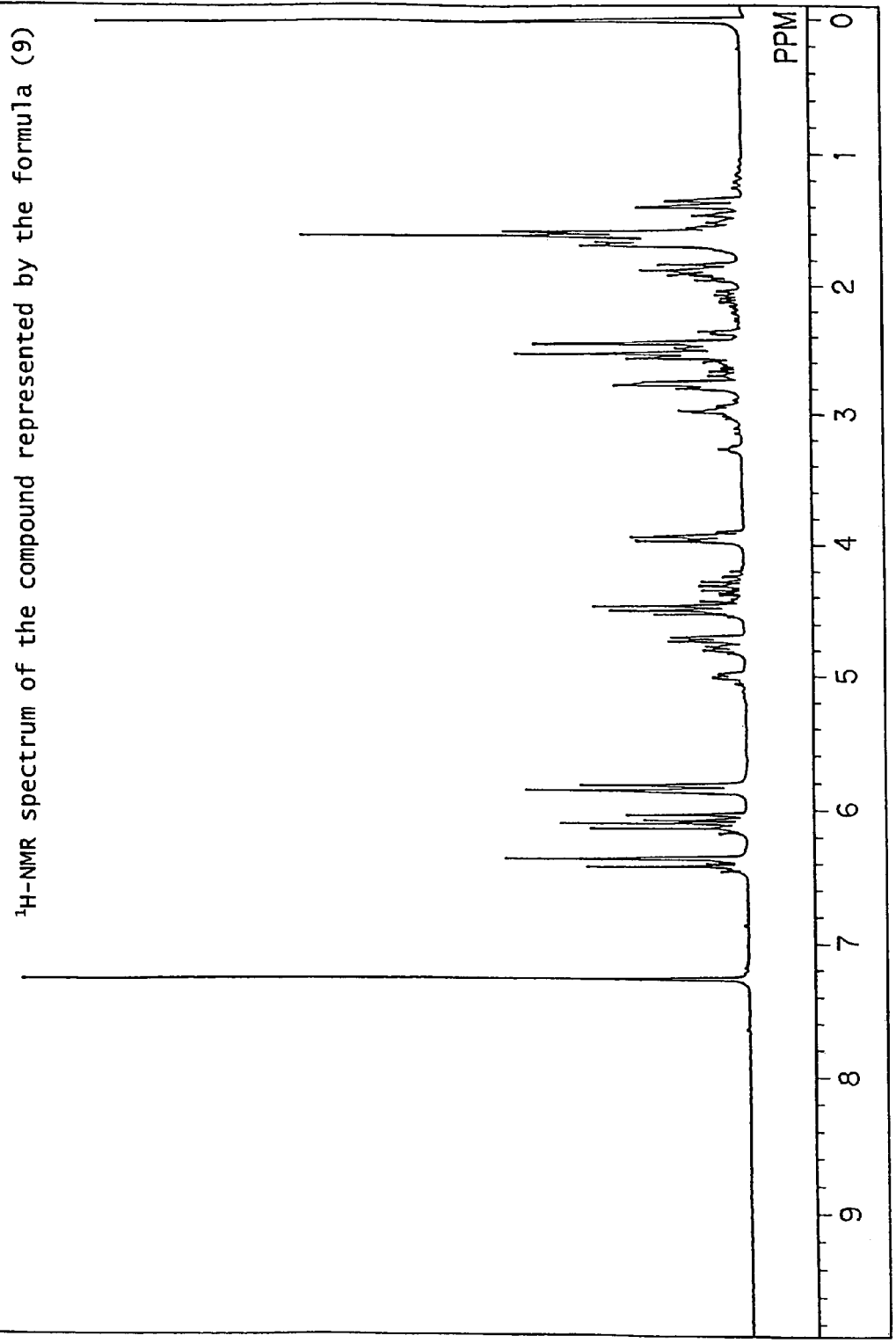
FIG. 10 is a $^1$H-NMR spectrum of the compound represented by a formula (9), which was obtained in Example A3.
Figure 11:
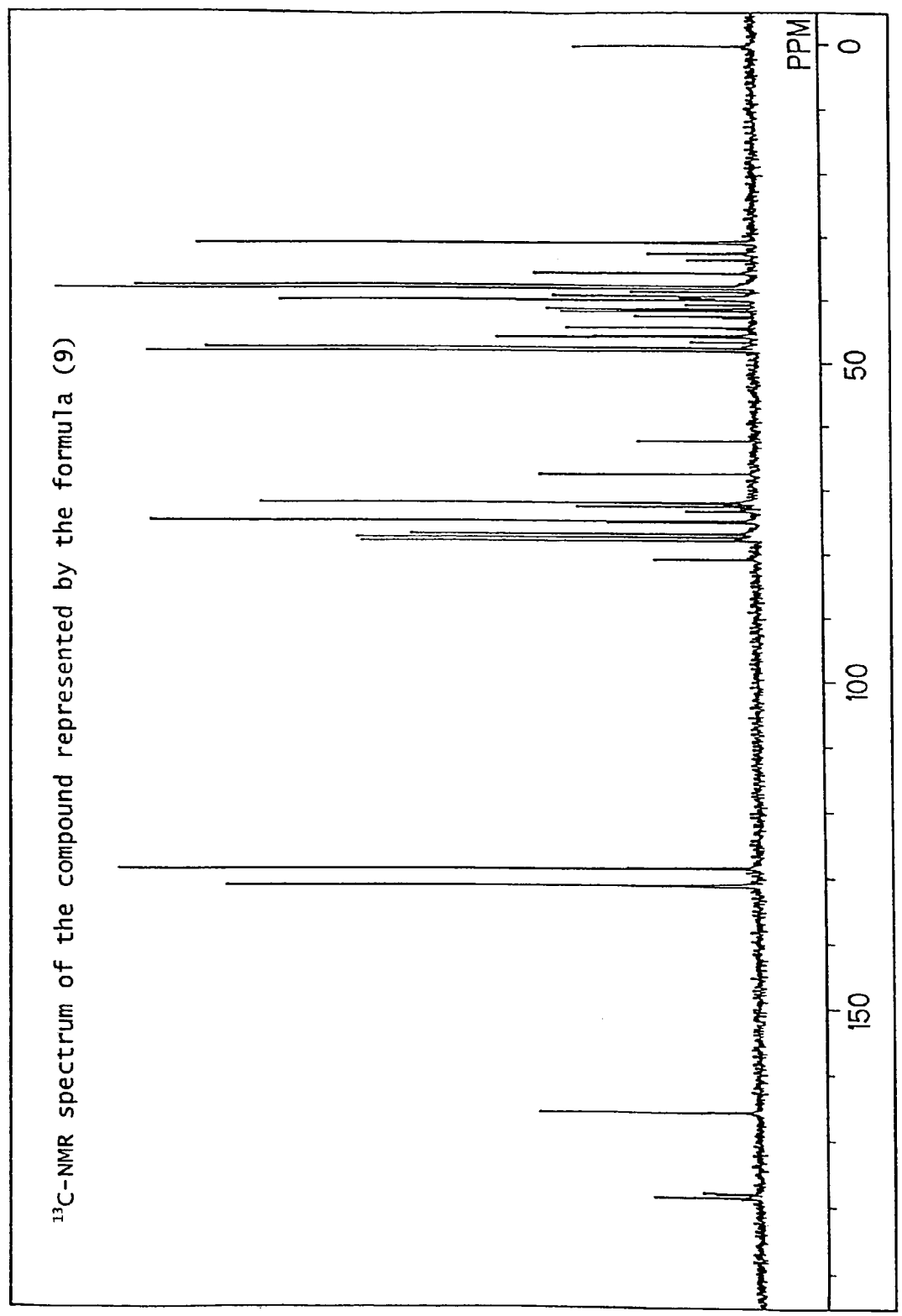
FIG. 11 is a $^{13}$C-NMR spectrum of the compound represented by the formula (9), which was obtained in Example A3.
Figure 12:
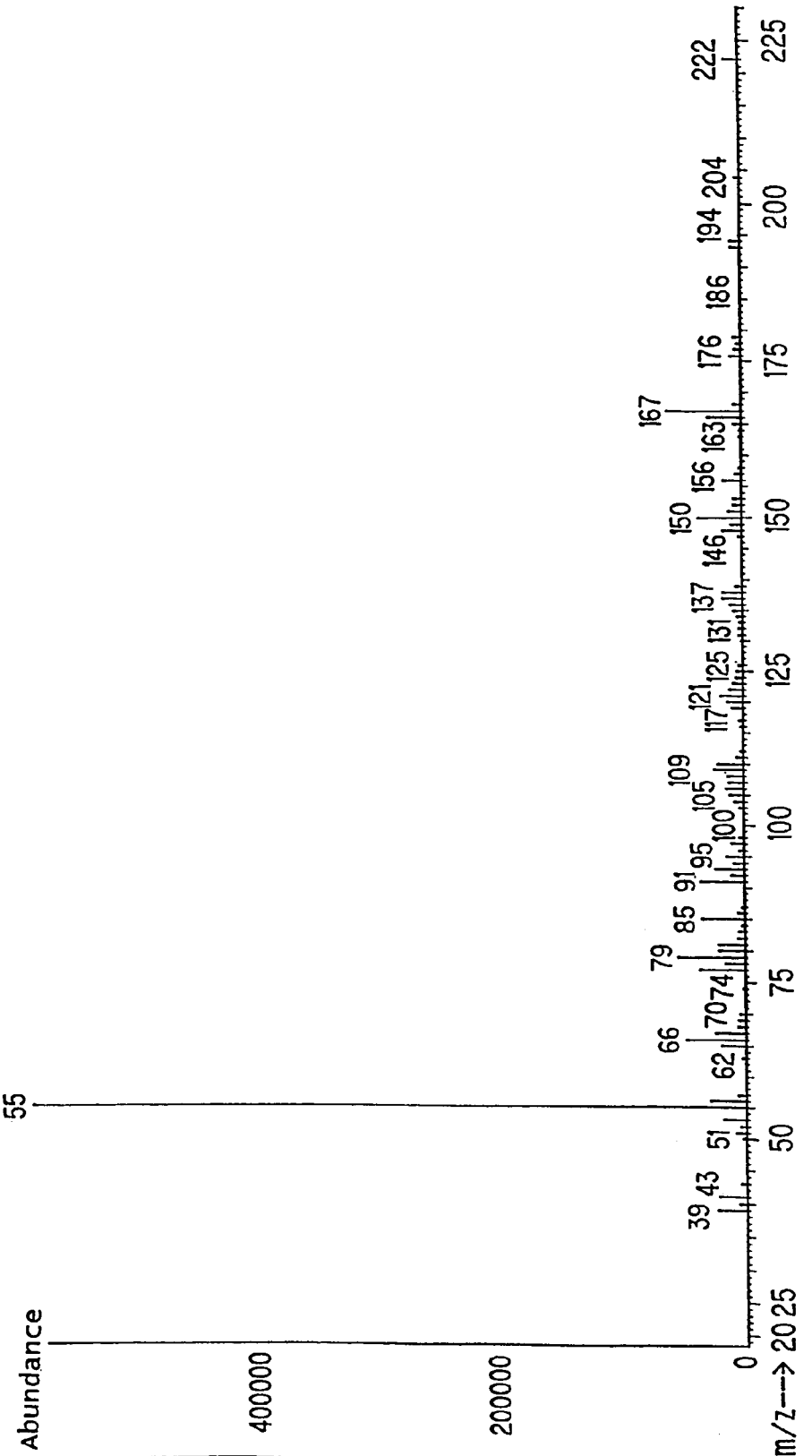
FIG. 12 is an MS spectrum (1) of each ingredient of the compound represented by the formula (9), which was obtained in Example A3.
Figure 13:
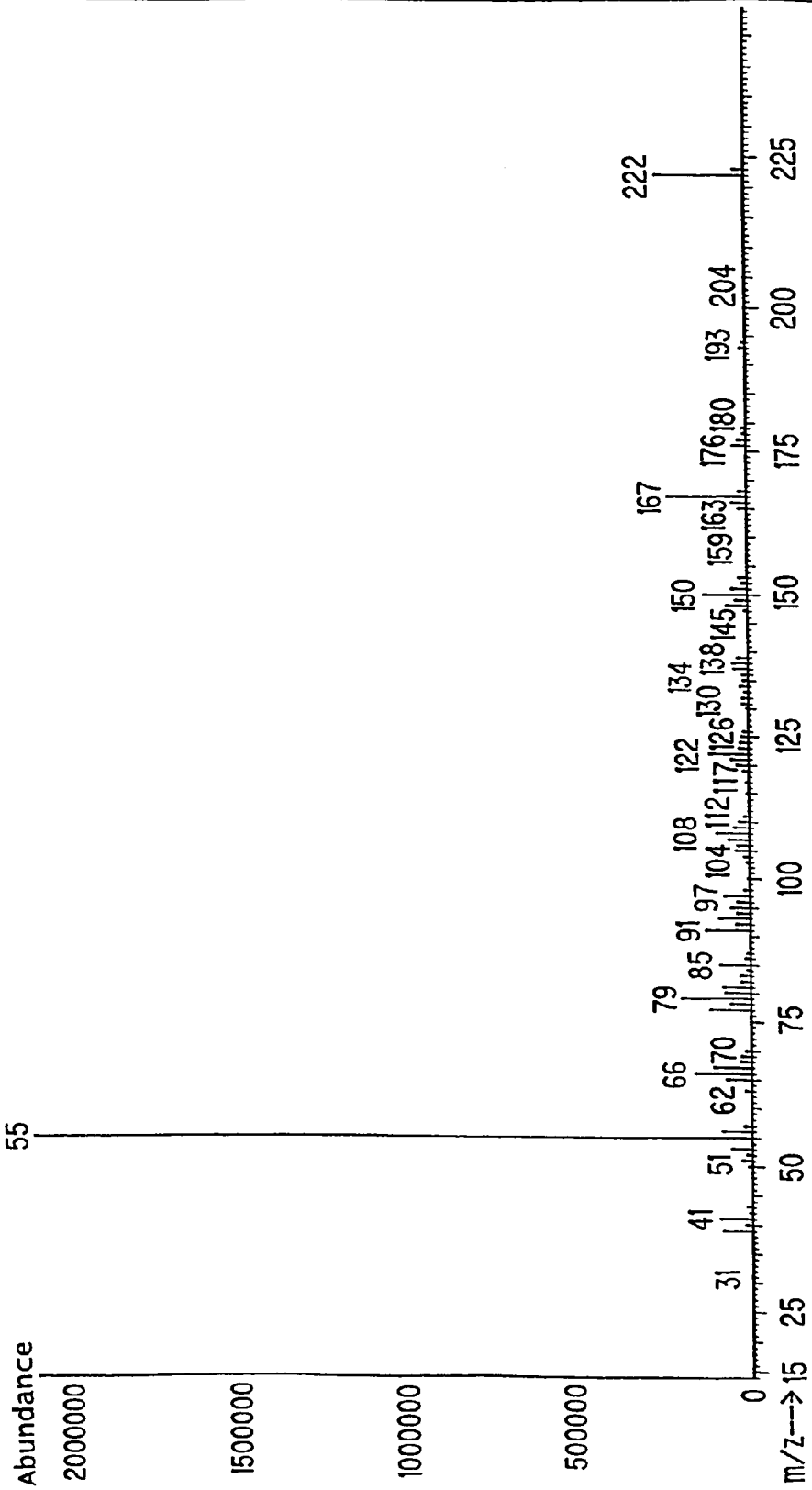
FIG. 13 is an MS spectrum (2) of each ingredient of the compound represented by the formula (9), which was obtained in Example A3.
Figure 14:
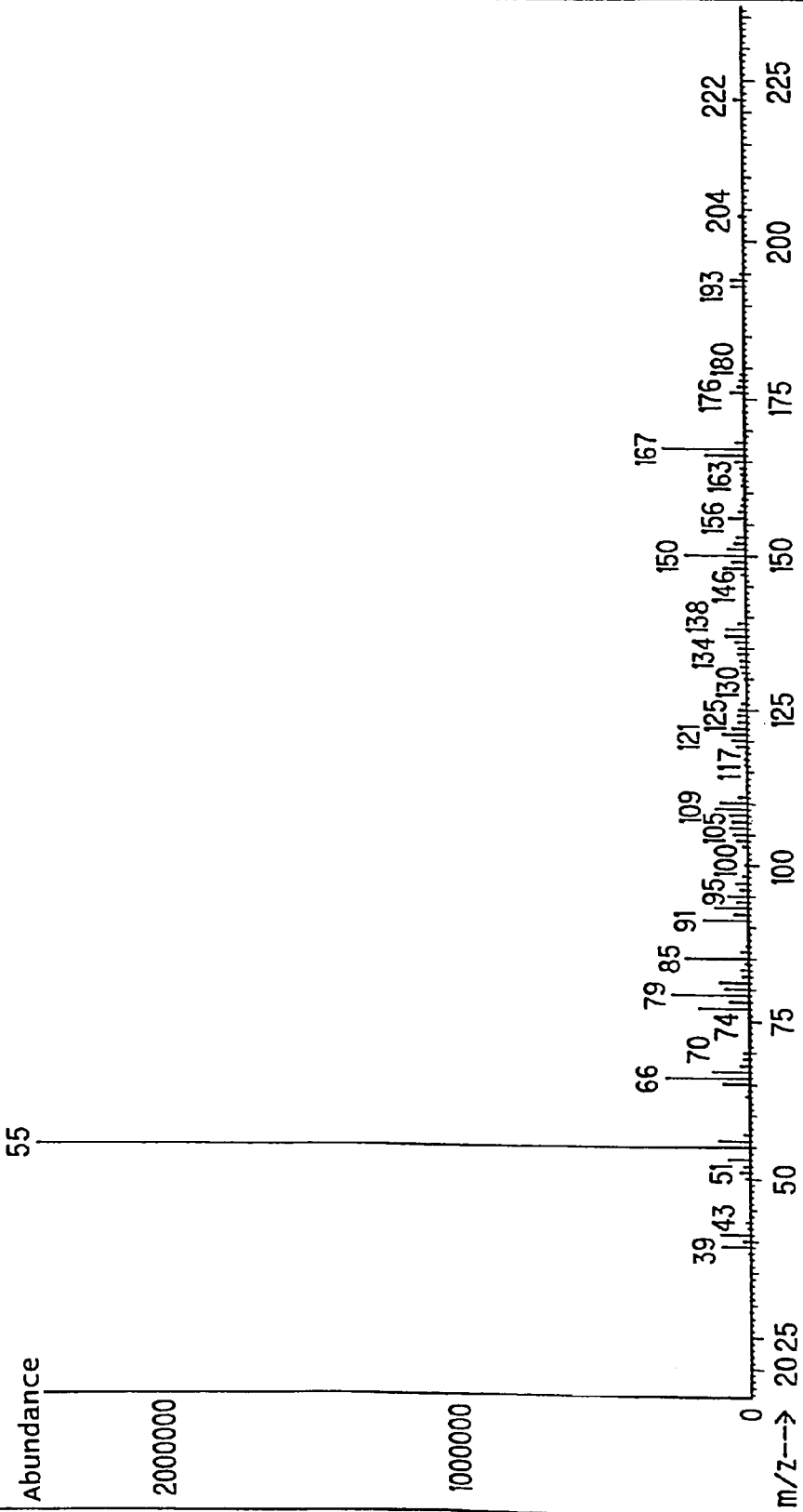
FIG. 14 is an MS spectrum (3) of each ingredient of the compound represented by the formula (9), which was obtained in Example A3.

The $^1$H-NMR spectrum of the compound of formula (9) obtained in Example A3 is shown in FIG. 10, and the $^{13}$C-NMR spectrum of the same compound is shown in FIG. 11. Each of FIGS. 12, 13, 14 and 15 shows the MS spectrum of each ingredient of the same compound.

Example A4

Production example of a mixture (hereinafter referred to as the compound of formula (10)) of 8-methacryloyloxy-8-methyl-4-oxatricyclo[5.2.1.0$^{2,6}$]decane-3-one, 8-methacryloyloxy-1-,-7-,-10-methyl-4-oxatricyclo[5.2.1.0$^{2,6}$]decane-3-one, 9-methacryloyloxy-9-methyl-4-oxatricyclo[5.2.1.0$^{2,6}$]decane-3-one, and 9-methacryloyloxy-1-,-7-,-10-methyl-4-oxatricyclo[5.2.1.0$^{2,6}$]decane-3-one, which is represented by the following formula (10):

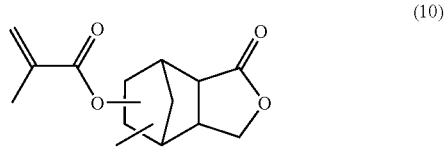

(10)

Reduction of an acid anhydride, addition of formic acid to double bond, and hydrolysis of formate were carried out in the same manner as in Example A1 with the exception that a transparent yellow liquid methyl-5-norbornene-2,3-dicarboxylic anhydride (Wako Pure Chemical Industries, Ltd.) was used instead of 5-norbornene-2,3-dicarboxylic anhydride (Wako Pure Chemical Industries, Ltd.). The obtained alcohol was subjected to an esterification reaction with methacryloyl chloride in the same manner as in Example A2, so as to obtain the compound of formula (10).

Example A5

Production example of a mixture (hereinafter referred to as the compound of formula (11)) of 7-methacryloyloxy-3-oxabicyclo[4.3.0]nonane-2-one and 8-methacryloyloxy-3-oxabicyclo[4.3.0]nonane-2-one, which is represented by the following formula (11):

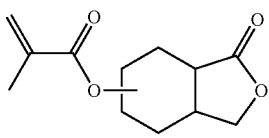

(11)

Reduction of an acid anhydride, addition of formic acid to double bond, and hydrolysis of formate were carried out in the same manner as in Example A1 with the exception that a white solid tetrahydrophthalic anhydride (Kanto Kagaku) was used instead of 5-norbornene-2,3-dicarboxylic anhydride (Wako Pure Chemical Industries, Ltd.). The obtained alcohol was subjected to an esterification reaction with methacryloyl chloride in the same manner as in Example A2, so as to obtain the compound of formula (11).

Example A6

Production example of a mixture (hereinafter referred to as the compound of formula (12)) of 8-methacryloyloxy-4,10-dioxatricyclo[5.2.1.0$^{2,6}$]decane-3-one and 9-methacryloyloxy-4,10-dioxatricyclo[5.2.1.0$^{2,6}$]decane-3-one, which is represented by the following formula (12):

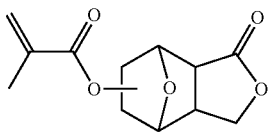

(12)

Reduction of an acid anhydride, addition of formic acid to double bond, and hydrolysis of formate were carried out in the same manner as in Example A1 with the exception that a white solid exo-3,6-epoxy-1,2,3,6-tetrahydrophthalic anhydride (Aldrich) was used instead of 5-norbornene-2,3-dicarboxylic anhydride (Wako Pure Chemical Industries, Ltd.). The obtained alcohol was subjected to an esterification reaction with methacryloyl chloride in the same manner as in Example A2, so as to obtain the compound of formula (12).

Example A7

Production example of a mixture (hereinafter referred to as the compound of formula (13)) of 8-methacryloyloxy-4-oxatricyclo[5.2.2.0$^{2,6}$]undecane-3-one and 9-methacryloyloxy-4-oxatricyclo[5.2.2.0$^{2,6}$]undecane-3-one, which is represented by the following formula (13):

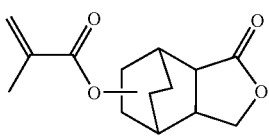

(13)

Reduction of an acid anhydride, addition of formic acid to double bond, and hydrolysis of formate were carried out in the same manner as in Example A1 with the exception that a white solid endo-bicyclo[2.2.2]oct-5-ene-2,3-dicarboxylic anhydride (Aldrich) was used instead of 5-norbornene-2,3-dicarboxylic anhydride (Wako Pure Chemical Industries, Ltd.). The obtained alcohol was subjected to an esterification reaction with methacryloyl chloride in the same manner as in Example A2, so as to obtain the compound of formula (13).

Example A8

Production example of a mixture (hereinafter referred to as the compound of formula (14)) of 7-methyl-3-oxabicyclo[4.3.0]-7-nonen-2-one and 8-methyl-3-oxabicyclo[4.3.0]-7-nonen-2-one, which is represented by the following formula (14):

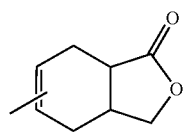

(14)

49.0 g (0.5 mol) of maleic anhydride, 0.05 g of p-methoxyphenol, and 600 ml of N,N-dimethylacetamide were placed in a flask equipped with an agitator and a thermometer, and they were dissolved. 34.1 g (0.5 mol) of isoprene was dropped thereto at room temperature over 10 minutes. While stirring, reaction was carried out at room temperature for 6 hours. After 6 hours, the flask was placed in an ice water bath, so that the system was cooled to 0° C. to 10° C. While paying attention so that the temperature did not rise to 40° C. or higher, 21.0 g (0.5 mol) of sodium boron hydride was added thereto drop by drop followed by stirring for 12 hours. After completion of the stirring, while paying attention to the heat of neutralization and foaming, 6N hydrochloric acid was added thereto so that the solution became pH 2, and it was then left for 6 hours. Thereafter, the reaction solution was extracted with toluene, the combined organic extracts were washed with water followed by drying with sodium sulfate, and the solvent was distilled off, so as to obtain 51.5 g (0.31 mol, yield: 62%) of the white solid compound of formula (14).

Example A9

Production example of a mixture (hereinafter referred to as the compound of formula (15)) of 7-methacryloyloxy-7-methyl-3-oxabicyclo[4.3.0]nonane-2-one and 8-methacryloyloxy-8-methyl-3-oxabicyclo[4.3.0]nonane-2-one, which is represented by the following formula (15):

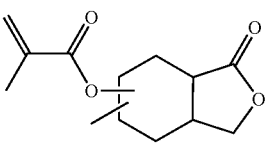

(15)

Addition of formic acid to double bond and hydrolysis of formate were carried out in the same manner as in Example A1 with the exception that the compound of formula (14) produced in Example A8 was used instead of 5-norbornene-2,3-dicarboxylic anhydride (Wako Pure Chemical Industries, Ltd.). The obtained alcohol was subjected to an esterification reaction with methacryloyl chloride in the same manner as in Example A2, so as to obtain the compound of formula (15).

Example A10

Production Example of the Compound of Formula (8)

16.8 g (0.10 mol) of the compound of formula (7) produced in Example A1, 200.2 g (0.15 mol) of methacrylic anhydride, pyridine (0.16 mol), 0.01 g of p-methoxyphenol, and 75 g of 2-butanone were placed in a glass flask equipped with an agitator, a thermometer and a Dimroth condenser. While air was introduced thereinto at 5 ml/min, the mixture was stirred at a reaction temperature of 50° C. for 12 hours in an oil bath. Thereafter, while maintaining the temperature, 12.5 g (0.4 mol) of methanol was carefully added thereto followed by stirring for 3 hours. Thereafter, a low-boiling fraction was removed from the reaction solution, and water was added thereto followed by extraction with ethyl acetate. The combined organic extracts were washed with a 20% potassium carbonate solution, a saturated ammonium chloride solution and a saturated solution of salt followed by drying with magnesium sulfate, and the solvent was distilled off, so as to obtain a crude compound of formula (8). The compound was then purified by silica gel column chromatography, so as to obtain 15.4 g (0.065 mol, yield: 65%) of the compound of formula 8 that was a transparent liquid.

Example A11

Production Example of the Compound of Formula (8)

17.2 g (0.2 mol) of methacrylic acid, 1.9 g (0.01 mol) of p-toluenesulfonic acid monohydrate, 0.01 g of p-methoxyphenol, and 200 g of tetrahydrofuran were placed in a glass flask equipped with an agitator, a thermometer, a dropping funnel, a decanter and a Dimroth condenser. The inside of the flask was stirred, and while air was introduced thereinto at 5 ml/min, the system was heated under reflux in an oil bath. Thereafter, 16.8 g (0.10 mol) of the compound of formula (7) produced in Example A1 was dissolved in 100 g of tetrahydrofuran. The obtained solution was placed in the dropping funnel, and it was then dropped in the system over 2 hours. After completion of the dropping, while eliminating water generated as a result of the reaction as well as tetrahydrofuran by azeotropic elimination, esterification was carried out at a reaction temperature of 75° C. for 8 hours. After completion of the reaction, the reaction solution was cooled to room temperature, and a 10% sodium hydroxide solution was added thereto to neutralize the catalyst. After washing the reaction solution with a 20% potassium carbonate solution, a saturated ammonium chloride solution and a saturated saline solution, it was dried with magnesium sulfate, and the solvent was distilled off, so as to obtain a crude compound of formula (8). The compound was then purified by silica gel column chromatography, so as to obtain 11.1 g (0.047 mol, yield: 47%) of the compound of formula (8) that was a transparent liquid.

Example A12

Production Example of the Compound of Formula (8)

16.8 g (0.10 mol) of the compound of formula (7) produced in Example A1, 200.2 g (2.0 mol) of methyl methacrylate, and 0.03 g of p-methoxyphenol were placed in a glass flask equipped with an agitator, a thermometer and an oldershaw. The mixture was heated under reflux at a reaction temperature of 105° C. for 2 hours in an oil bath, and the generated water was then removed. Thereafter, the reaction solution was cooled, 3.61 g (0.01 mol) of dioctyltin oxide was added thereto, and transesterification was carried out by heating the mixture under reflux at a reaction temperature of 105° C. for 12 hours. After completion of the reaction, the reaction solution was cooled to room temperature, and methyl methacrylate was removed, so as to obtain a crude compound of formula (8). The compound was then purified by silica gel column chromatography, so as to obtain 13.2 g (0.056 mol, yield: 56%) of the compound of formula (8) that was a transparent liquid.

Example A13

Production Example of the Compound of Formula (8)

22.3 g (0.53 mol) of sodium boron hydroxide and 344.0 g of DMF were placed in a 3-L round flask equipped with an agitator, a thermometer and a dropping funnel, and the mixture was stirred at room temperature so as to dissolve sodium boron hydroxide. Thereafter, the internal temperature was cooled to 0° C. to 5° C. in an ice bath. Separately, 161.6 g (0.984 mol) of a white solid 5-norbornene-2,3-dicarboxylic anhydride (Wako Pure Chemical Industries, Ltd.) and 242.4 g of DMF were placed in a 500 ml beaker, and the mixture was fully stirred so that the solid was completely dissolved. Thereafter, the mixture was transferred to the above dropping funnel, and it was dropped, while paying attention so that the internal temperature of the flask was controlled within a range of 5° C. to 30° C. After completion of the dropping, stirring was further continued for 2 hours in an ice bath. Thereafter, 1.5 L of water was added thereto, while paying attention so that the internal temperature of the flask was controlled within a range of 5° C. to 30° C., and then concentrated sulfuric acid was added thereto until the pH became 0.5. The obtained mixture was extracted twice with MIBK. This time, the water layer was well separated from the organic layer. Thereafter, the combined organic layers were washed with water, and they were then concentrated with an evaporator. The obtained concentrate was analyzed by gas chromatography using a capillary column HP-5 (Hewlett-Packard). As a result, 133.2 g (0.887 mol) of 4-oxatricyclo[5.2.1.0$^{2,6}$]decen-3-one was obtained at a yield of 90%. Moreover, in the concentrate, MIBK represented 42% to the total mass.

Subsequently, a reaction to add lower carboxylic acid was carried out without isolating a lactone from a concentrate.

245.8 g of the concentrate (containing 131.8 g (0.877 mol) of 4-oxatricyclo[5.2.1.0$^{2,6}$]decen-3-one and 102.5 g of MIBK) and 312.2 g (6.51 mol) of formic acid were placed in a 2-L round flask equipped with an agitator, a condenser and a thermometer, and the mixture was stirred. Thereafter, while taking care of heating, 26.3 g (0.17 mol) of trifluoromethanesulfonic acid was slowly added thereto. The temperature of the liquid was set at 100° C. in an oil bath, and it was stirred for 6 hours. Thereafter, the reaction solution was cooled to room temperature, and an aliquot of the content was analyzed by gas chromatography. As a result, 103.3 g (0.526 mol) of a mixture of 8-formyloxy-4-oxatricyclo[5.2.1.0$^{2,6}$]decane-3-one and 9-formyloxy-4-oxatricyclo[5.2.1.0$^{2,6}$]decane-3-one was obtained at a yield of 60%.

Subsequently, 820 ml of a 15% sodium chloride solution was added to the reaction solution, and the mixture was stirred at room temperature (25° C.) for 2 hours for hydrolysis. The resulting product was extracted twice with MIBK, and the combined organic extracts were washed with a 15% sodium chloride solution and a saturated sodium hydrogen carbonate solution. Thereafter, it was concentrated using an evaporator at 30° C. to 50° C. at 6.7 kPa until MIBK was not remained. The obtained concentrate was subjected to a forced agitation thin film evaporator under conditions of 130° C. to 140° C. and 130 to 400 Pa, so that 68.0 g (0.403 mol) of the compound of formula (7) was obtained at a yield of 46%.

16.8 g (0.10 mol) of the obtained compound of formula (7) and 80 ml of dry dichloromethane were placed in a flask equipped with an agitator, two dropping funnels, a thermometer and a condenser. 13.2 g (0.13 mol) of triethylamine was placed in one dropping funnel, and 12.5 g (0.12 mol) of methacryloyl chloride was placed in the other dropping funnel. The inside of the flask was substituted by nitrogen, and the system was set at about −5° C. While stirring the inside of the flask, triethylamine and methacryloyl chloride were dropped thereto over 1 hour, so that the amount of triethylamine was slightly excessive to that of methacryloyl chloride. This time, a little heat-generation was observed. After completion of the dropping, 0.3 g of dimethylaminopyridine was added thereto, and the mixture was stirred for 18 hours, while the inside of the system naturally returned to room temperature. Thereafter, 100 ml of methanol was carefully added to the reaction solution, and the mixture was washed with water and a saturated sodium hydrogen carbonate solution in succession. Thereafter, the mixture was dried with magnesium sulfate, and the solvent was distilled off, so as to obtain a crude compound of formula (8). The compound was then purified by silica gel column chromatography, so that 15.0 g (0.063 mol) of the compound of formula (8) that was a transparent liquid was obtained at a yield of 63%.

Example A14

Production Example of the Compound of Formula (10)

283.6 g of an MIBK solution containing methyl-4-oxatricyclo[5.2.1.0$^{2,6}$]decen-3-one was obtained in the same manner as in Example A13 with the exception that 143.9 g (0.807 mol) of methyl-5-norbornene-2,3-dicarboxylic anhydride (Wako Pure Chemical Industries, Ltd.) was used instead of 5-norbornene-2,3-dicarboxylic anhydride. The concentrate was analyzed by gas chromatography, and as a result, 114.4 g (0.697 mol) of methyl-4-oxatricyclo[5.2.1.0$^{2,6}$]decen-3-one was obtained at a yield of 86%, and in the concentrate, MIBK represented 56% to the total mass.

Subsequently, 49.4 g (0.271 mol) of a mixture (hereinafter referred to as a mixture A) of methyl-8-hydroxy-4-oxatricyclo[5.2.1.0$^{2,6}$]decane-3-one and methyl-9-hydroxy-4-oxatricyclo[5.2.1.0$^{2,6}$]decane-3-one that was a transparent liquid was obtained at a yield of 40% in the same manner as in Example A13 with the exception that 278.0 g of the above MIBK solution (containing 112.1 g (0.683 mol) of methyl-4-oxatricyclo[5.2.1.0$^{2,6}$]decen-3-one and 155.9 g of MIBK) was used.

Thereafter, 15.3 g (0.061 mol) of the compound of formula (10) that was a transparent liquid was obtained at a yield of 61% in the same manner as in Example A13 with the exception that 18.2 g (0.10 mol) of the mixture A was used.

Reference Example 1

Production Example of the Compound of Formula (8)

Using 164.0 g (1.00 mol) of 5-norbornene-2,3-dicarboxylic anhydride, reduction was carried out in the same manner as in Example A13. Thereafter, water was added to the reaction solution, and hydrochloric acid was further added thereto until pH became 0.5. The mixture was extracted twice with hexane, and the combined organic extracts were washed with water. When the hexane layer was separated from the water layer, an emulsion layer appeared in the interface, and therefor the separation was significantly difficult. Although the hexane layer was concentrated with an evaporator until no evaporated products were evaporated, a product of interest could not be isolated. In the analysis of DMF concentration by gas chromatography, remaining DMF represented 15% to the total mass. So as to eliminate the DMF, hexane and water were added to the flask, and after fully stirring, the mixture was separated in layers. The hexane layer was subjected to an evaporator again to concentrate it until no evaporated products were evaporated. After the operation to eliminate the DMF was repeated twice, the concentration of remaining DMF represented 3% to the total mass. This time, it was observed that a highly adhesive white solid was present in the flask, and the removal of this solid was difficult. This solid was analyzed by gas chromatography, and as a result, 67.6 g (0.450 mol) of 4-oxatricyclo[5.2.1.0$^{2,6}$]decen-3-one was obtained at a yield of 45%. When compared with Example A13, the yield was significantly decreased, and further, the operation became more complicated.

Subsequently, using 60.0 g (0.399 mol) of the 4-oxatricyclo[5.2.1.0$^{2,6}$]decen-3-one, in the same manner as in Example A13, 45.5 g (0.232 mol) of a mixture of 8-formyloxy-4-oxatricyclo[5.2.1.0$^{2,6}$]decane-3-one and 9-formyloxy-4-oxatricyclo[5.2.1.0$^{2,6}$]decane-3-one was obtained at a yield of 58%. Then, hydrolysis was carried out thereon in the same manner as in Example A1, and 29.9 g (0.178 mol) of the compound of formula (7) was obtained at a yield of 44%.

Thereafter, using 16.8 g (0.10 mol) of the compound of formula (7), in the same manner as in Example A1, 14.2 g (0.06 mol, yield: 60%) of the compound of formula (8) was obtained.

Example A15

Production Example of the Compound of Formula (9)

12.9 g (0.058 mol, yield: 58%) of the compound of formula (9) that was a transparent liquid was obtained in the same manner as in Example A13 with the exception that 10.9 g (0.12 mol) of chloride acrylate was used instead of 12.5 g (0.12 mol) of methacryloyl chloride.

Example A16

Production Example of the Compound of Formula (8)

16.8 g (0.10 mol) of the compound of formula (7) produced in Example A13, 200.2 g of methyl methacrylate, and 0.03 g of p-methoxyphenol were placed in a glass flask equipped with an agitator, a thermometer and an oldershaw. The mixture was heated under reflux at a reaction temperature of 105° C. for 2 hours in an oil bath, and the generated water was then removed. Thereafter, the reaction solution was cooled, 3.61 g (0.01 mol) of dioctyl tin oxide was added thereto, and transesterification was carried out by heating the mixture under reflux at a reaction temperature of 105° C. for 8 hours. After completion of the reaction, the reaction solution was cooled to room temperature, and methyl methacrylate was removed, so as to obtain a crude compound of formula (8). The compound was then purified by silica gel column chromatography, so as to obtain 13.2 g (0.056 mol, yield: 56%) of the compound of formula (8).

Example A17

18.0 kg of DMF and 1.17 kg (27.8 mol) of sodium boron hydride were placed in a 200 L glass lining reaction tank equipped with a jacket and an agitator, and sodium boron hydride was dissolved by stirring. Thereafter, brine was supplied to the jacket, and the inside of the tank was set at a temperature of 0° C. to 5° C. Moreover, nitrogen gas started to be supplied at 0.1 L/min from the end of the tank. 8.46 kg (51.5 mol) of a commercially available 5-norbornene-2,3-dicarboxylic anhydride and 12.7 kg of DMF were placed in a 25 L dissolution tank, and 5-norbornene-2,3-dicarboxylic anhydride was completely dissolved by stirring. Using a proportioning pump, the prepared DMF solution comprising 5-norbornene-2,3-dicarboxylic anhydride was fed to the reaction tank, while paying attention so that the internal temperature of the tank did not exceed 30° C. After completion of the feeding, while maintaining the internal temperature of the tank at 5° C. to 15° C., stirring was continued for 2 hours. 80 kg of water was slowly fed thereto so that the internal temperature did not exceed 30° C. Then, concentrated sulfuric acid was slowly fed thereto until the pH became 0.5, and stirring was continued for 3 hours. Subsequently, the supply of nitrogen gas was stopped, the solution was extracted twice with 40 kg of MIBK, and the combined organic extracts were washed with 45 kg of water. The organic layers were concentrated at 50° C. at 6.6 kPa, until the MIBK concentration in the solution became about 50% by weight. An aliquot of the concentrate was collected, and it was analyzed by gas chromatography. As a result, 6.90 kg (45.9 mol) of 4-oxatricyclo[5.2.1.0$^{2,6}$]decen-3-one was obtained at a yield of 89%. The MIBK concentration was 57%. Thereafter, the content in the tank was transferred to a 25 L container. This time, the solution had good flowability, and so the solution was eliminated from the reaction tank without any problem.

Subsequently, 21.8 kg (454.7 mol) of formic acid was poured into the same 200 L glass lining reaction tank, and while stirring, 0.7 kg (4.57 mol) of trifluoromethanesulfonic acid was slowly added. Then, the mixture was heated to 100° C. 17.2 kg of a concentrate (containing 6.83 kg (45.5 mol) of 4-oxatricyclo[5.2.1.0$^{2,6}$]decen-3-one and 9.7 kg of MIBK) was dropped in the mixture over 4 hours, using a proportioning pump. After completion of the dropping, while maintaining the temperature at 100° C., stirring was continued for 2 hours. An aliquot of the reaction solution was taken, and it was analyzed by gas chromatography. As a result, 6.69 kg (34.1 mol) of a mixture of 8-formyloxy-4-oxatricyclo[5.2.1.0$^{2,6}$]decane-3-one and 9-formyloxy-4-oxatricyclo[5.2.1.0$^{2,6}$]decane-3-one was obtained at a yield of 75%.

Subsequently, 55 kg of a 15% sodium chloride solution was added, and the obtained mixture was stirred at 15° C. to 20° C. for 2 hours for hydrolysis. Then, the solution was extracted twice with 28 kg of MIBK, and the combined organic extracts were washed with 22 kg of a 15% sodium chloride solution and 22 kg of a saturated sodium hydrogen carbonate solution. The organic layers were subjected to vacuum distillation at 50° C. at 6.7 kpa, so that they were concentrated until no MIBK was distilled. Using a forced agitation thin film evaporator with an area of heat transferring surface (or interface) area of 0.1 m², treatment was carried out at 130° C. to 140° C. at 130 to 530 Pa, so as to obtain 4.40 kg (26.2 mol) of the compound of formula (7) at a yield of 58%.

Subsequently, 23.5 kg of dichloromethane and 4.20 kg (25.0 mol) of the compound of formula (7) were placed in the same glass lining reaction tank followed by stirring. The inside of the tank was substituted by nitrogen, and it was cooled with brine so that the system was set at about −5° C. 3.13 kg (29.6 mol) of methacryloyl chloride and 3.28 kg (32.1 mol) of triethylamine were fed to the system with a proportioning pump over 2 hours, so that the amount of triethylamine was slightly excessive to that of methacryloyl chloride. After completion of the feeding, 0.06 kg of dimethylaminopyridine was added, and stirring was carried on for 11 hours, while the inside of the system naturally returned to room temperature. 19 kg of methanol was added to the reaction solution, and the mixture was then washed with 20 kg of water and 20 kg of a saturated sodium hydrogen carbonate solution. The organic layer was subjected to distillation at 45° C. to 60° C. at 101.3 kpa, so that they were concentrated until no solvents were distilled off. Using a forced agitation thin film evaporator with an electrothermal area of 0.1 m², treatment was carried out at 130° C. to 140° C. at 133 Pa or lower, so as to obtain 3.54 kg (15.0 mol) of the compound of formula (8) at a yield of 60%.

Example B1

Production of the polymer represented by the following formula (16) (wherein, in the above formula (5-1), each of $R^5$ and $R^7$ represents a methyl group, each of $R^1$ to $R^4$ represents a hydrogen atom, $R^6$ represents a 2-methyl-2-adamantyl group, $A^1$, $A^2$=-CH$_2$—, $X^2$=0.5, $Y^2$=0.5, and $Z^2$=0)

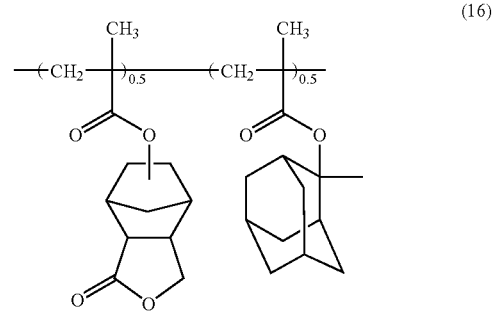

(16)

30.0 parts of ethyl lactate was placed in a separable flask equipped with a nitrogen introduction port, an agitator, a condenser and a thermometer in a nitrogen atmosphere, and while stirring, the temperature of a hot water bath was raised to 80° C. A monomer solution obtained by mixing 13.33 parts of OTDMA, 13.22 parts of 2-methacryloyloxy-2-methyladamantane (hereinafter referred to as MAdMA), 30.0 parts of ethyl lactate, and 0.21 parts of azobisisobutyronitrile was dropped in the flask at a certain rate over 6 hours, and then the temperature of 80° C. was kept for 2 hours. Thereafter, while stirring, the obtained reaction solution was dropped in 800 parts of methanol, so as to obtain a white precipitate. The obtained precipitate was filtered and dried under a reduced pressure at 60° C. for approximately 10 hours. Thereafter, the precipitate was dissolved in 45 parts of tetrahydrofuran, and while stirring, the obtained solution was dropped in 800 parts of methanol. The obtained precipitate was filtered and dried under a reduced pressure at 60° C. for approximately 40 hours.

Subsequently, the properties of the obtained product were measured. According to GPC analysis, weight-average molecular weight (hereinafter referred to as MW) was 13900, dispersity (hereinafter referred to as Mw/Mn) was 1.60, and copolymerization ratio was OTDMA:MAdMA=50:50 according to the integration ratio of $^1$H-NMR ($X^2$=0.5, $Y^2$=0.5, and $Z^2$=0).

Example B2

Production of the polymer represented by the following formula (17) (wherein, in the above formula (5-1), each of $R^1$ to $R^5$ and $R^7$ represents a hydrogen atom, $R^6$ represents a 2-methyl-2-adamantyl group, $A^1$, $A^2$=-CH$_2$—, $X^2$=0.5, $Y^2$=0.5, and $Z^2$=0)

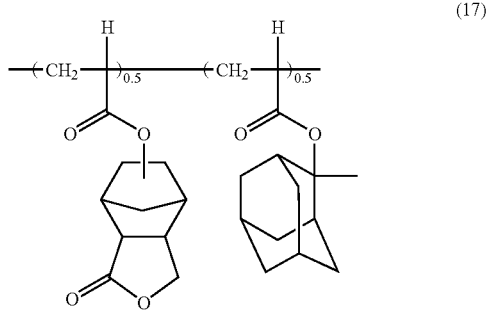

(17)

Synthesis was carried out in the same manner as in Example B1 with the exception that 12.54 parts of OTDA was used instead of 13.33 parts of OTDMA in Example B1 and 12.43 parts of 2-acryloyloxy-2-methyladamantane (hereinafter referred to as MAdA) was used instead of 13.22 parts of MAdMA in Example B1, so as to obtain a copolymer.

The properties of the obtained copolymer were measured. According to GPC analysis, Mw was 14500, Mw/Mn was 1.43, and copolymerization ratio was OTDA:MAdA=50:50 according to the integration ratio of $^1$H-NMR ($X^2$=0.5, $Y^2$=0.5, and $Z^2$=0).

Example B3

Production of the polymer represented by the following formula (18) (wherein, in the above formula (5-1), each of $R^5$and $R^7$ represents a methyl group, each of $R^1$ to $R^4$ represents a hydrogen atom, $R^6$ represents a 2-ethyl-2-adamantyl group, $A^1$, $A^2$=-CH$_2$—, $X^2$=0.5, $Y^2$=0.5, and $Z^2$=0)

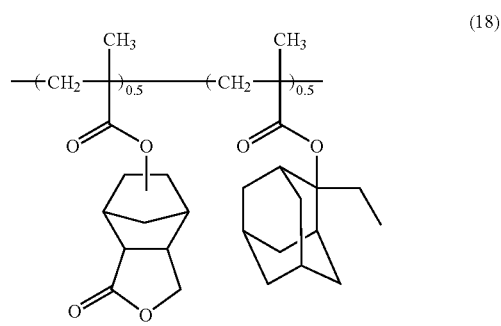

(18)

Synthesis was carried out in the same manner as in Example B1 with the exception that 14.01 parts of 2-methacryloyloxy-2-ethyladamantane (hereinafter referred to as EAdMA) was used instead of 13.22 parts of MAdMA in Example B1, so as to obtain a copolymer.

The properties of the obtained copolymer were measured. According to GPC analysis, Mw was 11300, Mw/Mn was 1.38, and copolymerization ratio was OTDMA:EAdMA=50:50 according to the integration ratio of $^1$H-NMR ($X^2$=0.5, $Y^2$=0.5, and $Z^2$=0).

Example B4

Production of the polymer represented by the following formula (19) (wherein, in the above formula (5-1), each of $R^5$and $R^7$ represents a methyl group, each of $R^1$ to $R^4$ represents a hydrogen atom, $R^6$ represents a 2-(1-adamantyl) propyl group, $A^1$, $A^2$=-CH$_2$—, $X^2$=0.5, $Y^2$=0.5, and $Z^2$=0)

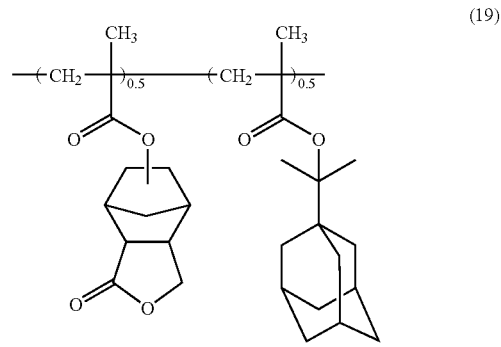

(19)

Synthesis was carried out in the same manner as in Example B1 with the exception that 14.83 parts of 1-(1-methacryloyloxy-1-methylethyl)adamantane (hereinafter referred to as IAdMA) was used instead of 13.22 parts of MAdMA in Example B1, so as to obtain a copolymer.

The properties of the obtained copolymer were measured. According to GPC analysis, MW was 10700, Mw/Mn was-1.45, and copolymerization ratio was OTDMA:IAdMA=50:50 according to the integration ratio of $^1$H-NMR ($X^2$=0.5, $Y^2$=0.5, and $Z^2$=0).

Example B5

Production of the polymer represented by the following formula (20) (wherein, in the above formula (5-1), each of $R^5$, $R^7$ and $R^9$ represents a methyl group, each of $R^1$ to $R^4$ represents a hydrogen atom, $R^6$ represents a 2-methyl-2-adamantyl group, $R^8$ represents a 2-hydroxyethyl group, $A^1$, $A^2$=-$CH_2$—, $X^2$=0.4, $Y^2$=0.5, and $Z^2$=0.1)

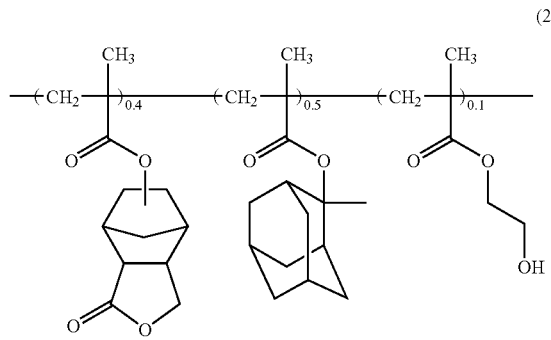

(20)

30.0 parts of ethyl lactate was placed in a separable flask equipped with a nitrogen introduction port, an agitator, a condenser and a thermometer in a nitrogen atmosphere, and while stirring, the temperature of a hot water bath was raised to 80° C. A monomer solution obtained by mixing 10.67 parts of OTDMA, 13.22 parts of MAdMA, 1.47 parts of 2-hydroxyethyl methacrylate (hereinafter referred to as HEMA), 30.0 parts of ethyl lactate, and 0.21 parts of azobisisobutyronitrile was dropped in the flask at a certain rate over 6 hours, and then the temperature of 80° C. was kept for 2 hours. Thereafter, while stirring, the obtained reaction solution was dropped in 800 parts of methanol, so as to obtain a white precipitate. The obtained precipitate was filtered and dried under a reduced pressure at 60° C. for approximately 10 hours. Thereafter, the precipitate was dissolved in 45 parts of tetrahydrofuran, and while stirring, the obtained solution was dropped in 800 parts of methanol. The obtained precipitate was filtered and dried under a reduced pressure at 60° C. for approximately 40 hours.

The properties of the obtained copolymer were measured. According to GPC analysis, Mw was 8500, Mw/Mn was 1.71, and copolymerization ratio was OTDMA:MAdMA:HEMA=40:50:10 according to the integration ratio of $^1$H-NMR ($X^2$=0.4, $Y^2$=0.5, and $Z^2$=0.1).

Example B6

Production of the polymer represented by the following formula (21) (wherein, in the above formula (5-1), each of $R^5$, $R^7$ and $R^9$ represents a methyl group, each of $R^1$ to $R^4$ represents a hydrogen atom, $R^6$ represents a 2-methyl-2-adamantyl group, $R^8$ represents a 3-hydroxy-1-adamantyl group, $A^1$, $A^2$=-$CH_2$—, $X^2$=0.4, $Y^2$=0.5, and $Z^2$=0.1)

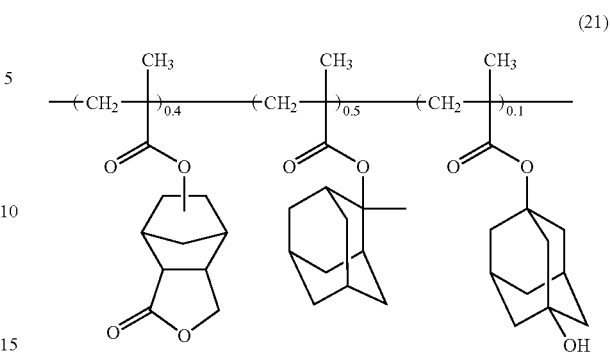

(21)

Synthesis was carried out in the same manner as in Example B5 with the exception that 2.67 parts of 1-methacryloyloxy-3-hydroxyadamantane (hereinafter referred to as HAdMA) was used instead of 1.47 parts of HEMA in Example B5, so as to obtain a copolymer.

The properties of the obtained copolymer were measured. According to GPC analysis, MW was 12400, Mw/Mn was 1.61, and copolymerization ratio was OTDMA:MAdMA:HAdMA=40:50:10 according to the integration ratio of $^1$H-NMR ($X^2$32 0.4, $Y^2$=0.5, and $Z^2$=0.1).

Example B7

Production of the polymer represented by the following formula (22) (wherein, in the above formula (5-1), each of $R^5$, $R^7$ and $R^9$ represents a methyl group, each of $R^1$ to $R^4$ represents a hydrogen atom, $R^6$ represents a 2-methyl-2-adamantyl group, $R^8$ represents a 3-(4-butanolide) group, $A^1$, $A^2$=-$CH_2$—, $X^2$=0.4, $Y^2$=0.5, and $Z^2$=0.1)

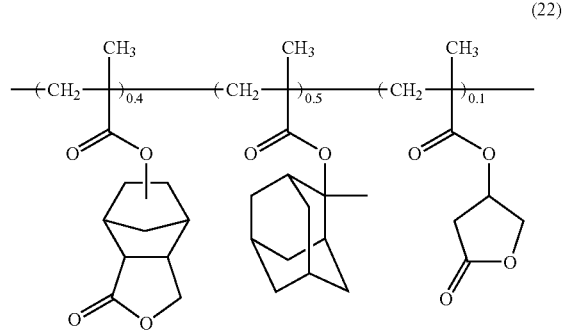

(22)

Synthesis was carried out in the same manner as in Example B5 with the exception that 1.92 parts of β-methacryloyloxy-γ-butyrolactone (hereinafter referred to as HGBMA) was used instead of 1.47 parts of HEMA in Example B5, so as to obtain a copolymer.

The properties of the obtained copolymer were measured. According to GPC analysis, Mw was 9600, Mw/Mn was 1.64, and copolymerization ratio was OTDMA:MAdMA:HGBMA=40:50:10 according to the integration ratio of $^1$H-NMR ($X^2$=0.4, $Y^2$=0.5, and $Z^2$=0.1).

Example B8

Production of the polymer represented by the following formula (23) (wherein, in the above formula (5-1), each of $R^5$, $R^7$ and $R^9$ represents a methyl group, each of $R^1$ to $R^4$ represents a hydrogen atom, $R^6$ represents a 2-methyl-2-adamantyl group, $R^8$ represents a 2-(4-butanolide) group, $A^1$, $A^2$=-$CH_2$—, $X^2$=0.4, $Y^2$=0.5, and $Z^2$=0.1)

(23)

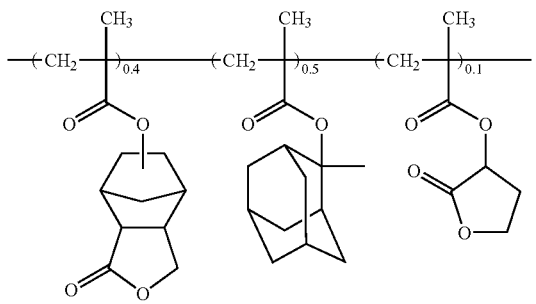

Synthesis was carried out in the same manner as in Example B5 with the exception that 1.92 parts of α-methacryloyloxy-γ-butyrolactone (hereinafter referred to as GBLMA) was used instead of 1.47 parts of HEMA in Example B5, so as to obtain a copolymer.

The properties of the obtained copolymer were measured. According to GPC analysis, Mw was 8200, Mw/Mn was 1.52, and copolymerization ratio was OTDMA:MAdMA:GBLMA=40:50:10 according to the integration ratio of $^1$H-NMR ($X^2$=0.4, $Y^2$=0.5, and $Z^2$=0.1).

Example B9

Production of the polymer represented by the following formula (24) (wherein, in the above formula (5-1), each of $R^5$, $R^7$ and $R^9$ represents a methyl group, each of $R^1$ to $R^4$ and $R^8$ represents a hydrogen atom, $R^6$ represents a 2-methyl-2-adamantyl group, $A^1$, $A^2$=-$CH_2$—, $X^2$=0.4, $Y^2$=0.5, and $Z^2$=0.1)

(21)

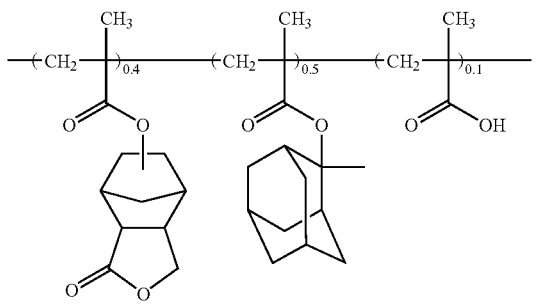

Synthesis was carried out in the same manner as in Example B5 with the exception that 0.97 parts of methacrylic acid (hereinafter referred to as MAA) was used instead of 1.47 parts of HEMA in Example B5, so as to obtain a copolymer.

The properties of the obtained copolymer were measured. According to GPC analysis, Mw was 7300, Mw/Mn was 1.77, and copolymerization ratio was OTDMA:MAdMA:MAA=40:50:10 according to the integration ratio of $^1$H-NMR ($X^2$=0.4, $Y^2$=0.5, and $Z^2$=0.1).

Example B10

Production of the polymer represented by the following formula (25) (wherein, in the above formula (5-2), each of $R^5$ and $R^7$ represents a methyl group, each of $R^1$ to $R^4$ represents a hydrogen atom, $R^6$ represents a 2-methyl-2-adamantyl group, $A^1$, $A^2$=-$CH_2$—, $X^3$=0.4, $Y^3$=0.5, and $Z^3$=0.1)

(25)

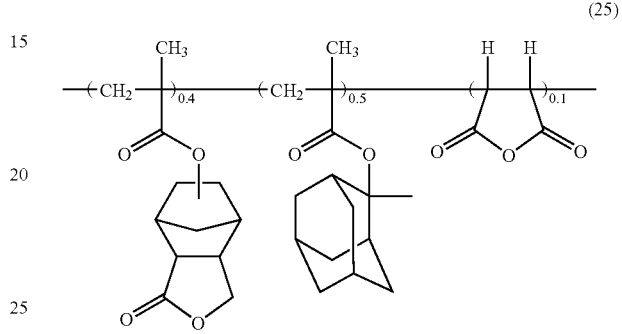

Synthesis was carried out in the same manner as in Example B5 with the exception that 1.10 parts of maleic anhydride (hereinafter referred to as MA) was used instead of 1.47 parts of HEMA in Example B5, so as to obtain a copolymer.

The properties of the obtained copolymer were measured. According to GPC analysis, Mw was 7800, Mw/Mn was 1.48, and copolymerization ratio was OTDMA:MAdMA:MA=40:50:10 according to the integration ratio of $^1$H-NMR ($X^3$=0.4, $Y^3$=0.5, and $Z^3$=0.1).

Example B11

Production of the polymer represented by the following formula (26) (wherein, in the above formula (5-3), each of $R^1$ to $R^5$ and $R^7$ represents a hydrogen atom, each of $R^{10}$ and $R^{11}$ represents a methyl group, $R^6$ represents a 2-methyl-2-adamantyl group, $A^1$, $A^2$=-$CH_2$—, $X^4$=0.4, $Y^4$=0.5, and $Z^4$=0.1)

(26)

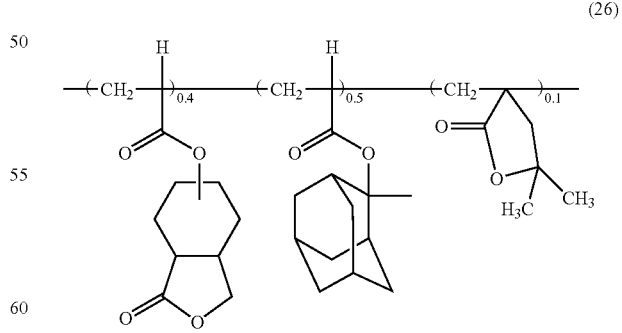

Synthesis was carried out in the same manner as in Example B5 with the exception that 10.03 parts of OTDA, 12.43 parts of MAdA, and 1.42 parts of 2-methylene-4,4-dimethyl-4-butanolide (hereinafter referred to as MDMBL) were used instead of 10.67 parts of OTDMA, 13.22 parts of MAdMA, and 1.47 parts of HEMA in Example B5, respectively, so as to obtain a copolymer.

The properties of the obtained copolymer were measured. According to GPC analysis, MW was 9200, Mw/Mn was 1.57, and copolymerization ratio was OTDA:MAdA:MD-MBL=40:50:10 according to the integration ratio of $^1$H-NMR ($X^4$=0.4, $Y^4$=0.5, and $Z^4$=0.1).

Example B12

Production of the polymer represented by the following formula (27) (wherein, in the above formula (5-3), each of $R^1$ to $R^5$ and $R^7$ represents a hydrogen atom, each of $R^{10}$ and $R^{11}$ represents a methyl group, $R^6$ represents a 2-ethyl-2-adamantyl group, $A^1$, $A^2$=-CH$_2$—, $X^4$=0.4, $Y^4$=0.5, and $Z^4$=0.1)

(27)

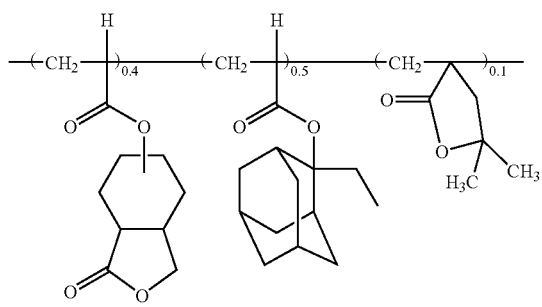

Synthesis was carried out in the same manner as in Example B11 with the exception that 13.17 parts of 2-acryloyloxy-2-ethyladamantane (hereinafter referred to as EAdA) was used instead of 12.43 parts of MAdA in the Example B11, so as to obtain a copolymer.

The properties of the obtained copolymer were measured. According to GPC analysis, Mw was 8800, Mw/Mn was 1.40, and copolymerization ratio was OTDA:EAdA:MD-MBL =40:50:10 according to the integration ratio of $^1$H-NMR ($X^4$=0.4, $Y^4$=0.5, and $Z^4$=0.1).

Example B13

Production of the polymer represented by the following formula (28) (wherein, in the above formula (5-3), each of $R^1$ to $R^5$ and $R^7$ represents a hydrogen atom, each of $R^{10}$ and $R^{11}$ represents a methyl group, $R^6$ represents a (2-(1-adamantyl)propyl group, $A^1$, $A^2$=-CH$_2$—, $X^4$=0.4, $Y^4$=0.5, and $Z^4$=0.1)

(28)

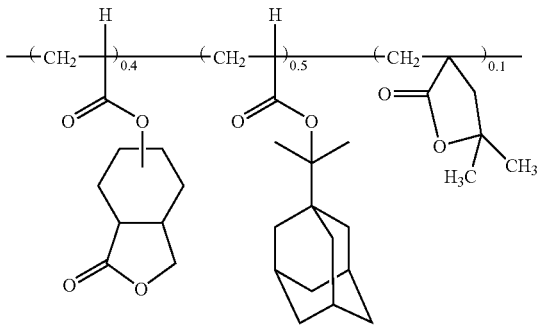

Synthesis was carried out in the same manner as in Example B11 with the exception that 13.94 parts of 1-(1-acryloyloxy-1-methylethyl)adamantane (hereinafter referred to as IAdA) was used instead of 12.43 parts of MAdA in the Example B11, so as to obtain a copolymer.

The properties of the obtained copolymer were measured. According to GPC analysis, MW was 8600, Mw/Mn was 1.55, and copolymerization ratio was OTDA:IAdA:MD-MBL=40:50:10 according to the integration ratio of $^1$H-NMR ($X^4$=0.4, $Y^4$32 0.5, and $Z^4$=0.1).

Comparative Example B1

Production of a Copolymer of 5-methacryloyloxy-6-hydroxybicyclo[2.2.1]heptane-2-carboxylic-6-lactone and 2-methacryloyloxy-2-methyladamantane 30.0 parts of acetonitrile was placed in a separable flask equipped with a nitrogen introduction port, an agitator, a condenser and a thermometer in a nitrogen atmosphere, and while stirring, the temperature of a hot water bath was raised to 80° C. Separately, 26.64 parts of 5-methacryloyloxy-6-hydroxybicyclo[2.2.1]heptane-2-carboxylic-6-lactone, 28.08 parts of MAdMA, 60.0 parts of ethyl lactate, and 0.86 parts of azobisisobutyronitrile were mixed. As a result, 5-methacryloyloxy-6-hydroxybicyclo[2.2.1]heptane-2-carboxylic-6-lactone was not dissolved. Thus, 60.0 parts of ethyl lactate was used instead of 60.0 parts of acetonitrile, so that a homogenous solution was obtained. The obtained homogenous solution was dropped in the flask at a certain rate over 6 hours, and then the temperature of 80° C. was kept for 2 hours. From 2 hours after initiation of the dropping of the monomer solution, a white polymer precipitate was observed in the reaction solution. Since the white polymer precipitate was not dissolved by the addition of 45 parts of tetrahydrofuran to the reaction solution, 1800 parts of tetrahydrofuran was further added thereto, and the precipitate was thereby dissolved. The obtained solution was dropped in 4000 parts of methanol, while stirring, so that a white precipitate was obtained. The obtained precipitate was filtered and dried under a reduced pressure at 60° C. for approximately 10 hours. The dried precipitate was dissolved in 2000 parts of tetrahydrofuran, and while stirring, the obtained solution was dropped in 5000 parts of methanol. The obtained precipitate was filtered and dried under a reduced pressure at 60° C. for approximately 40 hours.

The properties of the obtained copolymer were measured. According to GPC analysis, Mw was 9100, Mw/Mn was 1.51, and copolymerization ratio was 5-methacryloyloxy-6-hydroxybicyclo[2.2.1]heptane-2-carboxylic-6-lactone:MAdMA=50:50 according to the integration ratio of $^1$H-NMR.

Comparative Example B2

Production of a Copolymer of
β-methacryloyloxy-γ-butyrolactone and
2-methacryloyloxy-2-methyladamantane 15.0 parts of 1,4-dioxane was placed in a separable flask equipped with a nitrogen introduction port, an agitator, a condenser and a thermometer in a nitrogen atmosphere, and while stirring, the temperature of a hot water bath was raised to 80° C. A monomer solution obtained by mixing 9.61 parts of HGBMA, 13.22 parts of MAdMA, 30.0 parts of 1,4-dioxane and 0.21 parts of azobisisobutyronitrile was dropped in the flask at a certain rate over 6 hours, and then the temperature of 80° C. was kept for 2 hours. Thereafter, the obtained reaction solution was dropped in 800 parts of methanol, while stirring, so that a white precipitate was obtained. The obtained precipitate was filtered and dried under a reduced pressure at 60° C. for approximately 10 hours. The precipitate was dissolved in 45 parts of tetrahydrofuran, and while stirring, the obtained solution was dropped in 800 parts of methanol. The obtained precipitate was filtered and dried under a reduced pressure at 60° C. for approximately 40 hours.

The properties of the obtained copolymer were measured. According to GPC analysis, Mw was 11000, Mw/Mn was 1.68, and copolymerization ratio was HGBMA:MAdMA=50:50 according to the integration ratio of $^1$H-NMR.

Example B14

100 parts of the copolymer obtained in each of Examples B1 to B13 and comparative Examples B1 and B2 was dissolved in both 300 parts of ethyl lactate and 300 parts of propyleneglycol monomethyl ether acetate at room temperature, so that the preparation of a 25% by weight solution was attempted. The results are shown in Table 2.

TABLE 2

|  | Ethyl lactate | Propyleneglycol monomethyl ether acetate |
|---|---|---|
| Example B1 | ○ | ○ |
| Example B2 | ○ | ○ |
| Example B3 | ○ | ○ |
| Example B4 | ○ | ○ |
| Example B5 | ○ | ○ |
| Example B6 | ○ | ○ |
| Example B7 | ○ | ○ |
| Example B8 | ○ | ○ |
| Example B9 | ○ | ○ |
| Example B10 | ○ | ○ |
| Example B11 | ○ | ○ |
| Example B12 | ○ | ○ |
| Example B13 | ○ | ○ |
| Comparative Example B1 | x | x |
| Comparative Example B2 | ○ | ○ |

Symbols in the table mean as follows:
○: a homogenous transparent solution was obtained,
x: a precipitate was deposited.

Example B15

100 parts of the copolymer obtained in each of Examples B1 to B13 and comparative Examples B1 and B2, and 2 parts of triphenylsulfonium triflate were dissolved in 500 parts of propyleneglycol monomethyl ether acetate at room temperature so as to obtain a homogenous solution. Then, the solution was filtered through a Teflon filter so as to obtain a resist composition solution. Thereafter, each of the prepared composition solutions was spin-coated on a 3-inch silicon wafer, and using a hot plate, pre-bake was carried out at 120° C. for 60 seconds to form a thin film having a film thickness of 0.5 μm. Subsequently, the thin film was exposed using an ArF excimer laser exposure machine (wavelength: 193 nm), and then, using a hot plate, baking was carried out at 120° C. for 60 seconds. Thereafter, development was carried out at room temperature using a 2.38% by weight tetramethylammonium hydroxide solution followed by washing with pure water and drying, so as to form a resist pattern.

The sensitivity, resolution, dry etching resistance (etching rate) and transmittance concerned with the obtained resist pattern were measured and evaluated as follows. The results are shown in Table 3.

<Sensitivity>
Sensitivity was defined as a light exposure (mJ/cm$^2$), which forms a line-and-space pattern (line/space=1/1) at a line width of 1/1.

<Resolution>
Resolution was defined as the minimal dimension (μm) of a resist pattern, which was resolved when exposure was carried out at the above-described light exposure.

<Dry Etching Resistance>
The resist film formed on a silicon wafer was subjected to etching, and the etching rate of each resist was measured by the reduction of the thickness of individual films (normalized by setting the etching rate of a novolac resin as 1). Etching was carried out employing an etching machine produced by Tokyo Electron Ltd., using $C_4F_8/Ar/O_2$ mixed gas, under etching conditions at 2,000 w, at 50 mTorr, for 50 seconds.

The surface of a resist was observed with an electron microscope after etching, and a resist having no unevenness on the surface was evaluated with a mark of "○" and a resist having unevenness and roughness on the surface was evaluated with a mark of "x".

<Transmittance>
The resist film formed on a silicon wafer was subjected to an ultraviolet-visible spectrophotometer to measure transmittance (%/μm) at 193 nm that is the wavelength of an ArF excimer laser.

TABLE 3

|  | Sensitivity (mJ/cm$^2$) | Resolution (μm) | Etching rate | Surface roughness after etching | Transmittance (%/μm) |
|---|---|---|---|---|---|
| Example B1 | 4.8 | 0.18 | 1.03 | ○ | 63 |
| Example B2 | 5.0 | 0.18 | 1.05 | ○ | 61 |
| Example B3 | 4.6 | 0.17 | 1.03 | ○ | 64 |
| Example B4 | 4.5 | 0.17 | 1.04 | ○ | 62 |
| Example B5 | 4.2 | 0.17 | 1.11 | ○ | 65 |
| Example B6 | 4.8 | 0.17 | 1.04 | ○ | 62 |
| Example B7 | 4.0 | 0.17 | 1.09 | ○ | 68 |
| Example B8 | 4.6 | 0.18 | 1.10 | ○ | 66 |
| Example B9 | 4.7 | 0.18 | 1.15 | ○ | 64 |
| Example B10 | 5.0 | 0.18 | 1.13 | ○ | 65 |
| Example B11 | 5.0 | 0.17 | 1.05 | ○ | 63 |
| Example B12 | 4.8 | 0.17 | 1.04 | ○ | 63 |

TABLE 3-continued

| | Sensitivity (mJ/cm$^2$) | Resolution (μm) | Etching rate | Surface roughness after etching | Transmittance (%/μm) |
|---|---|---|---|---|---|
| Example B13 | 4.7 | 0.17 | 1.04 | ○ | 62 |
| Comparative Example B1 | 5.0 | 0.19 | 1.05 | ○ | 57 |
| Comparative Example B2 | 3.6 | 0.16 | 1.26 | x | 70 |

Thus, the chemically amplified resist compositions comprising the polymers of the present invention (Examples B1 to B13) had excellent solubility in commonly used resist solvents, sufficient sensitivity and resolution, and excellent dry etching resistance and transmittance. In contrast, the polymer of comparative Example B1 had poor solubility in organic solvents, and the chemically amplified resist composition comprising the polymer of comparative Example B1 had poor transmittance. The chemically amplified resist composition comprising the polymer of Comparative Example B2 had poor sensitivity and etching resistance.

INDUSTRIAL APPLICABILITY

The present invention provides a (meth)acrylate having a condensed ring structure or a cross-linking ring structure comprising a γ-butyrolactone structure in its molecule, which is excellent in heat resistance, moderate polarity, and solubility in organic solvents; a raw material alcohol for the (meth)acrylate; and a method of producing these compounds which is easy to perform, has high yield, and is excellent in productivity.

The polymer of the present invention obtained by (co)polymerizing the (meth)acrylate is excellent in transparency, dry etching resistance, and solubility in organic solvents, and so it is preferable as a resin for a chemically amplified resist composition.

The chemically amplified resist composition of the present invention comprising this polymer has high transparency, and it has only a little roughness on a resist surface thereof after etching, having good dry etching resistance. Moreover, the chemically amplified resist composition has high sensitivity and resolution.

According to the pattern formation method of the present invention, in which the chemically amplified resist composition is used, a high-precision fine resist pattern can stably be formed. The chemically amplified resist composition comprising the polymer of the present invention is preferably used in far ultraviolet excimer laser lithography and electron beam lithography, and particularly in lithography using an ArF excimer laser.

What is claimed is:

1. A polymer produced by (co)polymerizing a monomer composition comprising the monomer represented by formula (1):

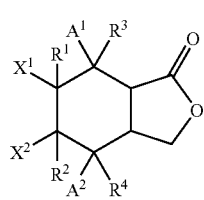

(1)

wherein each of $R^1$, $R^2$, $R^3$ and $R^4$ represents a hydrogen atom, a methyl group or an ethyl group; either one of $X^1$ or $X^2$ represents a (meth)acryloyloxy group and the other represents a hydrogen atom; both $A^1$ and $A^2$ represent hydrogen atoms, or $A^1$ and $A^2$ form —O—, —CH$_2$— or —CH$_2$CH$_2$—.

2. The polymer according to claim 1, wherein, any one of $R^1$, $R^2$, $R^3$ and $R^4$ represents a methyl group and the others represent hydrogen atoms.

3. The polymer according to claim 1, which is represented by the following formula (5-1):

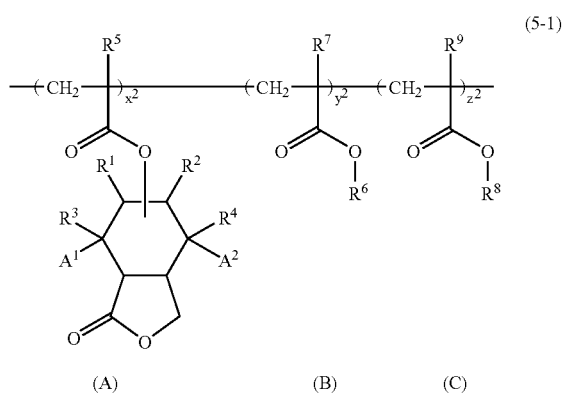

(5-1)

wherein each of $R^1$, $R^2$, $R^3$ and $R^4$ represents a hydrogen atom, a methyl group or an ethyl group; each of $R^5$, $R^7$ and $R^9$ represents a hydrogen atom or a methyl group; $R^6$ represents a cyclic hydrocarbon group having a group that is eliminated by acid; $R^8$ represents a group having a hydrophilic functional group or a hydrogen atom; both $A^1$ and $A^2$ represent hydrogen atoms, or $A^1$ and $A^2$ form —O—, —CH$_2$— or —CH$_2$CH$_2$—; and $x^2$, $y^2$ and $z^2$ represent the ratios of a unit (A), a unit (B) and a unit (C), respectively, wherein, when $x^2+y^2+z^2=1$, $x^2$, $y^2$ and $z^2$ are any given numbers satisfying $0<x^2\leq 1$, $0\leq y^2<1$, and $0\leq z^2<1$.

4. The polymer according to claim 3, wherein $R^6$ contains at least one selected from the group consisting of a cyclohexyl group, an isobornyl group, an adamantyl group, a tricyclodecanyl group, a dicyclopentadienyl group, and substituted compounds thereof.

5. The polymer according to claim 1, which is represented by the following formula (5-2):

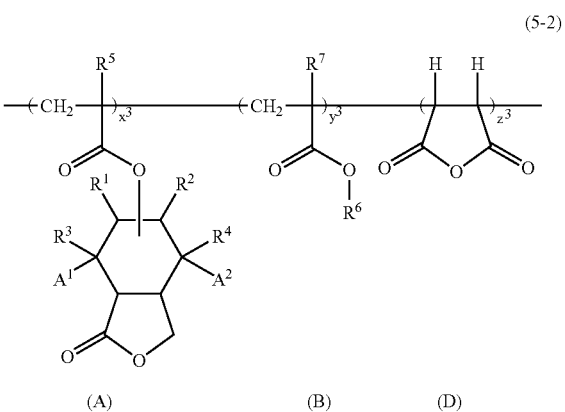

(5-2)

wherein each of $R^1$, $R^2$, $R^3$ and $R^4$ represents a hydrogen atom, a methyl group or an ethyl group; each of $R^5$ and $R^7$ represents a hydrogen atom or a methyl group; $R^6$ represents a cyclic hydrocarbon group having a group that is eliminated by acid; both $A^1$ and $A^2$ represent hydrogen atoms, or $A^1$ and $A^2$ form —O—, —$CH_2$— or —$CH_2CH_2$—; and $x^3$, $y^3$ and $z^3$ represent the ratios of a unit (A), a unit (B) and a unit (D), respectively, wherein, when $x^3+y^3+z^3=1$, $x^3$, $y^3$ and $z^3$ are any given numbers satisfying $0<x^3\leq1$, $0\leq y^3<1$, and $0\leq z^3<1$.

6. The polymer according to claim 5, wherein $R^6$ contains at least one selected from the group consisting of a cyclohexyl group, an isobornyl group, an adamantyl group, a tricyclodecanyl group, a dicyclopentadienyl group, and substituted compounds thereof.

7. The polymer according to claim 1, which is represented by the following formula (5-3):

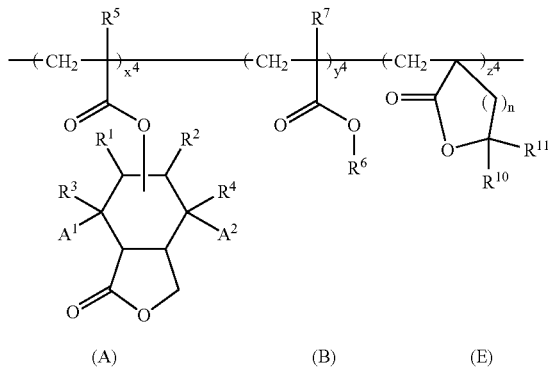

(5-3)

wherein each of $R^1$, $R^2$, $R^3$, $R^4$, $R^{10}$ and $R^{11}$ represents a hydrogen atom, a methyl group or an ethyl group; each of $R^5$ and $R^7$ represents a hydrogen atom or a methyl group; $R^6$ represents a cyclic hydrocarbon group having a group that is eliminated by acid; both $A^1$ and $A^2$ represent hydrogen atoms, or $A^1$ and $A^2$ form —O—, —$CH_2$— or —$CH_2CH_2$—; n represents an integer of 0 to 4; and $x^4$, $y^4$ and $z^4$ represent the ratios of a unit (A), a unit (B) and a unit (E), respectively, wherein, when $x^4+y^4+z^4=1$, $x^4$, $y^4$ and $z^4$ are any given numbers satisfying $0<x^4\leq1$, $0\leq y^4<1$, and $0\leq z^4<1$.

8. The polymer according to claim 7, wherein $R^6$ contains at least one selected from the group consisting of a cyclohexyl group, an isobornyl group, an adamantyl group, a tricyclodecanyl group, a dicyclopentadienyl group, and substituted compounds thereof.

9. The polymer according to claim 1, which has a weight-average molecular weight of 1,000 to 100,000.

10. The polymer according to claim 3, which has a weight-average molecular weight of 1,000 to 100,000.

11. The polymer according to claim 5, which has a weight-average molecular weight of 1,000 to 100,000.

12. The polymer according to claim 7, which has a weight-average molecular weight of 1,000 to 100,000.

13. The polymer according to claim 1 wherein $A^1$ and $A^2$ form —$CH_2$—.

* * * * *